(12) United States Patent
Keady

(10) Patent No.: US 11,477,560 B2
(45) Date of Patent: Oct. 18, 2022

(54) EARPLUGS, EARPHONES, AND EARTIPS

(71) Applicant: HEAR LLC, Fairfax Station, VA (US)

(72) Inventor: John P Keady, Fairfax Station, VA (US)

(73) Assignee: HEAR LLC, Fairfax Station, VA (US)

( * ) Notice: Subject to any disclaimer, the term of this patent is extended or adjusted under 35 U.S.C. 154(b) by 153 days.

(21) Appl. No.: 16/905,655

(22) Filed: Jun. 18, 2020

(65) Prior Publication Data

US 2020/0359122 A1   Nov. 12, 2020

Related U.S. Application Data

(63) Continuation-in-part of application No. 16/590,466, filed on Oct. 2, 2019, now abandoned, and a continuation-in-part of application No. 15/674,239, filed on Aug. 10, 2017, now abandoned, and a continuation-in-part of application No. 15/182,569, filed on Jun. 14, 2016, now abandoned.

(60) Provisional application No. 62/740,408, filed on Oct. 2, 2018, provisional application No. 62/437,331, filed on Dec. 21, 2016, provisional application No. 62/373,313, filed on Aug. 10, 2016, provisional application No. 62/307,486, filed on Mar. 12, 2016, provisional application No. 62/307,484, filed on Mar. 12, 2016, provisional application No. 62/239,337, filed on Oct. 9, 2015, provisional application No. 62/217,663, filed on Sep. 11, 2015.

(51) Int. Cl.
    *H04R 25/00* (2006.01)
    *H04R 1/10* (2006.01)

(52) U.S. Cl.
    CPC .................. *H04R 1/1016* (2013.01)

(58) Field of Classification Search
    CPC .................................... H04R 1/1016
    USPC ........................................ 381/380
    See application file for complete search history.

(56) References Cited

U.S. PATENT DOCUMENTS

| | | |
|---|---|---|
| 2,850,012 A | 9/1958 | Becker |
| 2,876,767 A | 3/1959 | Nathan |
| 3,110,356 A | 11/1963 | Mendelson |
| 3,505,999 A | 4/1970 | Harvey et al. |
| 3,602,654 A | 8/1971 | Victoreen |

(Continued)

FOREIGN PATENT DOCUMENTS

| | | |
|---|---|---|
| WO | 2011163565 A | 12/2011 |
| WO | 2019173809 | 9/2019 |

OTHER PUBLICATIONS

Mien, C. H. and E. H. Berger: Development of a unique passive hearing protector with level-dependent and flat attenuation characteristics. Noise Control Engineering Journal, 34(3), 97-105 (1990).

(Continued)

*Primary Examiner* — Phylesha Dabney
(74) *Attorney, Agent, or Firm* — John P. Keady

(57) ABSTRACT

At least one exemplary embodiment is directed to an earphone, ear device, eartip, or earplug configured to inserted in an ear canal of the ear. The earphone, ear device, eartip, or earplug is configured to occlude or partially occlude the ear canal of the ear. The earphone, ear device, eartip, or earplug includes a chamber to occlude or partially occlude the ear canal that is sealed when inserted in the ear canal and open to the external environment when outside the ear.

8 Claims, 46 Drawing Sheets

(56) References Cited

U.S. PATENT DOCUMENTS

| | | | |
|---|---|---|---|
| 4,006,796 A | 2/1977 | Coehorst | |
| 4,029,083 A | 6/1977 | Baylor | |
| 4,060,080 A | 11/1977 | Akiyama | |
| 4,834,211 A | 5/1989 | Bibby et al. | |
| 4,896,679 A | 1/1990 | Pierre | |
| 4,913,165 A | 4/1990 | Fishgoyt | |
| 5,131,411 A | 7/1992 | Casali et al. | |
| 5,333,622 A | 8/1994 | Casali et al. | |
| 6,256,396 B1 * | 7/2001 | Cushman | H04R 25/658 381/328 |
| 6,368,288 B2 | 4/2002 | Stone | |
| 6,368,289 B2 | 4/2002 | Stone | |
| 6,440,102 B1 | 8/2002 | Arenberg et al. | |
| 7,171,371 B2 | 1/2007 | Goldstein | |
| 7,756,281 B2 | 7/2010 | Goldstein et al. | |
| 7,779,844 B2 | 8/2010 | Purcell et al. | |
| 7,817,803 B2 | 10/2010 | Goldstein | |
| 7,822,219 B2 | 10/2010 | Baker et al. | |
| 7,886,745 B2 | 2/2011 | Purcell et al. | |
| 7,913,696 B2 | 3/2011 | Purcell et al. | |
| 8,018,328 B2 | 9/2011 | Goldstein et al. | |
| 8,047,207 B2 | 11/2011 | Perez et al. | |
| 8,081,780 B2 | 12/2011 | Goldstein et al. | |
| 8,111,839 B2 | 2/2012 | Goldstein et al. | |
| 8,142,870 B2 | 3/2012 | Keady | |
| 8,150,043 B2 | 4/2012 | Goldstein et al. | |
| 8,150,044 B2 | 4/2012 | Goldstein et al. | |
| 8,170,228 B2 | 5/2012 | Goldstein et al. | |
| 8,194,864 B2 | 6/2012 | Goldstein et al. | |
| 8,194,865 B2 | 6/2012 | Goldstein et al. | |
| 8,199,919 B2 | 6/2012 | Goldstein et al. | |
| 8,208,644 B2 | 6/2012 | Goldstein et al. | |
| 8,208,652 B2 | 6/2012 | Keady | |
| 8,213,629 B2 | 7/2012 | Goldstein et al. | |
| 8,213,649 B2 | 7/2012 | Goldstein et al. | |
| 8,221,860 B2 | 7/2012 | Keady | |
| 8,221,861 B2 | 7/2012 | Keady | |
| 8,229,128 B2 | 7/2012 | Keady | |
| 8,251,925 B2 | 8/2012 | Keady et al. | |
| 8,311,228 B2 | 11/2012 | Goldstein et al. | |
| 8,312,960 B2 | 11/2012 | Keady | |
| 8,315,400 B2 | 11/2012 | Goldstein et al. | |
| 8,319,620 B2 | 11/2012 | Usher et al. | |
| 8,326,628 B2 | 12/2012 | Goldstein et al. | |
| 8,326,635 B2 | 12/2012 | Usher et al. | |
| 8,437,492 B2 | 5/2013 | Goldstein et al. | |
| 8,447,031 B2 | 5/2013 | Usher et al. | |
| 8,499,886 B2 * | 8/2013 | Johnston | H04R 1/1016 181/129 |
| 9,479,859 B2 * | 10/2016 | Henry | A61F 11/08 |
| 9,485,595 B2 * | 11/2016 | Trine | H04R 25/652 |
| 10,917,711 B2 * | 2/2021 | Higgins | H04R 25/60 |
| 11,102,563 B2 * | 8/2021 | Stanley | H05K 5/0226 |
| 2002/0143242 A1 | 10/2002 | Nemirovski | |
| 2007/0270988 A1 | 11/2007 | Goldstein et al. | |
| 2008/0015463 A1 | 1/2008 | Goldstein | |
| 2008/0031475 A1 | 2/2008 | Goldstein | |
| 2008/0037797 A1 | 2/2008 | Goldstein et al. | |
| 2008/0046246 A1 | 2/2008 | Goldstein et al. | |
| 2008/0130906 A1 | 6/2008 | Goldstein et al. | |
| 2008/0137873 A1 | 6/2008 | Goldstein | |
| 2008/0144840 A1 | 6/2008 | Goldstein et al. | |
| 2008/0144841 A1 | 6/2008 | Goldstein et al. | |
| 2008/0144842 A1 | 6/2008 | Goldstein et al. | |
| 2008/0176289 A1 | 7/2008 | Zeng et al. | |
| 2008/0178088 A1 | 7/2008 | Goldstein et al. | |
| 2008/0181419 A1 | 7/2008 | Goldstein et al. | |
| 2008/0181442 A1 | 7/2008 | Goldstein et al. | |
| 2008/0205660 A1 | 8/2008 | Goldstein | |
| 2008/0212787 A1 | 9/2008 | Goldstein et al. | |
| 2008/0219456 A1 | 9/2008 | Goldstein et al. | |
| 2008/0219486 A1 | 9/2008 | Goldstein et al. | |
| 2008/0240458 A1 | 10/2008 | Goldstein et al. | |
| 2008/0253583 A1 | 10/2008 | Goldstein et al. | |
| 2008/0267416 A1 | 10/2008 | Goldstein et al. | |
| 2008/0299339 A1 | 12/2008 | Keady | |
| 2008/0311324 A1 | 12/2008 | Keady | |
| 2009/0016541 A1 | 1/2009 | Goldstein et al. | |
| 2009/0016542 A1 | 1/2009 | Goldstein et al. | |
| 2009/0022294 A1 | 1/2009 | Goldstein et al. | |
| 2009/0022353 A1 | 1/2009 | Goldstein et al. | |
| 2009/0028356 A1 | 1/2009 | Ambrose et al. | |
| 2009/0034765 A1 | 2/2009 | Boil et al. | |
| 2009/0067661 A1 | 3/2009 | Keady et al. | |
| 2009/0071486 A1 | 3/2009 | Perez et al. | |
| 2009/0071487 A1 | 3/2009 | Keady | |
| 2009/0101433 A1 * | 4/2009 | Stiehl | H04R 1/1016 181/129 |
| 2009/0130423 A1 | 5/2009 | Keady | |
| 2009/0146799 A1 | 6/2009 | Goldstein et al. | |
| 2009/0147966 A1 | 6/2009 | Mcintosh et al. | |
| 2009/0154748 A1 | 6/2009 | Baker et al. | |
| 2009/0155518 A1 | 6/2009 | Keady | |
| 2009/0192407 A1 | 7/2009 | Keady et al. | |
| 2009/0214072 A1 | 8/2009 | Staab et al. | |
| 2009/0220096 A1 | 9/2009 | Usher et al. | |
| 2009/0238374 A1 | 9/2009 | Keady | |
| 2009/0238386 A1 | 9/2009 | Usher et al. | |
| 2009/0240497 A1 | 9/2009 | Usher et al. | |
| 2009/0245530 A1 | 10/2009 | Keady | |
| 2009/0264161 A1 | 10/2009 | Usher et al. | |
| 2009/0290721 A1 | 11/2009 | Goldstein et al. | |
| 2010/0002897 A1 | 1/2010 | Keady | |
| 2010/0012420 A1 | 1/2010 | Keady | |
| 2010/0033313 A1 | 2/2010 | Keady et al. | |
| 2010/0071707 A1 | 3/2010 | Wohl | |
| 2010/0074451 A1 | 3/2010 | Usher et al. | |
| 2010/0076793 A1 | 3/2010 | Goldstein et al. | |
| 2010/0135502 A1 | 6/2010 | Keady et al. | |
| 2010/0142715 A1 | 6/2010 | Goldstein et al. | |
| 2010/0142725 A1 | 6/2010 | Goldstein et al. | |
| 2010/0177918 A1 | 7/2010 | Keady et al. | |
| 2010/0241256 A1 | 9/2010 | Goldstein et al. | |
| 2010/0322454 A1 | 12/2010 | Ambrose et al. | |
| 2011/0079227 A1 | 4/2011 | Turcot et al. | |
| 2011/0085689 A1 | 4/2011 | Keady | |
| 2011/0115626 A1 | 5/2011 | Goldstein et al. | |
| 2011/0228963 A1 | 9/2011 | Goldstein et al. | |
| 2011/0235843 A1 | 9/2011 | Keady et al. | |
| 2011/0311079 A1 | 12/2011 | Keady | |
| 2012/0101514 A1 | 4/2012 | Keady et al. | |
| 2012/0103346 A1 | 5/2012 | Keady | |
| 2012/0123573 A1 | 5/2012 | Goldstein et al. | |
| 2012/0177209 A1 | 7/2012 | Goldstein et al. | |
| 2012/0177210 A1 | 7/2012 | Goldstein et al. | |
| 2012/0288104 A1 | 11/2012 | Goldstein et al. | |
| 2013/0035608 A1 | 2/2013 | Goldstein et al. | |
| 2013/0039518 A1 | 2/2013 | Goldstein et al. | |
| 2013/0098706 A1 | 4/2013 | Keady | |
| 2013/0123919 A1 | 5/2013 | Goldstein et al. | |
| 2016/0057551 A1 * | 2/2016 | Higgins | H04R 31/00 381/328 |
| 2019/0111456 A1 * | 4/2019 | Aase | B08B 17/04 |
| 2020/0314519 A1 * | 10/2020 | Hatfield | H04R 1/1016 |
| 2021/0152924 A1 * | 5/2021 | Keady | A61F 11/08 |
| 2021/0243514 A1 * | 8/2021 | Hatfield | H04R 1/1016 |

OTHER PUBLICATIONS

Casali, J. G. and Berger, E. H. Technology advancements in hearing protection: Active noise reduction, frequency/amplitude-sensitivity, and uniform attenuation. American Industrial Hygiene Association Journal, 57, 175-185. (1996).

Casali, J. G. and Gerges, S., Protection and enhancement of hearing in noise, in Williges, R. C., Ed. Reviews of Human Factors and Ergonomics, vol. 2. Human Factors and Ergonomics Society Santa Monica, CA, 7, 195-240, (2006).

Casali, J. G., Advancements in hearing protection: Technology, applications, and challenges for performance testing and product labeling. Proceedings of the 2005 International Congress and Exhibition of Noise-Control Engineering, Rio de Janeiro, Brazil, 2097-2118 (2005).

(56) References Cited

OTHER PUBLICATIONS

Casali, J. G., Ahroon,W. A., and Lancaster, J. A field investigation of hearing protection and hearing enhancement in one device: For soldiers whose ears and lives depend upon it. Noise and Health Journal, 11 (42), 69-90 (2009).

Casali, J. G., Mauney, D. W., and Burks, J. A. Physical vs. psychophysical measurement of hearing protector attenuation—a.k.a. MIRE vs. REAT. Sound and Vibration, 29(7), 20-27, (1995).

Casali, J. G., Passive Augmentations in Hearing Protection Technology Circa 2010: Flat-Attenuation, Passive Level-Dependent, Passive Wave Resonance, Passive Adjustable Attenuation, and Adjustable-Fit Devices: Review of Design, Testing, and Research. International Journal of Acoustics and Vibrations, 15(4), 187-195 (Dec. 2010).

Gerges S. and Casali J. G . . . Hearing protectors. in Crocker. M . . . Ed. Handbook of Noise and Vibration Control. John Wiley, New York, 31, 359-372, (2007).

Lee, Kichol, "Effects of Earplug Material, Insertion Depth, and Measurement Technique on Hearing Occlusion Effect", Dissertation submitted to the Faculty of the Virginia Polytechnic Institute and State University, Jan. 21, 2011, Blacksburg, Virginia.

Mosko, J. D. and Fletcher, J. L., Evaluation of the Gunfender earplug: Temporary threshold shift and speech intelligibility. Journal of the Acoustical Society of America, 49, 1732-1733 (1971 ).

Perala, C. H. and Casali, J. G. Human subject investigation of MIRE microphone location during insertion loss testing of Active Noise Reduction hearing protectors in active and passive modes. Noise Control Engineering Journal, 57(5), 442-458, Sep.-Oct. 2009.

Suter, A. H., The effects of hearing protectors on speech communication and the perception of warning signals (AMCMS Code 611102.74A0011 ), Aberdeen Proving Ground, MD: U.S. Army Human Engineering Laboratory, 1-32, (1989).

Witt, B. Can you hear flat?? Proceedings (on CD) of the 31st Annual National Hearing Conservation Association Conference, Tampa, FL, Feb. 16-18, 2006.

\* cited by examiner

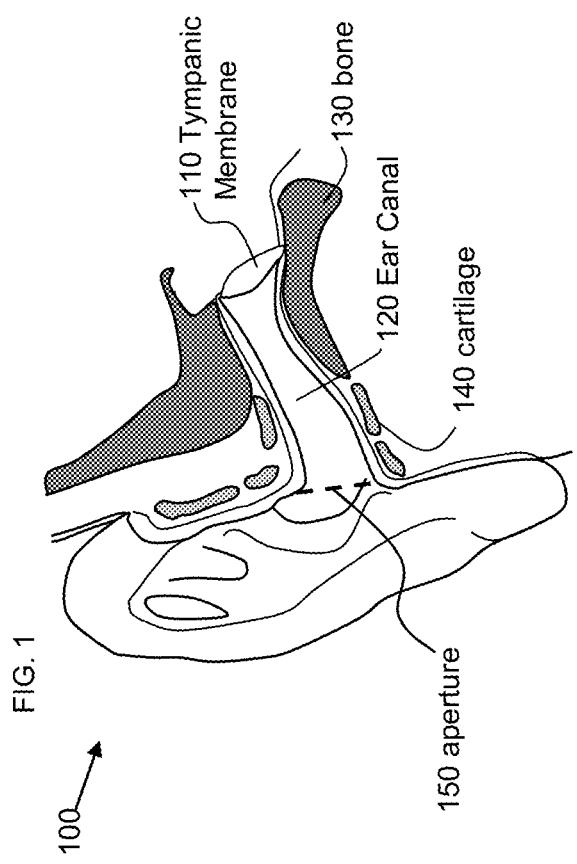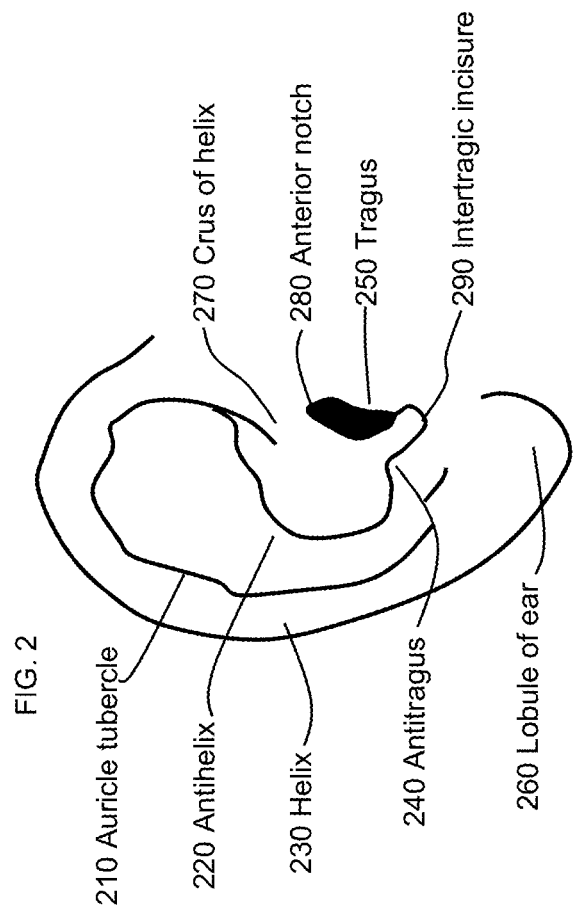

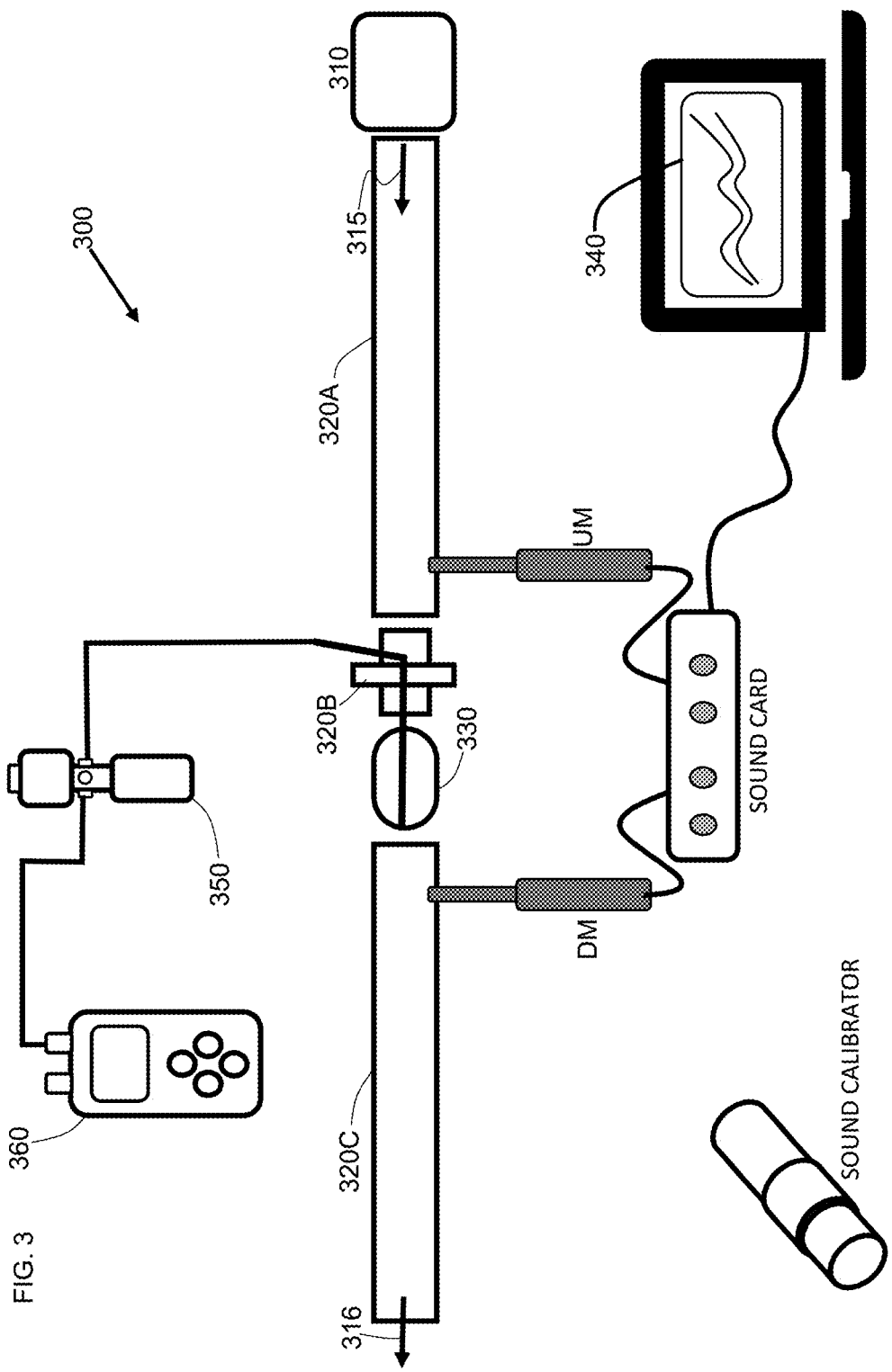

FIG. 11: Cartoon of acoustical waves traveling through a cross-section of a medium in region II (R2), encapsulated by a membrane.

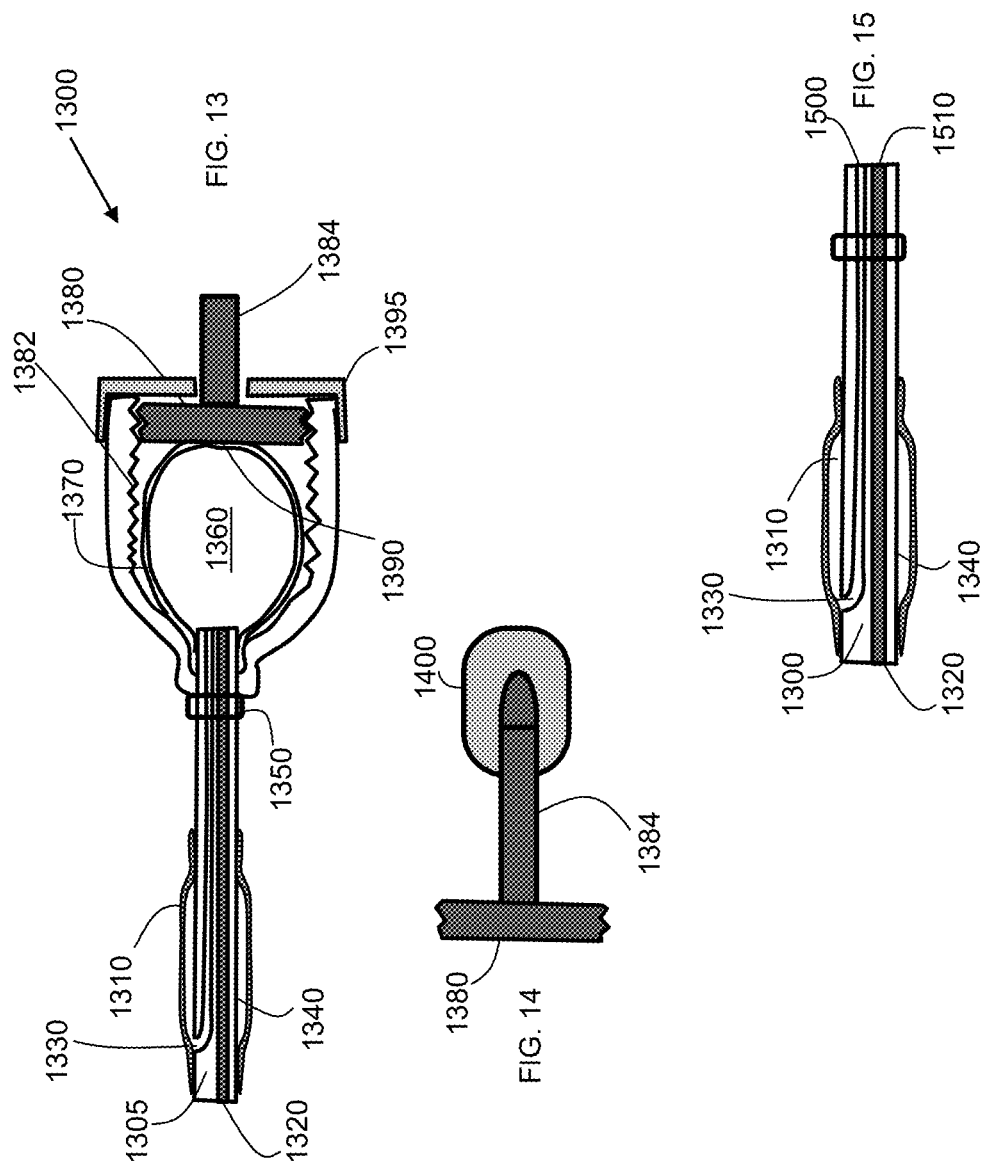

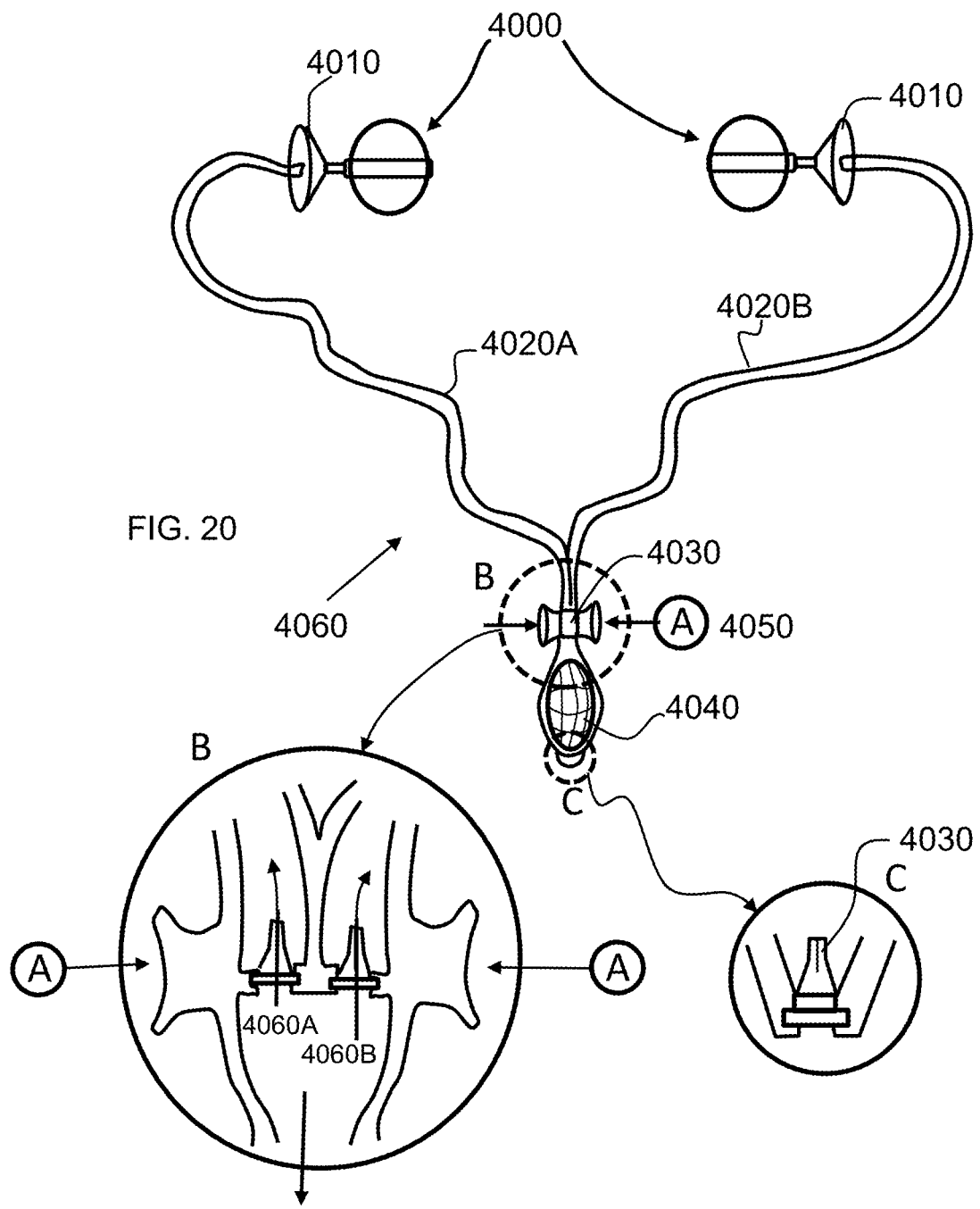

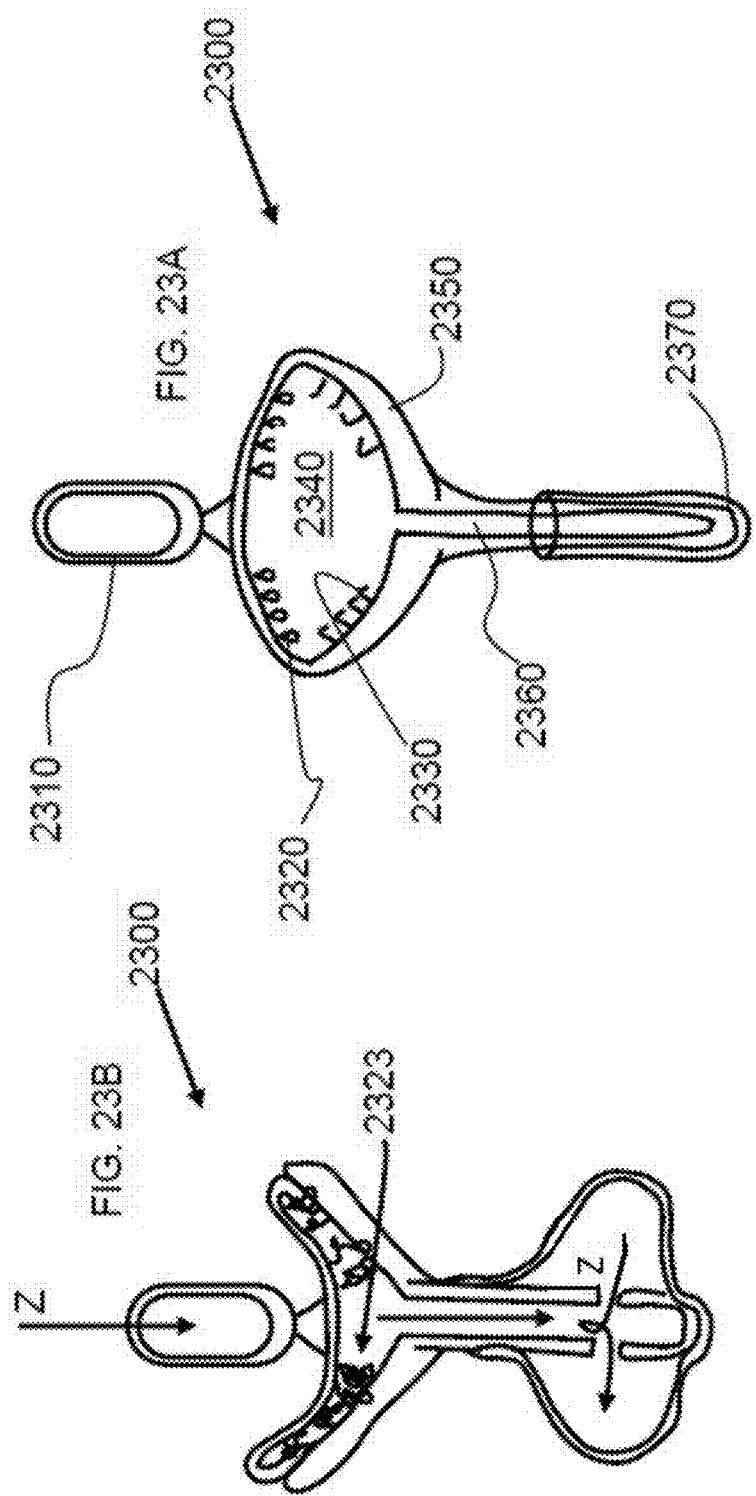

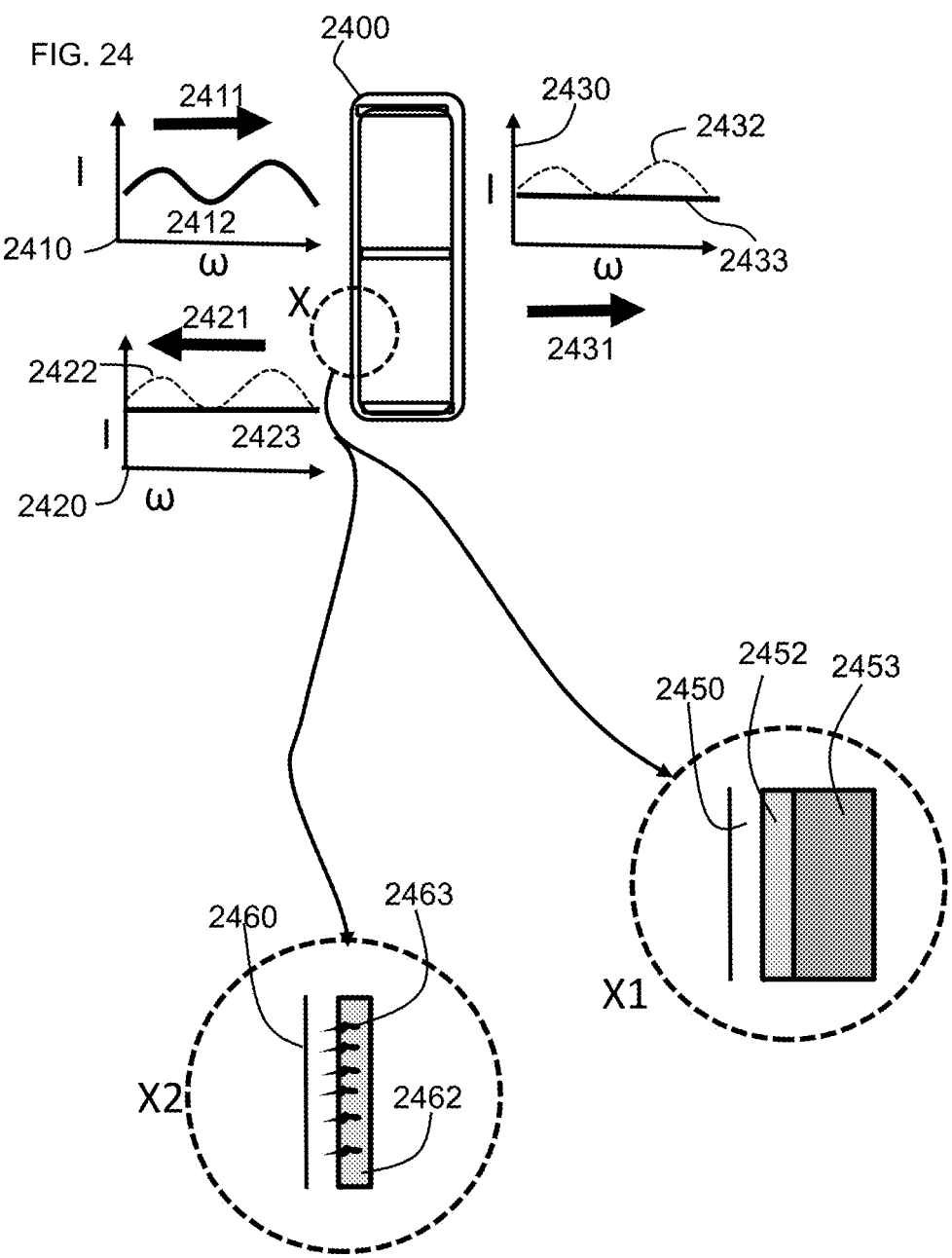

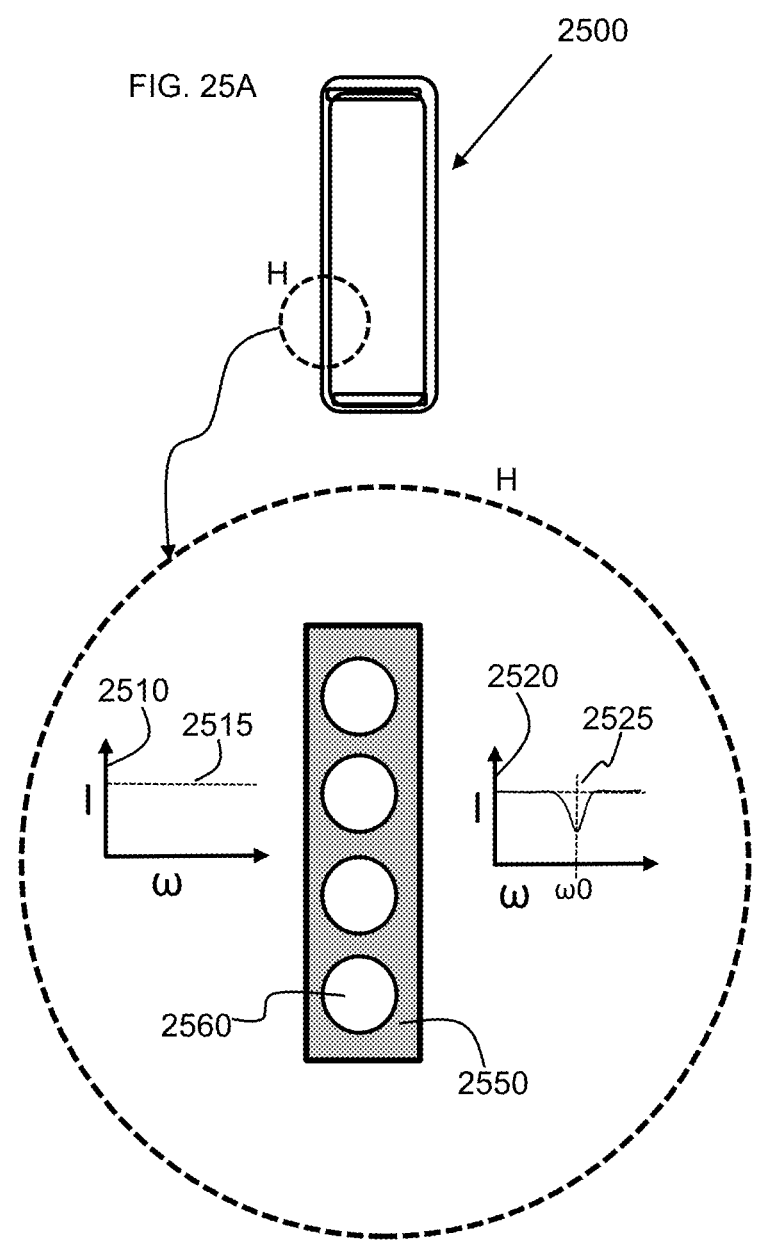

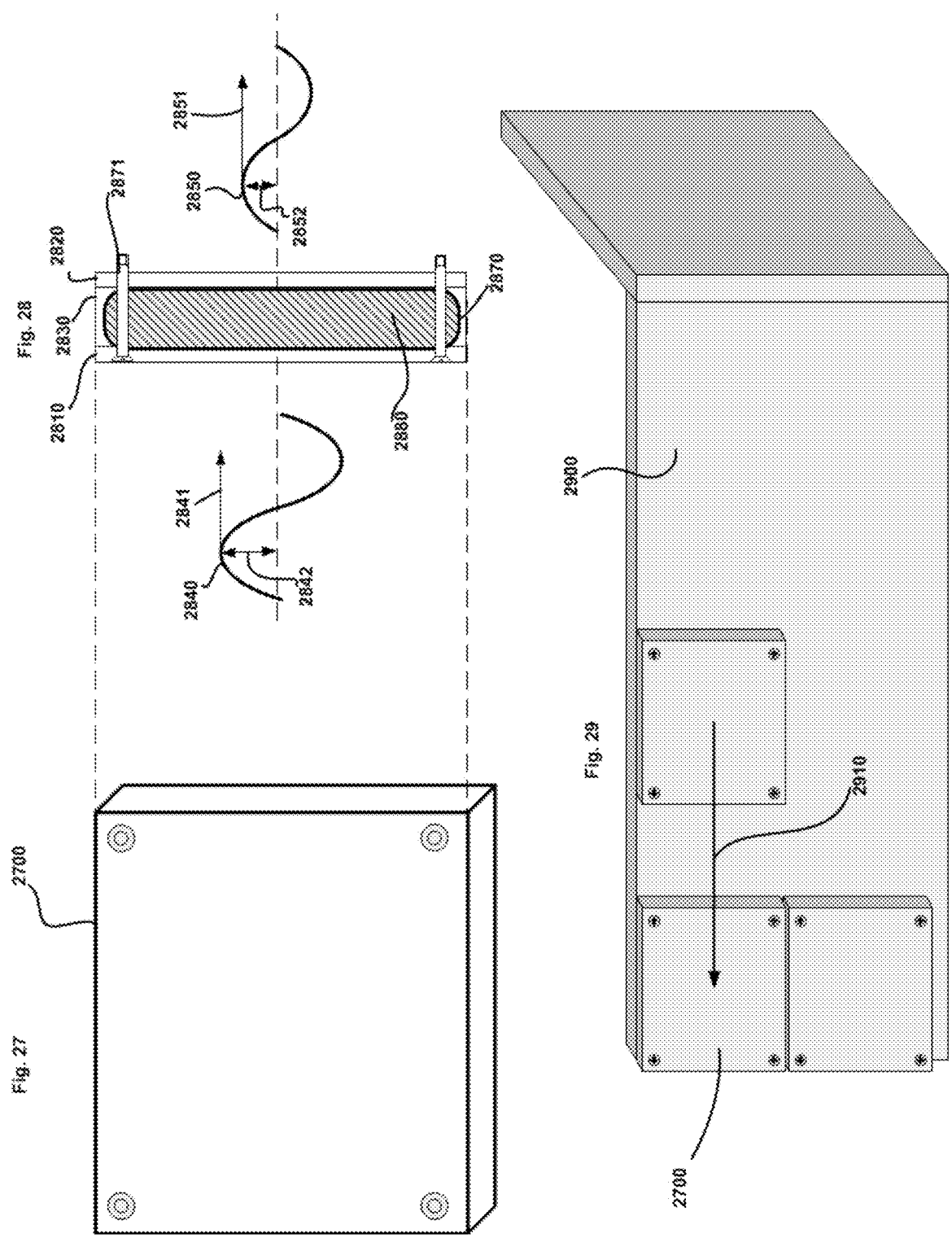

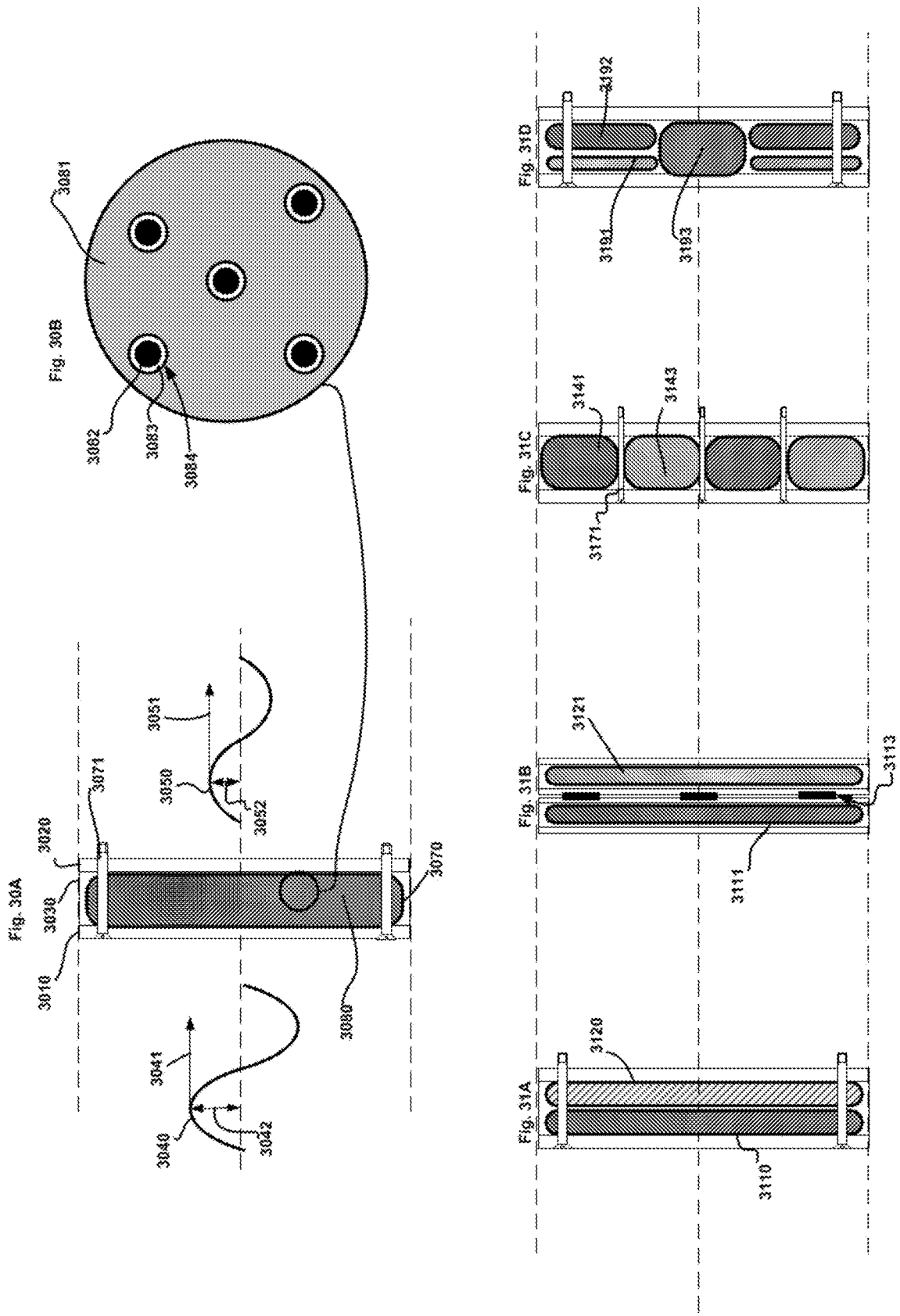

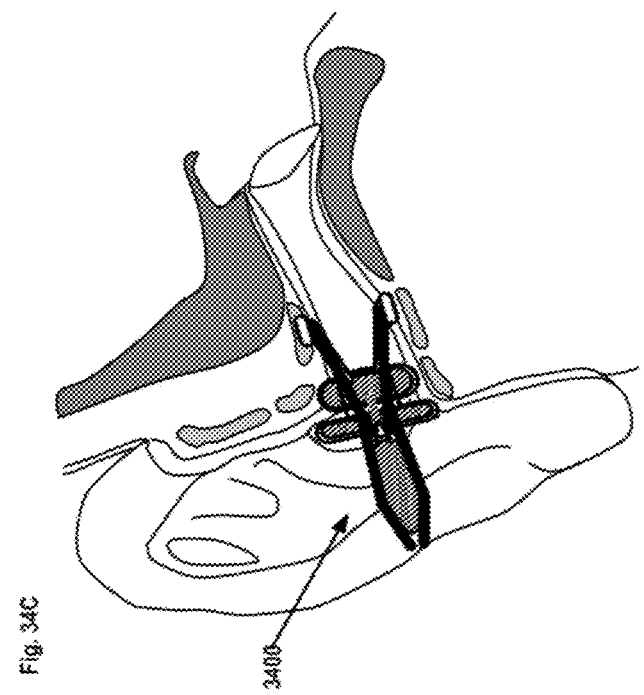
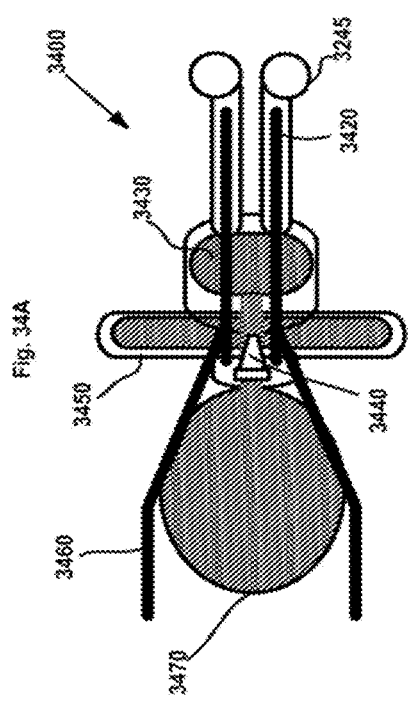
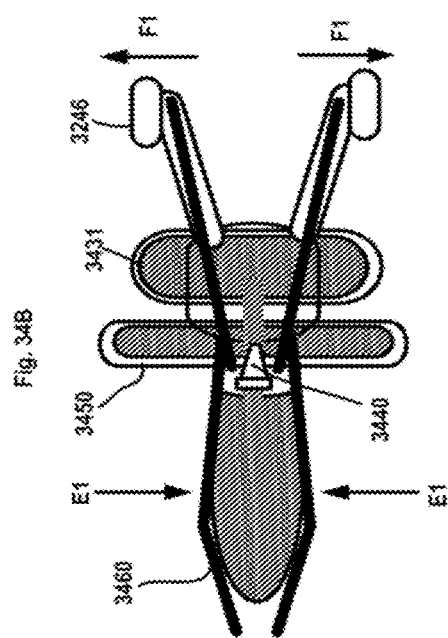

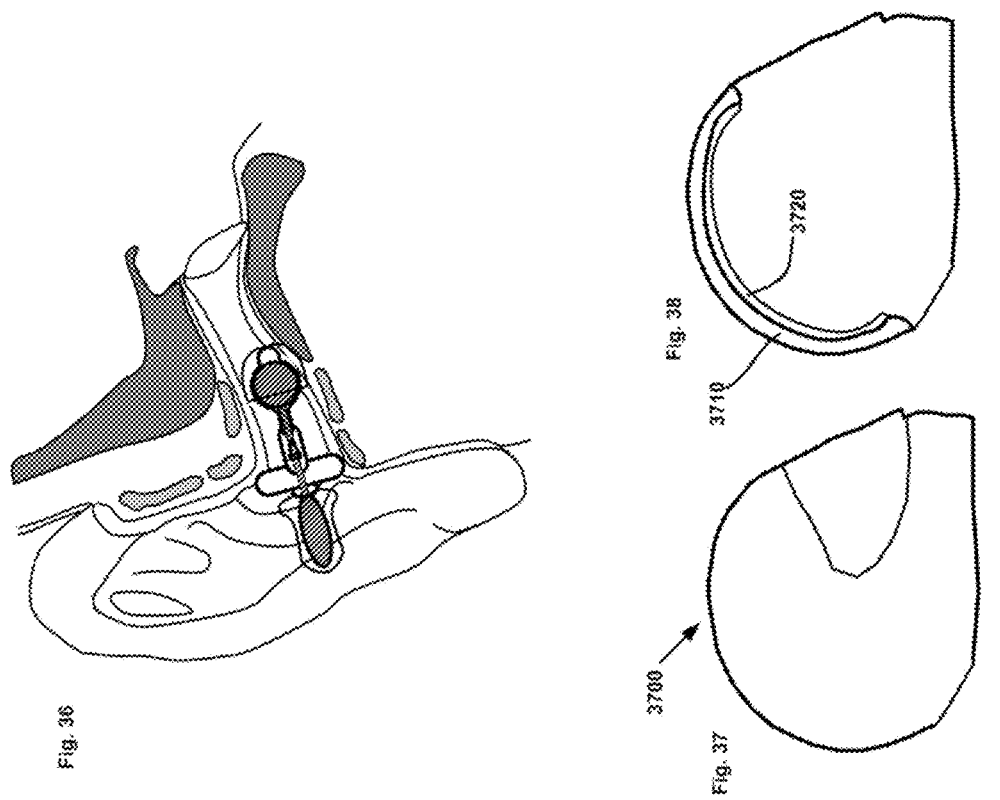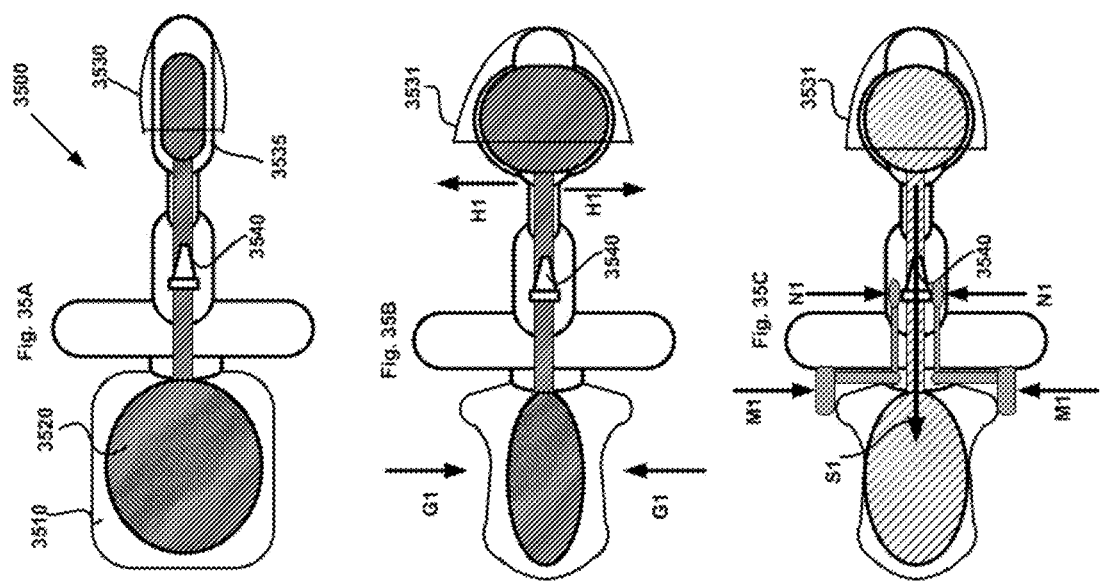

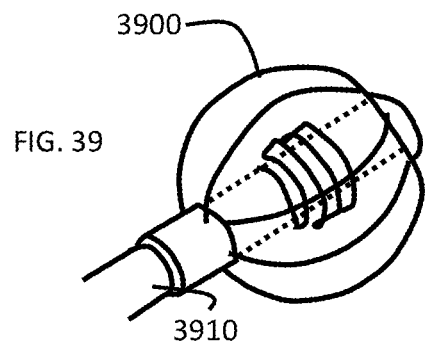
FIG. 39
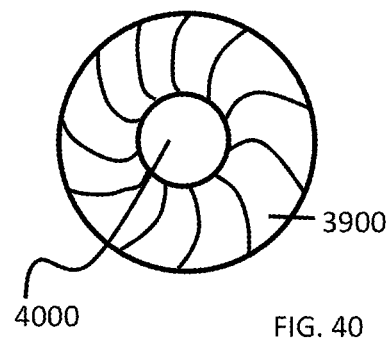
FIG. 40
FIG. 41
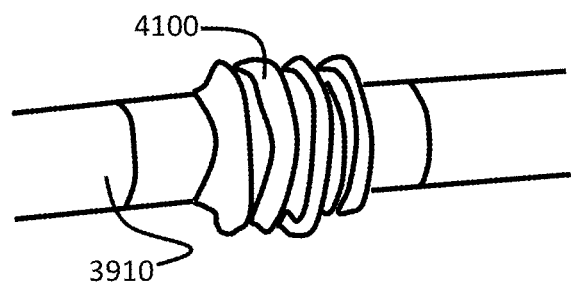

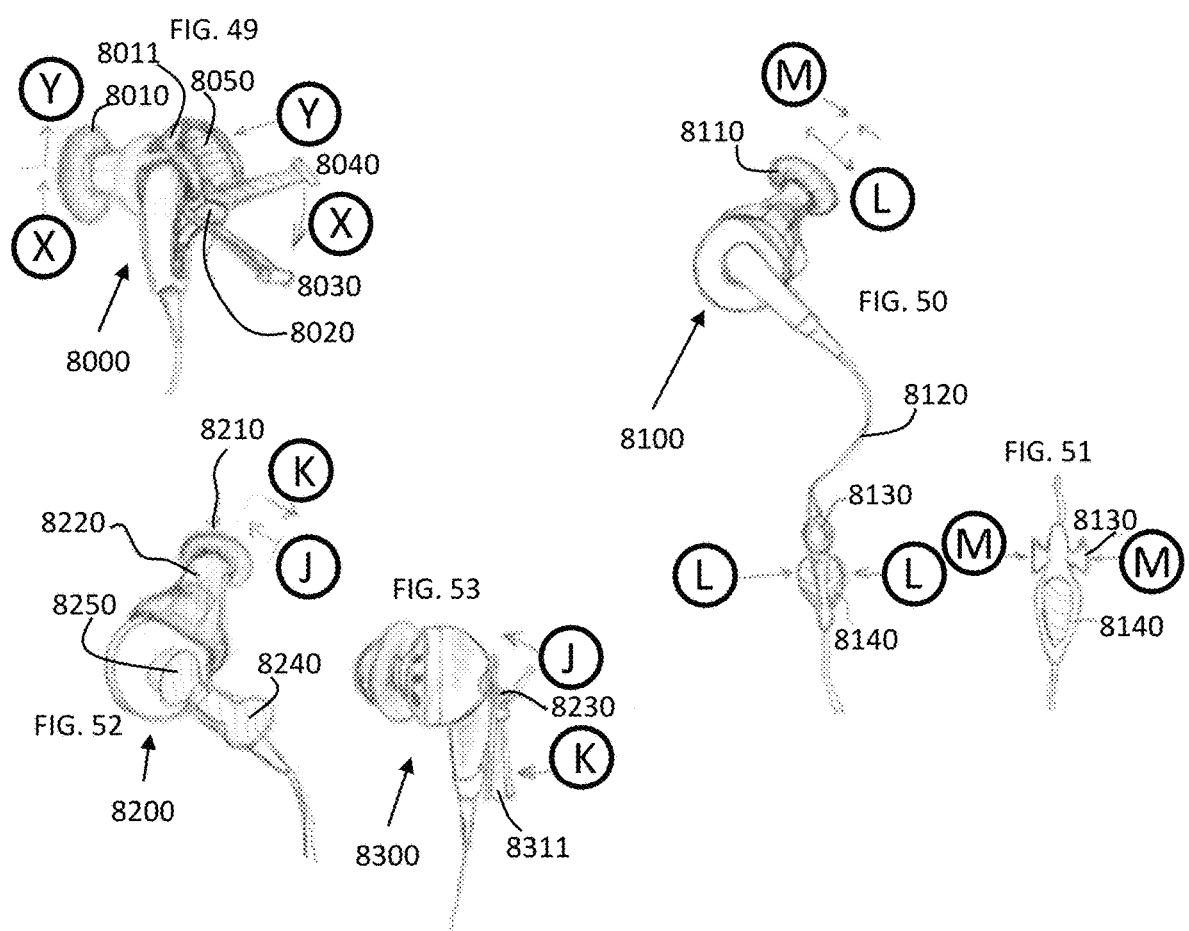

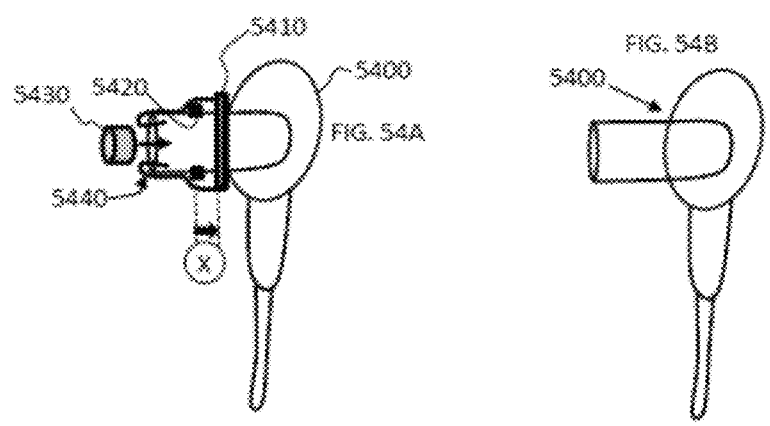
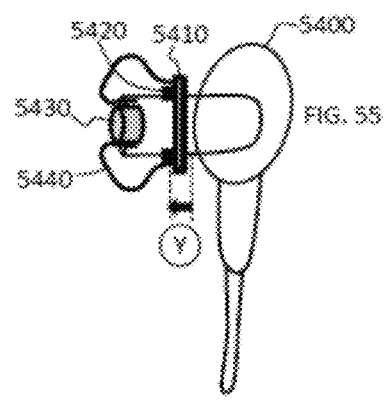

- 9082: inserting an ear device into an ear canal of an ear wherein a chamber is configured to occlude or partially occlude the ear canal of the ear wherein the ear device comprises at least one stent and the chamber, wherein the chamber is formed around the at least one stent and wherein the chamber has a ring valve having an opening 360 degrees around the at least one stent

- 9084: closing the ring valve wherein the ring valve is configured to close when inserted in the ear canal, wherein a force is applied by the ear canal closes the opening in the ring valve such that the chamber is sealed

- 9086: sealing the ring valve wherein the ring valve comprises a first folding member overlying a second folding member wherein the ring valve is open prior to being inserting in the ear canal, wherein the ear canal is configured to apply a force that closes the opening of the ring valve 360 degrees around the at least one stent to seal the chamber

- 9088: opening the ring valve wherein the ring valve opens when the ear device is removed from the ear

- 9090: opening the ring valve wherein the ring valve opens as the ear device is being inserted in the ear canal to support adjustment of the chamber volume to a change in diameter of the ear canal

- 9092: adjusting pressure within the chamber wherein the chamber is configured to maintain a pressure approximately equal to the external environment as a volume of the chamber changes

- 9094: coupling to the chamber to the external environment wherein the ring valve is configured to couple to the external environment when the ring valve opens in the ear canal to adjust volume of the chamber

9122 — occluding an ear canal of an ear with an ear device wherein the ear canal is occluded or partially occluded by a sealed chamber, wherein the sealed chamber is normally open to the external environment, wherein a process of inserting the ear device into the ear canal seals the chamber thereby isolating the ear canal from the external environment 9124 — closing a ring valve coupled to the chamber to seal the chamber wherein walls of the ear canal are configured to apply a force to the ring valve to close the ring valve 9126 — equalizing a pressure within the chamber as the ear device is inserted in the ear canal such that the pressure within the chamber is approximately equal to a pressure of the external environment 9128 — applying a force 360 degrees around the ring valve to seal the chamber wherein the walls of the ear canal apply the force 360 degrees around the ring valve to seal the chamber

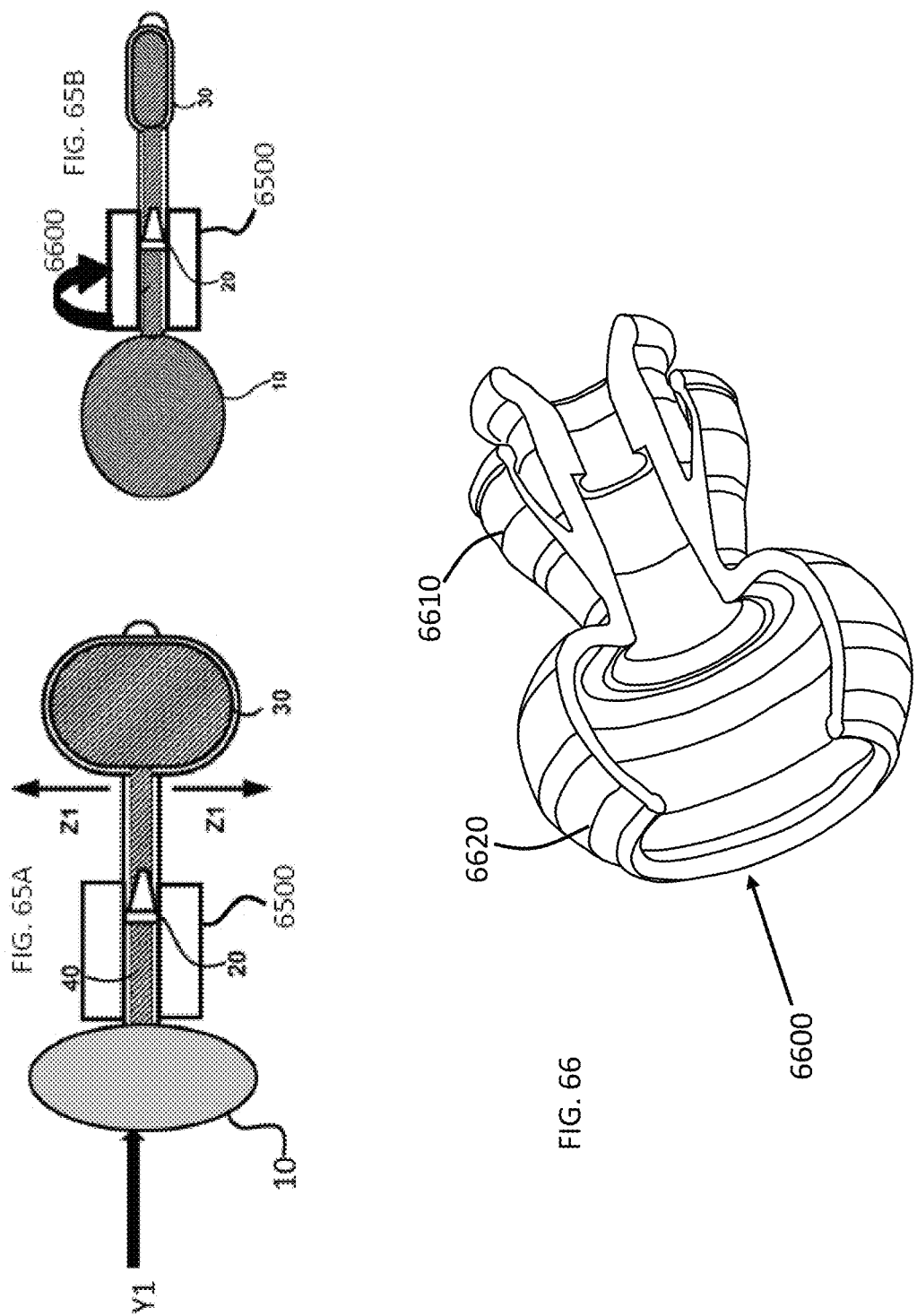

EARPLUGS, EARPHONES, AND EARTIPS

CROSS-REFERENCE TO RELATED APPLICATION(S)

This application is a continuation in part of and claims priority benefit to U.S. patent application Ser. No. 16/590,466, filed 2 Oct. 2019, which claims priority to and is a non provisional conversion of U.S. Pat. App. No. 62/740,408, filed 2 Oct. 2018, U.S. patent application Ser. No. 16/590,466 also claims priority to and is a continuation in part of U.S. patent application Ser. No. 15/674,239, filed 10 Aug. 2017, which claims priority to and is a non provisional conversion of U.S. Pat. App. No. 62/437,331, filed 21 Dec. 2016, and also which claims priority to and is a non provisional conversion of U.S. Pat. App. No. 62/373,313, filed 10 Aug. 2016, also claims priority to and is a continuation in part of U.S. patent application Ser. No. 15/182,569, filed 14 Jun. 2016, which claims priority to and is a non provisional conversion of U.S. Pat. App. No. 62/307,486, filed 12 Mar. 2016, and also which claims priority to and is a non provisional conversion of U.S. Pat. App. No. 62/307,484, filed 12 Mar. 2016, and also which claims priority to and is a non provisional conversion of U.S. Pat. App. No. 62/239,337, filed 9 Oct. 2015, and also which claims priority to and is a non provisional conversion of U.S. Pat. App. No. 62/217,663, filed 11 Sep. 2015, and which claims priority to and is a continuation in part of U.S. patent application Ser. No. 14/807,887, filed 24 Jul. 2015, which claims priority to and is a non provisional conversion of U.S. Pat. App. No. 62/187,506, filed 1 Jul. 2015, and which claims priority to and is a continuation in part of U.S. patent application Ser. No. 13/859,815, filed 10 Apr. 2013, which claims priority to and is a continuation of U.S. patent application Ser. No. 13/154,429, filed 6 Jun. 2011, which claims priority to and is a non provisional conversion of U.S. Pat. App. No. 61/351,290, filed 4 Jun. 2010.

FIELD OF THE INVENTION

The present invention relates to devices that modify acoustic attenuation and reflection, and more particularly, though not exclusively, devices that can be inserted into an ear canal or used as a sound insert or panel.

BACKGROUND OF THE INVENTION

Hearing protection can take several forms such as earplugs and muffs. Such hearing protection devices attenuate acoustic energy before it reaches the eardrum (tympanum) by creating an insertion loss that is achieved by reflection of the sound waves, dissipation with the device's structure, impedance of the waves through tortuous paths, closing of acoustical valves, and other means. For a hearing protector, the amount of sound pressure level (SPL) reduced, usually measured in decibels (dB), is typically depicted graphically as a function of frequency. Most hearing protection fails to deliver a flat attenuation across frequency spectrum, instead typically providing attenuation which increases in dB as frequency increases; therefore, the attenuation spectrum is typically nonlinear, which affects the perception of sound frequencies across the audible spectrum in different degrees. For this reason, pitch perception and other auditory experiences which rely on frequency-based cues can be compromised by the nonlinear attenuation imparted by conventional hearing protectors. This leads to the need for uniform or "flat" attenuation, which is desirable in many situations, for example, musicians would like to conserve their hearing while hearing an accurate frequency representation of the produced music, or workers who must listen for certain spectral characteristics associated with their machinery or environment. Ferrofluids are composed of nanoscale particles (diameter usually 10 nanometers or less) of magnetite, hematite or some other compound containing iron. This is small enough for thermal agitation to disperse them evenly within a carrier fluid, and for them to contribute to the overall magnetic response of the fluid. This is analogous to the way that the ions in an aqueous paramagnetic salt solution (such as an aqueous solution of copper(II) sulfate or manganese(II) chloride) make the solution paramagnetic.

Particles in ferrofluids are dispersed in a liquid, often using a surfactant, and thus ferrofluids are colloidal suspensions—materials with properties of more than one state of matter. In this case, the two states of matter are the solid metal and liquid it is in. This ability to change phases with the application of a magnetic field allows them to be used as seals, lubricants, and may open up further applications in future nanoelectromechanical systems.

True ferrofluids are stable. This means that the solid particles do not agglomerate or phase separate even in extremely strong magnetic fields. However, the surfactant tends to break down over time (a few years), and eventually the nano-particles will agglomerate, and they will separate out and no longer contribute to the fluid's magnetic response.

The term magnetorheological fluid (MRF) refers to liquids similar to ferrofluids (FF) that solidify in the presence of a magnetic field.

Magnetorheological fluids have micrometre scale magnetic particles that are one to three orders of magnitude larger than those of ferrofluids.

However, ferrofluids lose their magnetic properties at sufficiently high temperatures, known as the Curie temperature. The specific temperature required varies depending on the specific compounds used for the nano-particles.

Electrorheological (ER) fluids are suspensions of extremely fine non-conducting particles (up to 50 micrometres diameter) in an electrically insulating fluid. The apparent viscosity of these fluids changes reversibly by an order of up to 100,000 in response to an electric field. For example, a typical ER fluid can go from the consistency of a liquid to that of a gel, and back, with response times on the order of milliseconds. The change in apparent viscosity is dependent on the applied electric field, i.e. the potential divided by the distance between the plates. The change is not a simple change in viscosity, hence these fluids are now known as ER fluids, rather than by the older term Electro Viscous fluids. The effect is better described as an electric field dependent shear yield stress. When activated an ER fluid behaves as a Bingham plastic (a type of viscoelastic material), with a yield point which is determined by the electric field strength. After the yield point is reached, the fluid shears as a fluid, i.e. the incremental shear stress is proportional to the rate of shear (in a Newtonian fluid there is no yield point and stress is directly proportional to shear). Hence the resistance to motion of the fluid can be controlled by adjusting the applied electric field.

One of the current issues with hearing protection and hearing assistance systems is that the attenuation cannot be tuned for a particular situation.

BRIEF DESCRIPTION OF THE DRAWINGS

Exemplary embodiments of present invention will become more fully understood from the detailed description and the accompanying drawings, wherein:

FIG. 1 illustrates a cartilaginous region and a bony region of an ear canal;

FIG. 2 illustrates general physiology of an ear;

FIG. 3 illustrates a nonlimiting example of an experiment for determining material properties of inflatable elements;

FIGS. 13-18 illustrate non-limiting examples of earplugs with modifiable attenuation;

FIG. 20 illustrates a lanyard earplug system in accordance with at least one exemplary embodiment;

FIG. 23A is a schematic diagram illustrating non-limiting example of earplugs with modifiable attenuation;

FIG. 23B is a schematic diagram illustrating non-limiting example of earplugs with modifiable attenuation;

FIG. 24 illustrates cross section of an acoustic shaping panel in accordance with at least one exemplary embodiment;

FIGS. 25A and 25B are schematic diagrams illustrating cross section of an acoustic shaping panel in accordance with at least one exemplary embodiment;

FIG. 27 illustrates an acoustic shaping panel in accordance with at least one exemplary embodiment;

FIG. 28 illustrates a cross section of the panel illustrated in FIG. 27;

FIG. 29 illustrates attachment of the panels of FIG. 27 on a wall in accordance with at least one exemplary embodiment;

FIG. 30A illustrates cross section of an acoustic shaping panel in accordance with at least one exemplary embodiment;

FIG. 30B illustrates a close-up of the medium illustrated in FIG. 30A;

FIGS. 31A, 31B, 31C, and 31D illustrate variations of cross sections of acoustic shaping panels in accordance with various exemplary embodiments;

FIGS. 34A, 34B, and 34C illustrate the configuration and operation of at least one exemplary embodiment;

FIGS. 35A, 35B, 35C, and 36 illustrate the configuration and operation of at least one exemplary embodiment;

FIGS. 37 and 38 illustrate a helmet with a liner in accordance with at least one exemplary embodiment;

FIGS. 39-40 illustrates various flexible distal ends developed;

FIG. 41 illustrates a novel distal end spiral feed system which enhances uniform expansion about a stent;

FIG. 49 illustrate an inflatable earphone system in accordance with one exemplary embodiment;

FIGS. 50-51 illustrate a lanyard pump inflatable earphone system;

FIGS. 52-53 illustrate an actuatable inflatable earphone system;

FIGS. 54A, 54B, 55 illustrate pull-release expandable earphone system;

FIG. 62 is a block diagram of a method for occluding or partially occluding an ear canal with an ear device in accordance with an example embodiment;

FIG. 64 is a block diagram of a method for occluding or partially occluding an ear canal with a chamber of an ear device in accordance with an example embodiment;

FIGS. 65A and 65B illustrate the use of a rotating member to open a valve in an ear device; and FIG. 66 is a cutaway view of a molded ear device without a stop flange in accordance with an example embodiment.

DETAILED DESCRIPTION OF EXEMPLARY EMBODIMENTS

Figure 4:
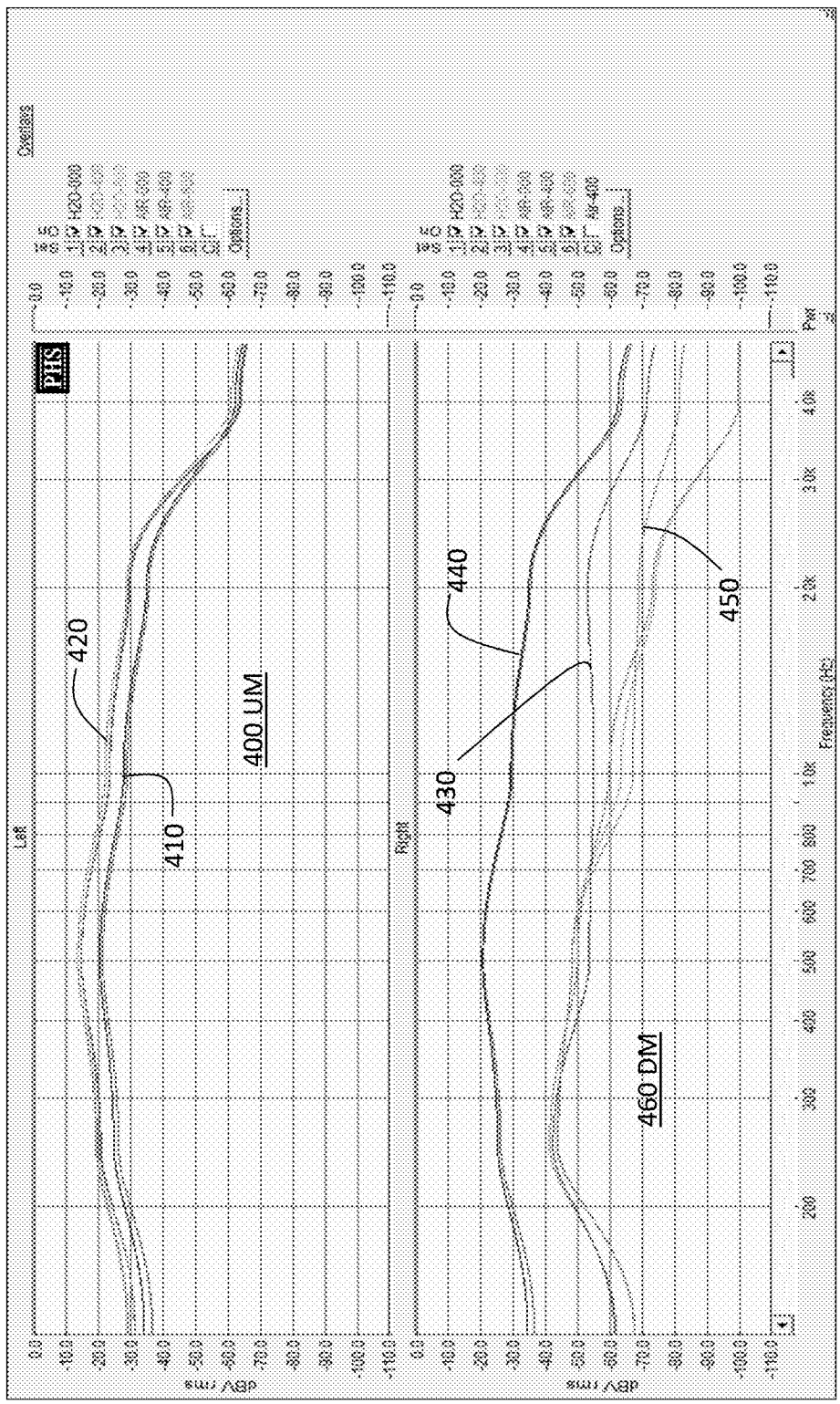
FIG. 4 illustrates the sound pressure levels (SPL) of the upstream microphone (UM) and the downstream microphone (DM) as a function of medium and pressure.

The following description of exemplary embodiment(s) is merely illustrative in nature and is in no way intended to limit the invention, its application, or uses.

Exemplary embodiments are directed to or can be operatively used on various passive earplugs for hearing protection or electronic wired or wireless earpiece devices (e.g., hearing aids, ear monitors, earbuds, headphones, ear terminal, behind the ear devices or other acoustic devices as known by one of ordinary skill, and equivalents). For example, the earpieces can be without transducers (for a noise attenuation application in a hearing protective earplug) or one or more transducers (e.g. ambient sound microphone (ASM), ear canal microphone (ECM), ear canal receiver (ECR)) for monitoring/providing sound. In all of the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

FIG. 1 illustrates a generic cross section of an ear canal 100, including a cartilaginous region 140 and a bony region 130 of an ear canal 120. The entrance of the ear canal 120 is referred to as the aperture 150 and defines a first end of the ear canal while the tympanic membrane 110 defines the other end of the ear canal 120.

FIG. 2 illustrates general outer physiology of an ear, which includes a, auricle tubercle 210, the antihelix 220, the helix 230, the antitragus 240, tragus 250, lobule of ear 260, crus of helix 270, anterior notch 280, and intertragic incisures 290.

FIG. 3 illustrates a nonlimiting example of an experiment for determining material properties of inflatable elements. To isolate the variations in ear canal lengths, ear canal cross sections and insertion depths of earpieces (e.g., earplugs, in-the-canal hearing aids) an experimental setup 300 was constructed as illustrated in FIG. 3. A noise source 310 (e.g., Phonic PAA6) generates acoustic source waves 315 (e.g., pink noise, white noise) which travel down an acoustic tube 320A where the incident acoustic signal is measured by an upstream first microphone (e.g., M1 or UM, Audix Measurement Microphone). The test sample 330 (e.g., balloon, isolated chamber) can be filled with various fluids (e.g., air, water, water with agents) and inserted into a portion 320B of the tunnel such that the acoustic source waves impinge one side of the test sample, travels through the test sample, and exit the opposite or adjacent (not shown) side of the test sample, where a downstream microphone (e.g., M2 or DM) measures the exiting acoustic waves. To minimize reflections from the end of the downstream tube the system is set to have an anechoically terminated end, which is accomplished by length (>75 ft) so as to gradually diminish the energy of the travelling wave 316 via wall interaction, and by having small strands of string near the end to absorb more of the energy in the wave. The data from the two microphones M1 and M2 are obtained to extract acoustical spectrum information (e.g., using FFT analyzer software such as 340 Spectra-PLUS™ FFT Analyzer). For example, when measuring insertion loss (IL), measurements are taken with M2 prior to insertion of a test sample, then a test sample inserted and measurements retaken with M2. Using the same sound source in both measurements, the difference in the two measurements is defined as insertion loss (IL). For discussion herein with regards to tunnel data IL is approximated when using balloons by a difference in the uninflated M2 measurements (i.e. pressure of 000 mbar gauge pressure) and an inflated M2 measurement. The pressure of a test sample is varied by use of a pressure pump 350 (e.g., SI Pressure LTP1™ Low Pressure Calibration Pump), and monitored by reading the pressure from a pressure gauge 360 (e.g., Extech™ Differential Pressure Manometer).

Figure 11:
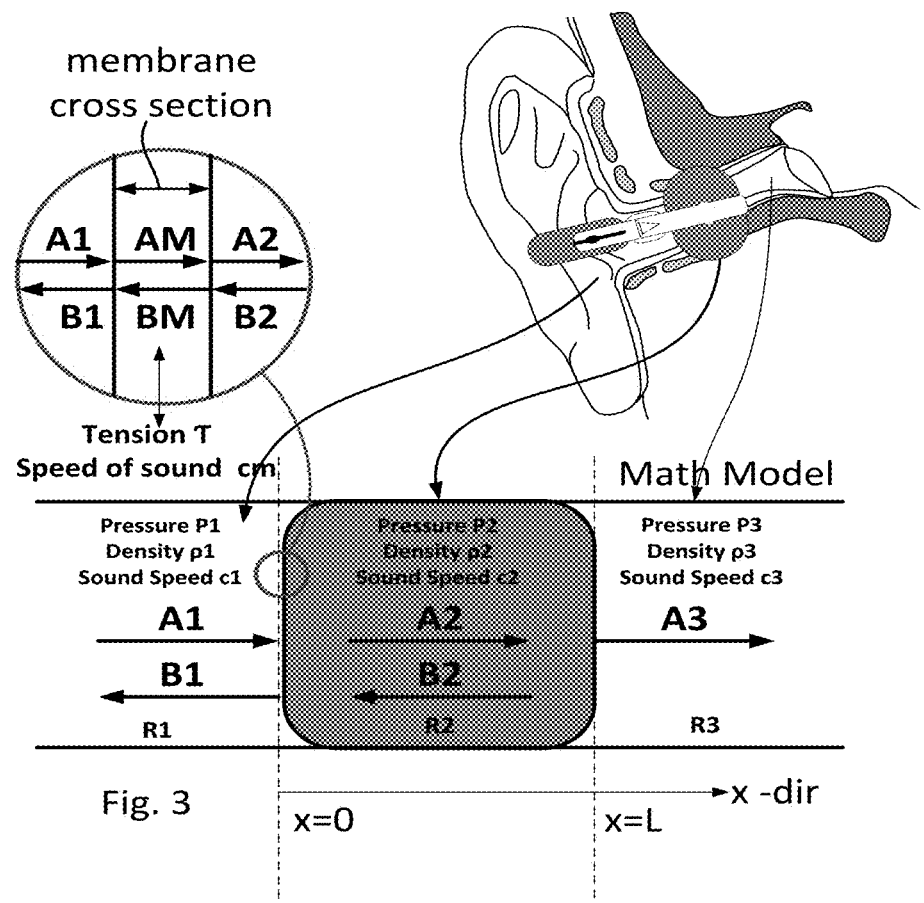
FIG. 11 illustrates a general mathematical model of an earplug using a membrane.
Figure 12:
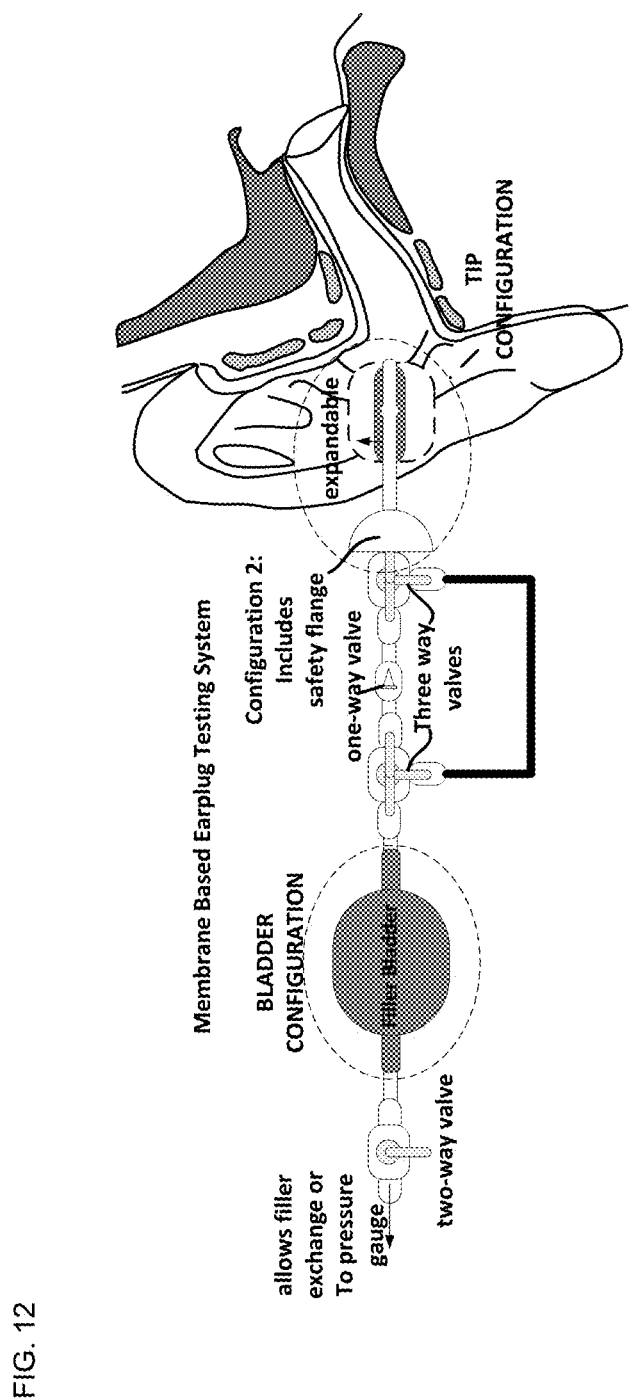
FIG. 12 illustrates an experimental test system that can be used to test attenuation and reflection characteristics both in a subject and for panel design.
Figure 16:
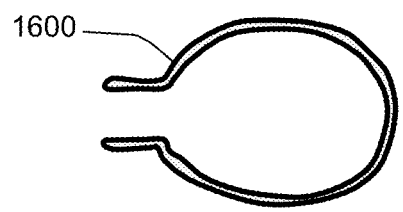

FIG. 4 illustrates the sound pressure levels (SPL) of the upstream microphone (UM) and the downstream microphone (DM) as a function of medium and pressure. dB Values rms between water and air at 000 mbar, 400 mbar, and 600 mbar gauge pressure are illustrated. A larger value indicates higher SPL values, thus a value of −10 dB is an increase of 20 dB in SPL value from −30 dB. Note that the values for 000 mbar represent the uninflated value and the insertion loss (IL) can be obtained by subtracting the 000 mbar value from the pressure values for the downstream microphone (DM). IL values are presented on the next plot (FIG. 5); note also that the plotting values are 1-octave values and hence have been averaged from the narrowband data, thus details in the narrow band data are lost. However the 1-octave values allow more direct comparison to human subject data (FIGS. 11 and 12).

The top panel illustrates upstream microphone 400 (UM) measurements under six conditions, water as the medium under three pressures: 000 mbar (blue), 400 mbar (green), and 600 mbar (light blue); and air as the medium under the same three pressures: 000 mbar (light purple), 400 mbar (red), and 600 mbar (orange). Note that the pressure conditions separate into two general separate lines, the first with no inflation for example 410, and a second line where the two non-zero pressure values generally overlap into a single line 420. Thus generally independent of pressure in the sample, an increase of about 7 dB is measured upstream of the test sample. One possible interpretation is that 7 dB of incident energy is reflected from the interface.

The bottom panel illustrates downstream microphone 460 (DM) measurements under six conditions, water as the medium under three pressures: 000 mbar (blue), 400 mbar (green), and 600 mbar (light blue); and air as the medium under the same three pressures: 000 mbar (light purple), 400 mbar (red), and 600 mbar (orange). Note that the pressure conditions separate into two general regions, the first region is associated with no inflation 440 where irrespective of medium, as one might expect, the lines overlap. The other region varies depending upon medium and pressure. For example, a red line marks dB values for air at 440 mbar and the orange line dB values for 600 mbar. In general as the pressure increases the rms dB value decreases in value as measured by DM. Note that between a frequency of 300-700

Hz an increase in pressure is not associated with an decrease measured value at DM. Note that both UM and DM measurements have roughly a frequency independent standard deviation of <0.2 dB.

Figure 5:
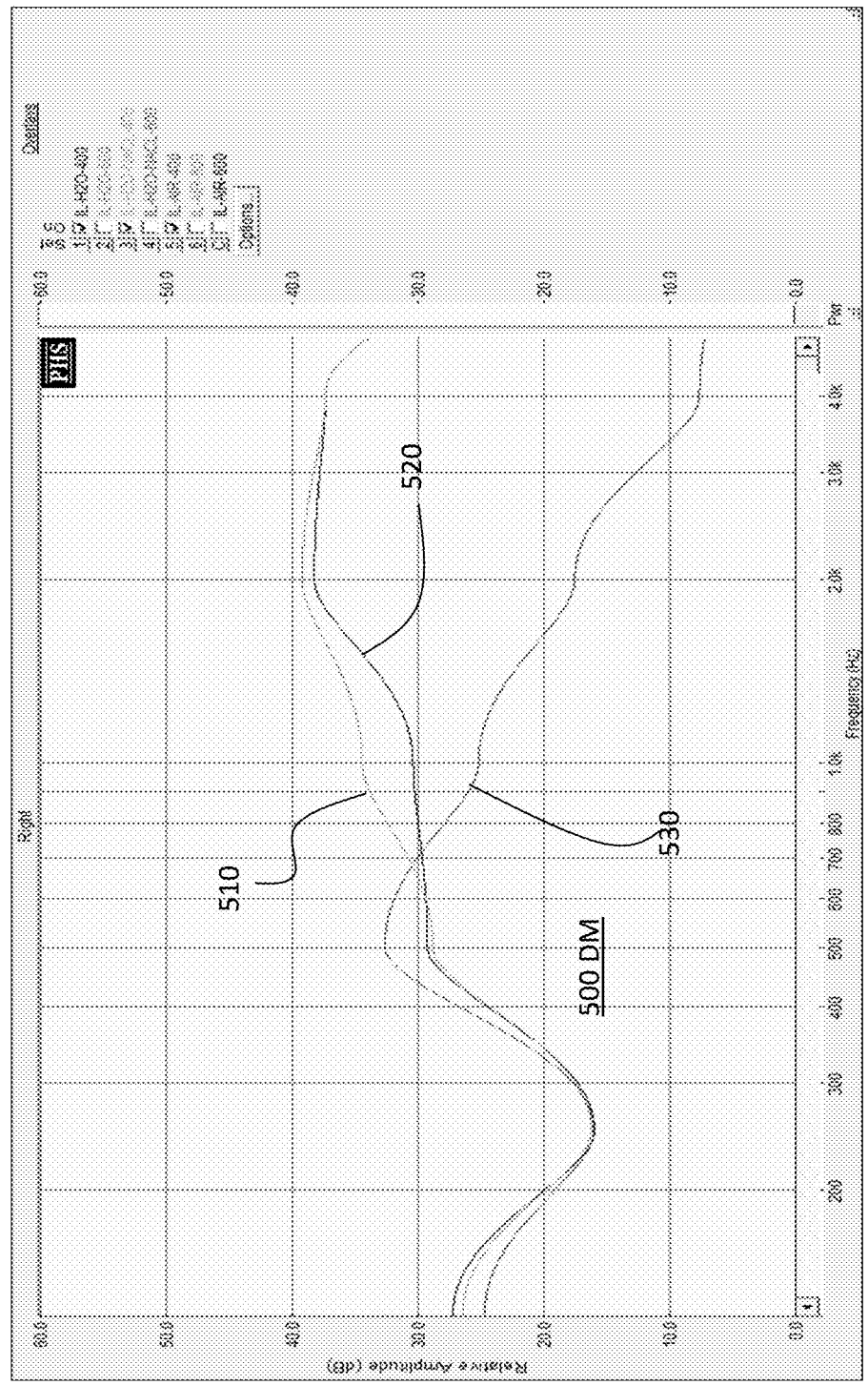
FIG. 5 illustrates the insertion loss (IL) value for three mediums, NaCl, H2O, and Air at 400 mbar gauge pressure.

FIG. 5 illustrates the insertion loss (IL) values 500 for three mediums, NaCl, H2O, and Air at 400 mbar gauge pressure as measured by the downstream microphone DM. Note that a larger IL value is associated with more energy being removed from the initial acoustic wave by the test sample. As illustrated the three different mediums, distilled $H_2O$ with 1.95 mg/L NaCl (light blue line) 510, distilled $H_2O$ (blue) 520, and Air (red) 530, are distinguishable. For example air provides less IL after 700 Hz than $H_2O$ 520 and $H_2O$+NaCl mixture 510. Note that $H_2O$ 520 and $H_2O$+NaCl mixture 510 have similar profiles below 700 Hz and above 3 kHz. Between 700 Hz-3 KHz the IL values 510 and 520 differ such that an $H_2O$+NaCl mixture provides more IL. Note that although an $H_2O$+NaCl mixture is illustrated, other mixtures (e.g., with sucrose, alcohol, mineral oil) can be used to taylor specific increases or decreases in IL as a function of frequency for a given pressure.

Figure 6:
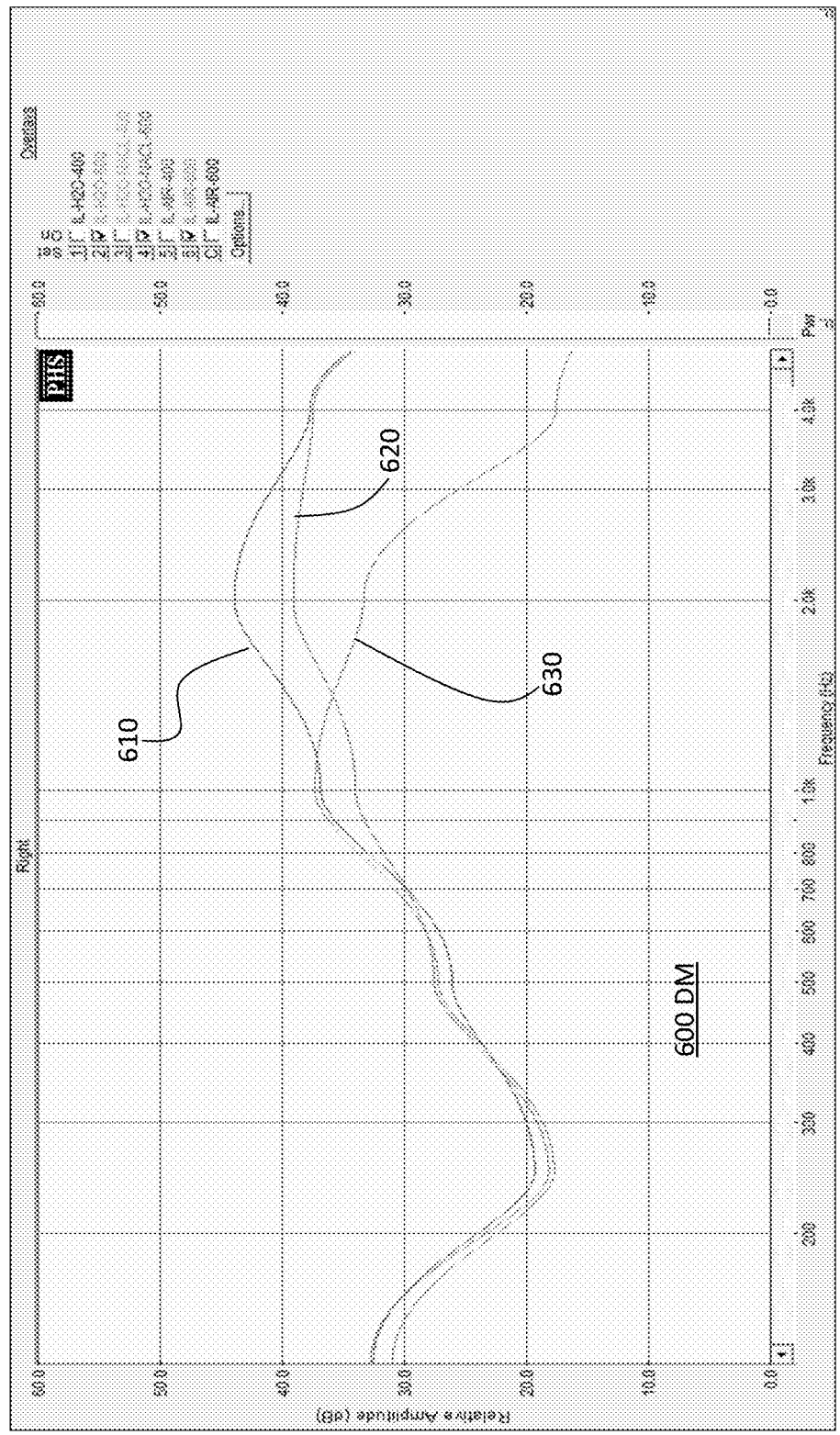
FIG. 6 illustrates the insertion loss (IL) value for three mediums, NaCl, H2O, and Air at 600 mbar gauge pressure.

FIG. 6 illustrates the insertion loss (IL) values 600 for three mediums, NaCl, H2O, and Air at 600 mbar gauge pressure as measured by the downstream microphone DM. Note that a larger IL value is associated with more energy being removed from the initial acoustic wave by the test sample. As illustrated the three different mediums distilled $H_2O$ with 1.95 mg/L NaCl (light blue line) 610, distilled $H_2O$ (blue) 620, and Air (red) 630 are distinguishable. For example air provides less IL after about 1.5 kHz than $H_2O$ 620 and $H_2O$+NaCl mixture 610. Note that the decrease with air as a medium after 1.5 kHz differs from the 400 mbar value of 700 Hz. Thus at increased pressures air 630 provides less IL than $H_2O$ 620 and $H_2O$+NaCl mixture 610 above a higher frequency. Thus generally as the test sample pressure is increased, the IL profiles also vary, facilitating using controllable pressure values to obtain design IL profiles. For example, if an earplug uses air and an IL value above 700 Hz in unimportant for the particular use, then an earplug can be designed to have an internal balloon pressure of about 400 mbar, whereas if the IL value above 1.5 kHz is unimportant then the earplug balloon can be designed to have an internal pressure of 600 mbar.

Note that $H_2O$ 620 (green) and $H_2O$+NaCl mixture 610 (red) have similar profiles up to about 700 Hz. Above 700 Hz, the IL values 610 and 620 differ such that an $H_2O$+NaCl mixture provides more IL. Note that although an $H_2O$+NaCl mixture is illustrated, other mixtures (e.g., with sucrose, alcohol, mineral oil) can be used to tailor specific increases or decreases in IL as a function of frequency for a given pressure. Thus, if an earplug is designed for use with distilled water, the IL value can be varied at different frequencies by adding agents (e.g., NaCl). If one wishes to increase the IL above 700 Hz one could add a mixture of NaCl and distilled water 620.

Figure 7:
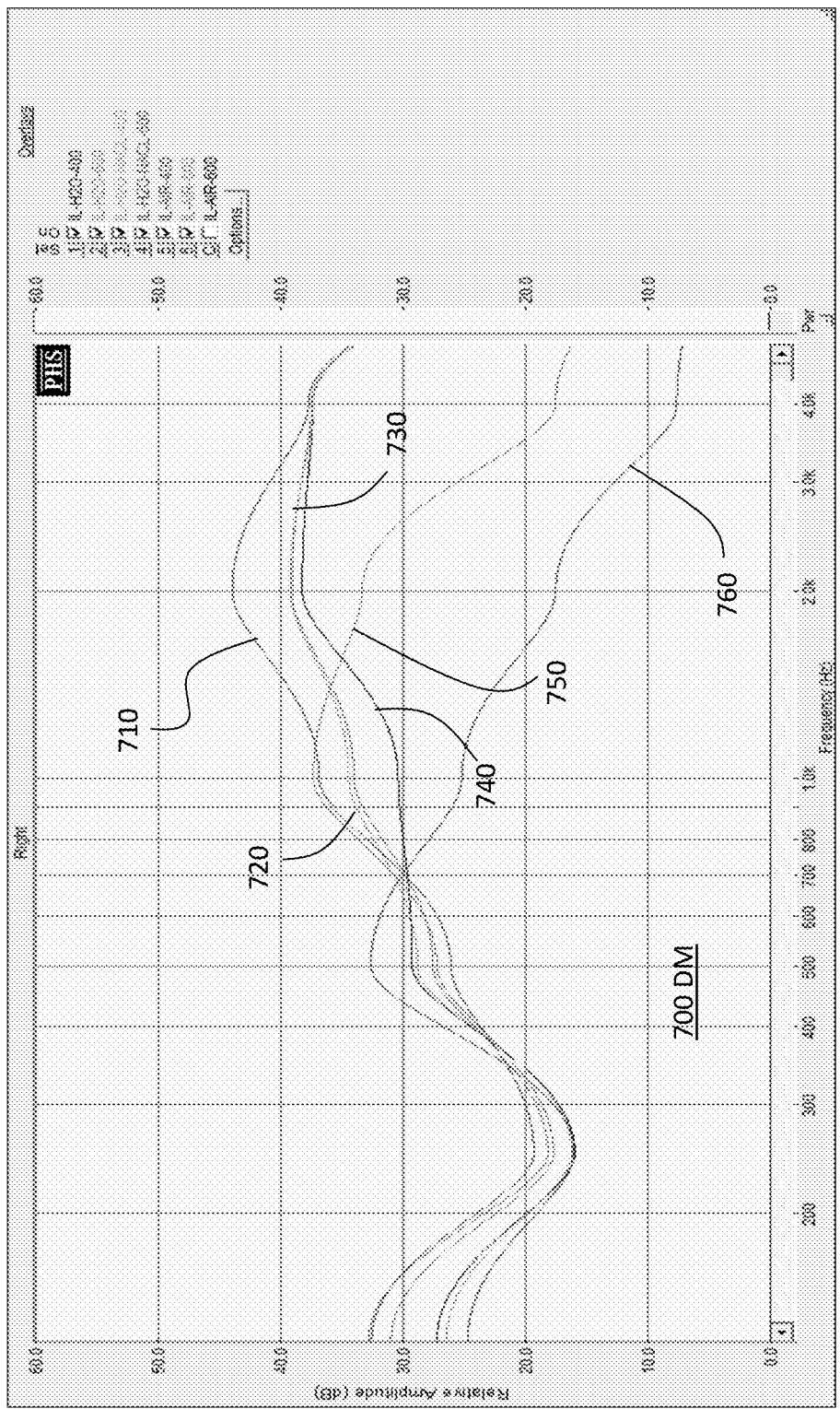
FIG. 7 illustrates the insertion loss (IL) value for three mediums, NaCl, H2O, and Air for 400 mbar and 600 mbar gauge pressures.

FIG. 7 illustrates the insertion loss (IL) value 700 for three mediums, NaCl, $H_2O$, and Air for two pressures 400 mbar and 600 mbar gauge pressures as illustrated in FIGS. 5 and 6 for ease of comparison.

Figure 8:
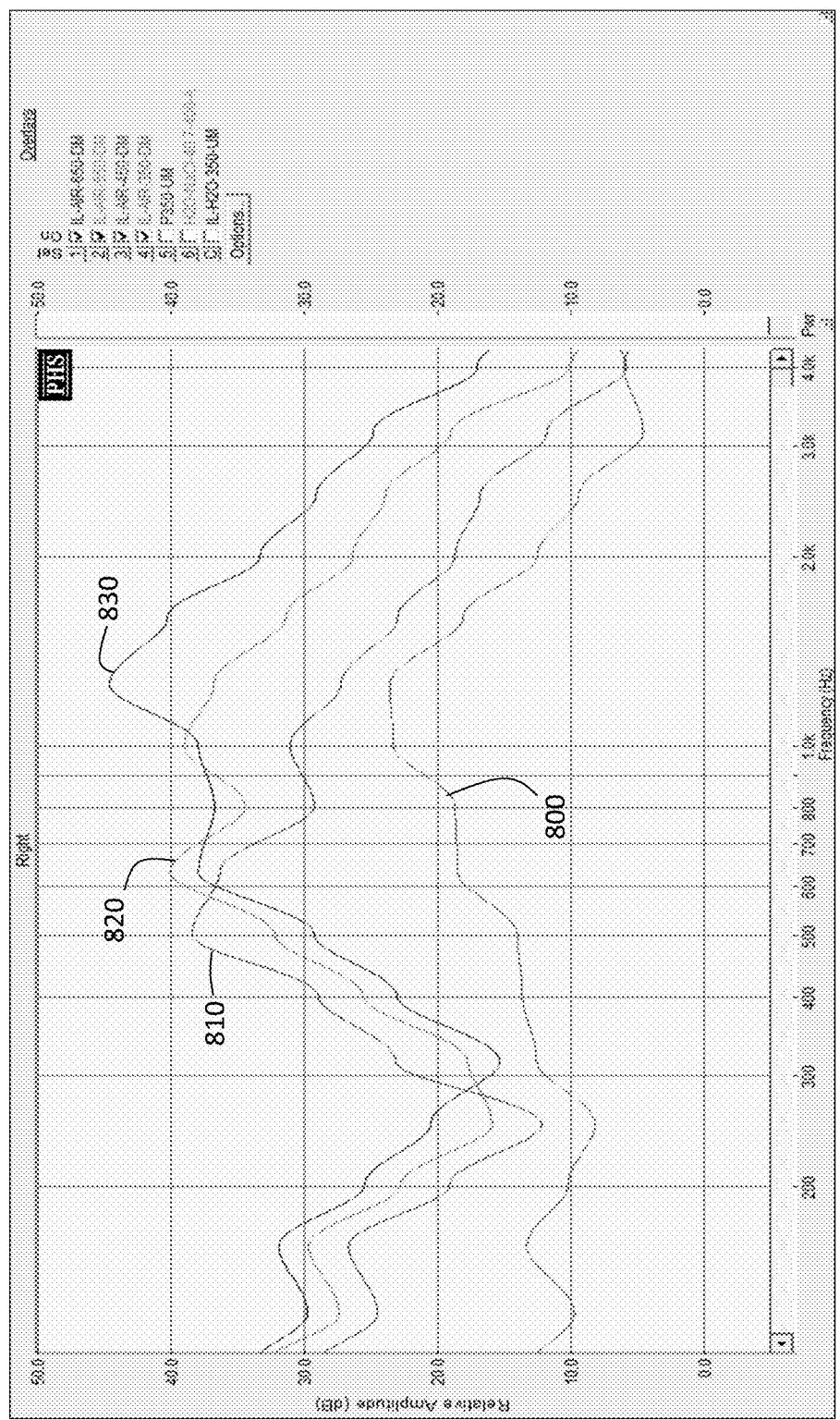
FIG. 8 illustrates the insertion loss (IL) value for Air for gauge pressures of 350 mbar, 450 mbar, 550 mbar, and 650 mbar gauge pressures.

FIG. 8 illustrates the insertion loss (IL) value for Air for gauge pressures of 350 mbar (800), 450 mbar (810), 550 mbar (820), and 650 mbar (830) gauge pressures. In general as the pressure of a test sample increases the IL value increases for frequencies less than about 300 Hz and greater than about 1 kHz. Between about 300 Hz and 1 kHz the pressure with the larger IL depends upon frequency. For example, a pressure of 450 mbar has a larger IL value than other pressures at about 500 Hz, while a pressure of 550 mbar has the largest IL value at about 650 Hz. Thus pressure can be varied in an earplug device to modify the frequency at which the greatest IL is provided. For example, suppose the frequency of an offending noise source gradually increases in frequency. An air-filled earplug with interactive pressure control could increase the pressure of an earplug balloon to maintain suppression of the noise source as its frequency increased.

Figure 9:
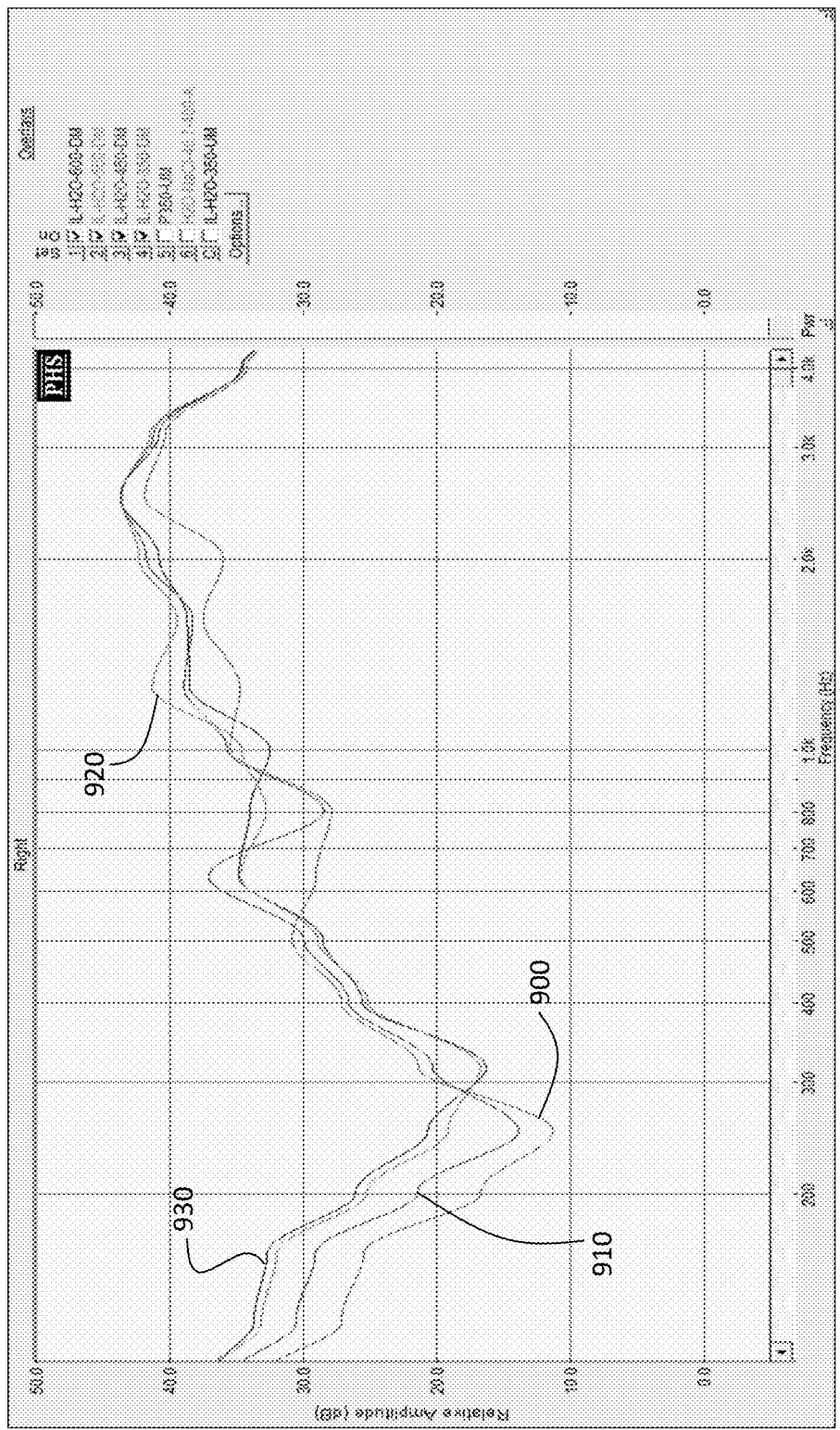
FIG. 9 illustrates the insertion loss (IL) value for H2O for gauge pressures of 350 mbar, 450 mbar, 550 mbar, and 600 mbar gauge pressures.

FIG. 9 illustrates the insertion loss (IL) value for $H_2O$ for gauge pressures of 350 mbar (900), 450 mbar (910), 550 mbar (920), and 600 mbar (930) gauge pressures. In general as the pressure of a test sample increases the IL value increases for frequencies less than about 300 Hz. Above about 300 Hz the pressure with the larger IL depends upon frequency. For example a pressure of 450 mbar has a larger IL value than other pressures at about 625 Hz, while a pressure of 550 mbar has the largest IL value at about 1.25 kHz. Thus pressure can be varied in an earplug device to modify the frequency at which the greatest IL is provided. For example, suppose a flatter frequency dependent IL is desired between frequencies of about 500 Hz and 800 Hz, then the pressure of an $H_2O$ filled earplug bladder can be set to about 350 mbar and if an increase of IL is needed within this range then the pressure can be increased.

Figure 10:
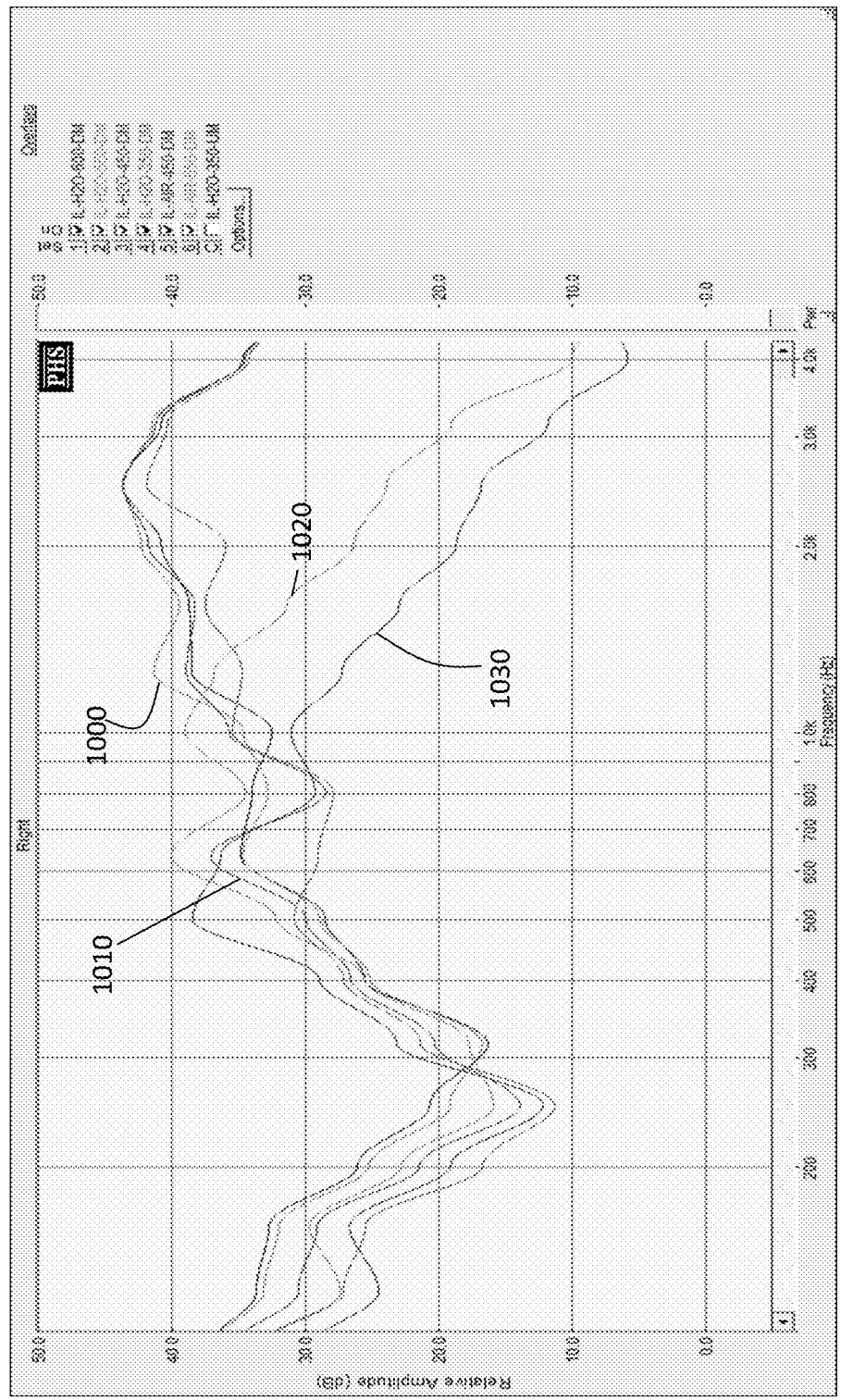
FIG. 10 illustrates the insertion loss (IL) value for two mediums, H2O, and Air for 450 mbar and 550 mbar gauge pressures.

FIG. 10 illustrates the insertion loss (IL) value for the $H_2O$ values of FIG. 9 and two air values for comparison Air at 450 mbar (1030) and 550 mbar (1020) gauge pressures. Note that peak IL values differ from the fluid used (e.g., air or $H_2O$). For example, if an earplug device is designed to maximize IL at 500 Hz, then one can use air at 450 mbar, where if one wishes to maximize the IL at about 650 Hz the air pressure can be increased to 550 mbar. If one wishes to design an earplug to maximize IL at about 1.25 kHz then one can use $H_2O$ at a pressure of about 550 mbar. Note that a flatter IL profile when using $H_2O$ can be obtain between frequencies about 500 Hz and 1 kHz by setting the $H_2O$ pressure to about 550 mbar as opposed to 450 mbar.

The extent of the earplug can be modeled as a region extending from x=0 to x=L with an incident pressure wave A1 (FIG. 11). The reflectance of the pressure wave and transmission of the pressure wave will depend upon the impedance (Z=ρc) between two regions. The membrane itself can also be considered a region separating region 1 and region 2. Between two regions the Reflection (R) coefficient and Transmission (T) coefficient can be derived using interface boundary conditions BC1 (continuity of pressure) and BC2 (continuity of particle velocity).

$$A1+B1=A2+B2 \text{ (continuity of pressure)} \quad (1)$$

$$A1-B1=(Z1/Z2)(A2-B2) \text{ (continuity of particle velocity)} \quad (2)$$

Note that equations (1) and (2) are generally used across any boundary between two regions. If we treat the membrane as the second region we will get the relationships:

$$A1+B1=AM+BM \text{ (continuity of pressure)} \quad (3)$$

$$A1-B1=(Z1/ZM)(AM-BM) \text{ (continuity of particle velocity)} \quad (4)$$

For a membrane the speed of sound in the membrane, (cm), is a function of the tension force per unit length ($T_l$) and the surface density (m, mass per unit area), and can be expressed as:

$$cm=\sqrt{T_l/m} \quad (5)$$

Thus ZM can be expressed as $ZM = \rho_m\sqrt{T_f/m}$, whereas $Z1 = \rho1*c1 = (1\ Kg/m^3)(343\ m/sec,\ in\ air) = 343$, and using roughly $\rho_m = 1100\ Kg/m^3$ (for rubber) and a tension of about $T_f = (1.2\ atm*101300\ N/m^2)*(\pi)*(0.005\ m)^2/0.01\ m \approx 954\ N/m$, and $m = (1100\ Kg/m^3)*(0.0001\ m)/[(\pi)*(0.005\ m)^2] \approx 1401\ Kg/m^2$ one can obtain about $ZM \approx 907,\ldots$ so that roughly the ratio $Z1/ZM = 0.38$. Note that for a membrane earplug the filler pressure can be varied and hence the tension force can be varied. Note that a simple examination of continuity of particle velocity (2) results in:

$$A1 - B1 \approx (0.38)(AM - BM) \text{ (continuity of particle velocity)} \quad (6)$$

Thus reflectivity increases at the membrane interface (essentially B1 approaches A1). The unique aspect of membrane earplugs is that the tension can be varied by increasing the pressure in the bladder and the relative speeds of sound can be varied by changing the filler fluid. If one uses a filler fluid of water $H_2O$ as a comparison to the aforementioned air, $Z2 = (1500\ m/sec)(1000\ Kg/m^3) = 1500000$. In a more general analysis the Reflectivity coefficient (R), examining only the air-filler interface, can be reduced, for when $k2L \ll 1$ (a small membrane thickness), as:

$$R = B1/A1 \approx [(Z2 - Z1)/(Z2 + Z1)] \approx 1499657/1500343 = 0.9995 \quad (7)$$

This shows a large reflection coefficient, when the filler is $H2O$. Note that the value of Z2 is determined by the filler fluid medium and can be tailored depending upon desired attenuation performance.

At least one exemplary embodiment of the present invention employs a simple stretch membrane (i.e., "balloon") approach, wherein an inflatable, lightweight balloon is inserted into the ear canal in its deflated state, and then inflated once inside the canal. This insertion configuration affords its own additional advantages in the realm of having an in-ear product that is undersize compared to the diameter of the ear canal prior to insertion, and then expands once inside the canal, unlike most other earplug products on the market, including the Ety High Fidelity™ earplug, which are sized to be oversize the ear canal prior to insertion, and thus require squeezing or compression upon insertion, making insertion more difficult.

FIG. 12 illustrates a method for testing various configurations. The membrane-based earplug testing system comprises in general a tip configuration and a bladder configuration. The bladder configuration includes a filler bladder where the filler bladder is a medical balloon that is pre-shaped but deformable. The tip configuration includes a compliant tip that is an expandable elastic medical balloon that conforms to a stent. The stent connects the filler bladder to the compliant tip. The filler bladder can be deformed forcing filler material to the compliant tip which expands to fill an ear canal. The material is kept from flowing back to the filler bladder by a deformable one way valve. The deformable one-way valve (made of compliant rubber-like material) can be deformed by a user to allow back flow to the bladder. The system additionally includes two way and three way valves for the relief of pressure, filler exchange, and pressure measurement. The one way valve, two way valve, and three way valves are valves that can be included in housing, with attached medical luer locks that can then be fitted to the stent. In one of the test configurations the tip configuration includes a safety flange to determine whether inclusion of a safety flange affects localization. Likewise the bladder configuration includes a medical pre-shaped balloon of about 1 cc volume attached to luer lock connectors at either end. Various fillers can be used for example H2O, H2O+NaCl, H2O+Alcohol, Alcohol, MR fluid, and Air, note that this list is a non-limiting example only.

FIGS. 13-18 illustrate non-limiting examples of earplugs with modifiable attenuation. FIG. 13 illustrates an earpiece (e.g., earplug, headphone, hearing aid) that includes a first reservoir 1310 (e.g., Urethane balloon, silicon balloon) fed by a channel (tube) 1330 in a stent 1300. The stent 1300 can be fabricated from various materials (e.g., silicon, urethane, rubber) and can include internal channel (tubes), for example tubes 1330 and 1320. The stent can also be a multi-lumen (i.e., multi-passageway) stent where the channels/tubes are various lumens of the multi-lumen stent. The first reservoir 1310 can be connected to a second reservoir 1370 via the tube 1330. Thus a fluid 1360 can be transferred between the first reservoir 1310 and the second reservoir 1370 by pressing against the second reservoir 1370 or by pressing against the first reservoir 1310. Additionally the reservoirs (1370 and 1310) can be fabricated from stressed membranes (e.g., silicone) so that when fluid is inserted into the reservoirs a restoring force presses against the fluid 1360 by the membrane. For example if the second reservoir was fabricated from a compliant balloon with an initial state of collapse, then filling the second reservoir 1370 with fluid 1360 would stretch the membrane such that the membrane would seek to press against the fluid 1360. If the first reservoir restoring force caused by its membrane is less than that of the second reservoir 1370 then the fluid 1360 will move via tube 1330 into the first reservoir. Alternatively a structure can press against the second reservoir 1370 pushing against the fluid 1360 moving a portion of the fluid in to the first reservoir. FIG. 13 illustrates a non-limiting example of a structure that includes a piston head 1380, a front surface of the piston head 1390 connected to a stem 1384. The structure can lie within a housing that has optional internal threads 1382, which optional threads on piston head 1380 can engage so if one rotates the piston head one pushes the piston head front surface against the second reservoir 1370.

Note that in at least one exemplary embodiment the restoring force of the first reservoir 1310 can be such that the fluid remains in the second reservoir 1370 unless the volume of the second reservoir 1370 is decreased. Such a configuration can be used for an earplug where the portion to be inserted is collapsed into a minimal profile shape and upon insertion a user can move the structure so that the volume of the second reservoir 1370 decreases increasing the fluid in to the first reservoir, such that the first reservoir 1310 expands occluding a channel (e.g., ear canal) into which the earpiece is at least partially placed. Note that other channels can be used to convey acoustical energy across the first reservoir, for example the tube 1320 can be used to measure or emit sound to the left of the first reservoir as illustrated in FIG. 13.

FIG. 14 illustrates a non-limiting example of a moveable structure discussed with reference to FIG. 13, where the stem 1384 is attached to a tab 1400 that a user can move (e.g., push, rotate) to move the structure toward or away from the second reservoir 1370.

FIG. 15 illustrates an isolated view of the stent discussed with reference to FIG. 13. Note that for ease of manufacturing the stent can be similar to that used in an infant urology Foley catheter, which has an inflation tube 1330 and a flush tube 1320, where for an earplug the flush tube is sealed, for example by injecting a flexible curing material (e.g., Alumilite Flex 40™ casting rubber).

Figure 17:
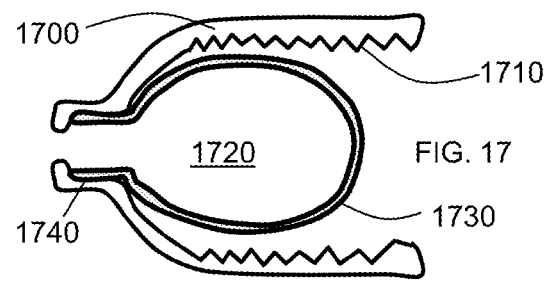
Figure 18:
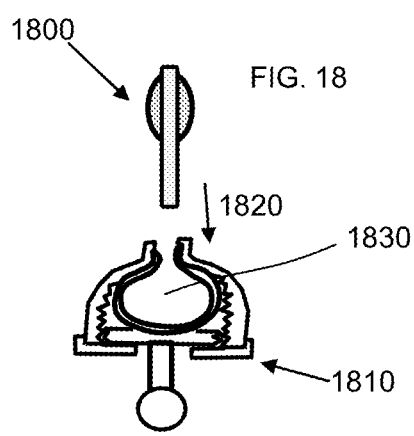

A bladder 1600 (FIG. 16) having a preformed shape (e.g., non-compliant medical balloon) or flexible shape (e.g. compliant medical balloon) can be filled with the desired fluid then attached to the stent or to the housing and sealed (FIG. 17). The bladder 1730 can be attached 1740 to housing 1700 that can also include threads 1710. The fluid filled 1830 housing 1810 (FIG. 18) (e.g., fabricated from a plastic, hard rubber) can then be attached 1820 to the stent 1800, the structure screwed into threads in the housing, and a retainer cap 1395 attached to the housing (e.g., via loctite glue) restricting the movement of the structure. Note that there can be a hole in the retainer cap 1395, having a hole diameter $D_H$, where in at least one embodiment, $D_H$ can be larger than the tab 1400 width $D_F$. Note that the bladder 1600 can be of various shape for example semi-spherical, cylindrical, and can be formed by various methods such as dip molding. Note also that an optional stop ring 1350 can be used.

Figure 19:
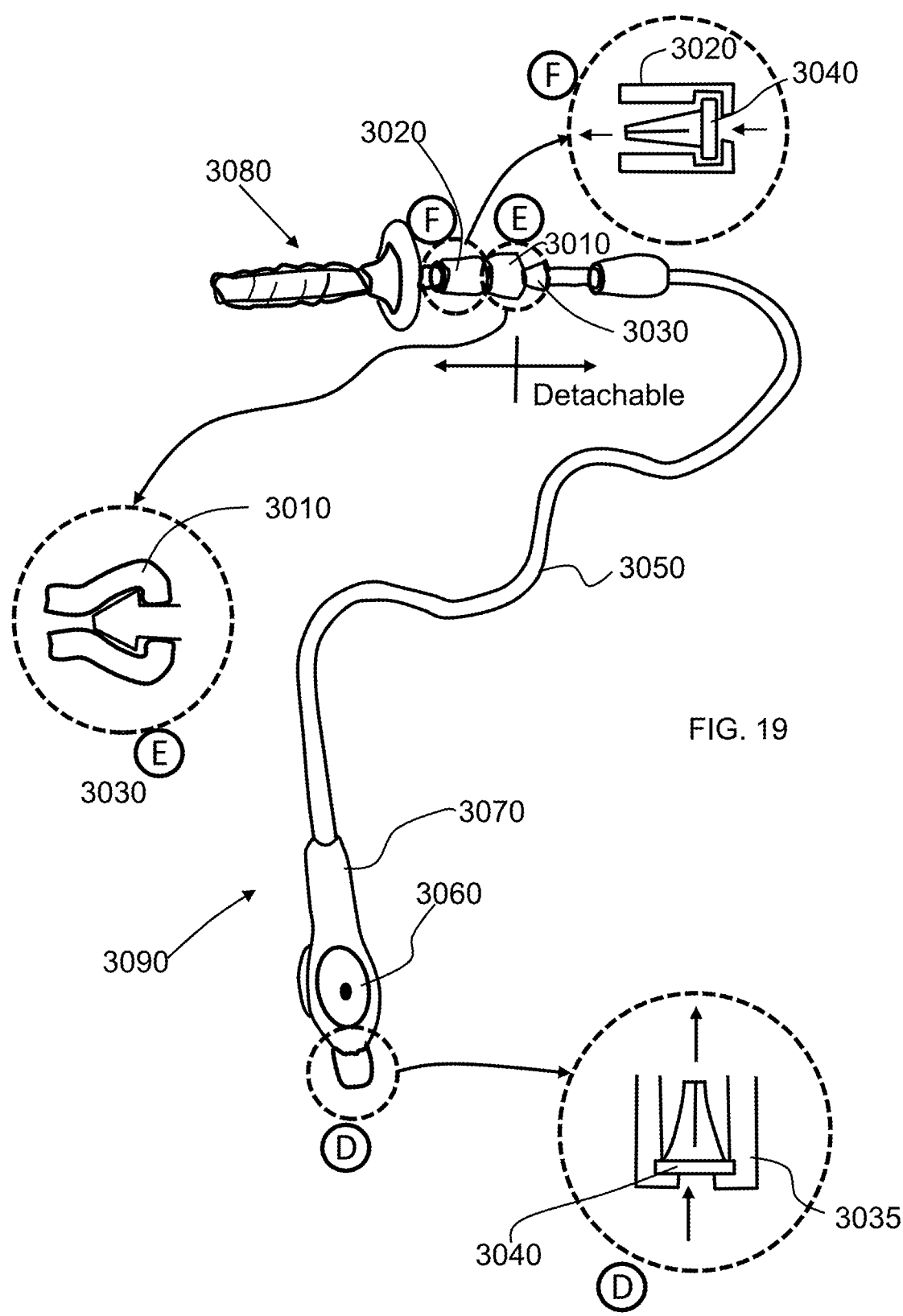
FIG. 19 illustrates a detachable earplug pumping system in accordance with at least one exemplary embodiment.

FIG. 19 illustrates a detachable earplug pumping system in accordance with at least one exemplary embodiment. The earpiece 3080 can be operatively attached via a tube 3050 to a finger pump 3090. The entire pump system (e.g., 3030, 3050, 3070, 3060, 3035) can be detachable from a pump insert port 3010. A pump seal valve 3040 in a sealing section 3020 in the earpiece 3080 generally allows one way flow and seals when the pump system is detached. The earpiece includes initially a deflated fluid reservoir which is fluid filled when the pump is actuated (e.g., finger pumped). The pump insert port 3010 allows general sealing with a detachable pumps insert interface 3030 (e.g., arrow head). The pump system can include a feed tube 3050 attached to the insert interface 3030. The feed tube can be attached to a pump body 3070 which includes a finger dimple 3060, for example fabricated from a restoring flexible material (e.g., rubber) that returns to its original shape after deformation. Thus deformation of the finger dimple 3060 forces fluid through feed tube 3050 and into the earpiece 3080. A one way valve (e.g., 3040) system 3035 feeds fluid (e.g., from the environment) into the pump body 3070 so via another deformation of the finger dimple 3060 fluid is available to be pumped into earpiece 3080.

FIG. 20 illustrates a lanyard earplug system 4060 in accordance with at least one exemplary embodiment. Earpieces 4000 including optional stop flanges 4010 can be attached to a lanyard finger pump system 4060. The lanyard finger pump system can include two connected tubes 4020A and 4020B each feeding a separate earpiece 4000. The tubes 4020A and 4020B can be connected via one way valves 4030 to a squeeze release section 4050, which can be squeezed (A) to deflate the earpieces 4000. The pump section can include a finger dimple 4040 and an inlet one way valve C. The inlet one way valve C can include a one way valve 4030. The release section 4050 can include two one way valves, one 4060A associated with tube 4020A and the other 4060B associated with tube 4020B. As fluid is pushed through each one way valve 4060A and 4060B the respective earpieces 4000 inflate. An optional one way valve per tube (not shown) can be used to make sure that the maximum pressure in each tube 4020A and 4020B does not exceed a maximum value P max.

Figure 21A:
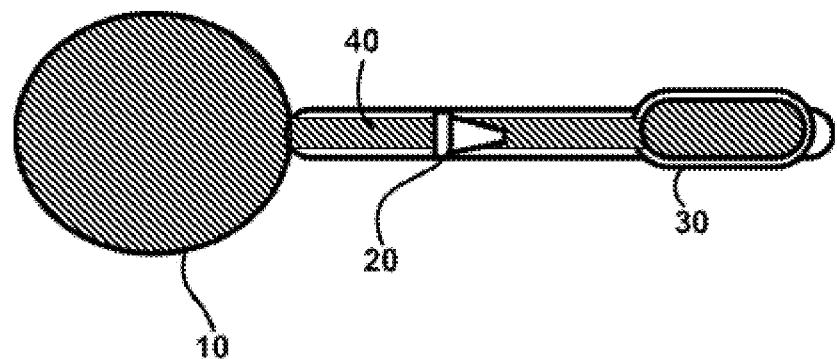
FIG. 21A is a schematic diagram illustrating non-limiting example of earplugs with modifiable attenuation.
Figure 21B:
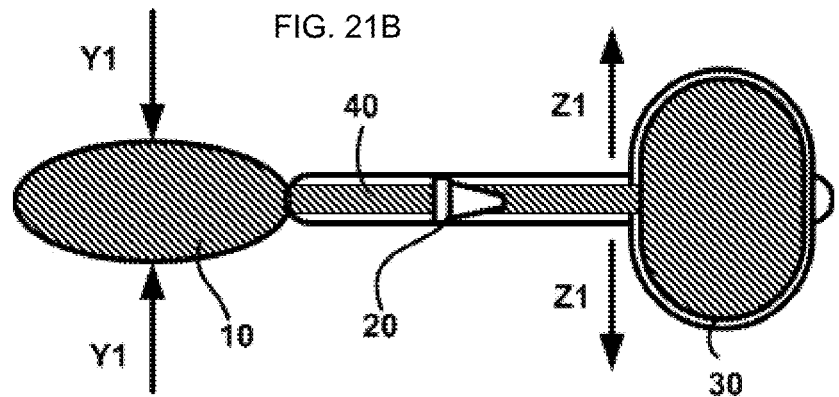
FIG. 21B is a schematic diagram illustrating non-limiting example of earplugs with modifiable attenuation.

FIGS. 21A and 21B illustrate the operation of at least one exemplary embodiment. Note that materials used for construction of earplugs, hearing aids, headphones, balloons and membranes can be used to construct exemplary embodiments used as earplugs. The device includes a reservoir 10, a fluid channel 40, a valve 20 and expandable element 30. The reservoir 10 includes a medium that can be tailored to vary the acoustic spectrum as a function of frequency. The distal end (right end of FIG. 21A) is inserted into an ear canal. The user then depresses Y1 the reservoir 10, which moves fluid from the reservoir 10 through the fluid channel 40 in a single direction as provided by the one way valve 20. The fluid movement into the expandable element 30 expands (Z1) the element 30 to a desired extent. The modification of any acoustic spectrum that passes through the earplug can be tailored (acoustically shaped) by varying the medium and pressure. Various non-limiting examples of various mediums will be discussed below, but in general can include liquids, gases, mixtures, colliodal suspensions, foams, gels, and particle suspensions. For example a colloidal suspension (e.g. aphron) can be held in suspension until mixed by a user (e.g., reservoir 10 squeezed) and a chemical reaction can occur (e.g., to generate heat to warm an earplug before insertion in cold climates).

Figure 22A:
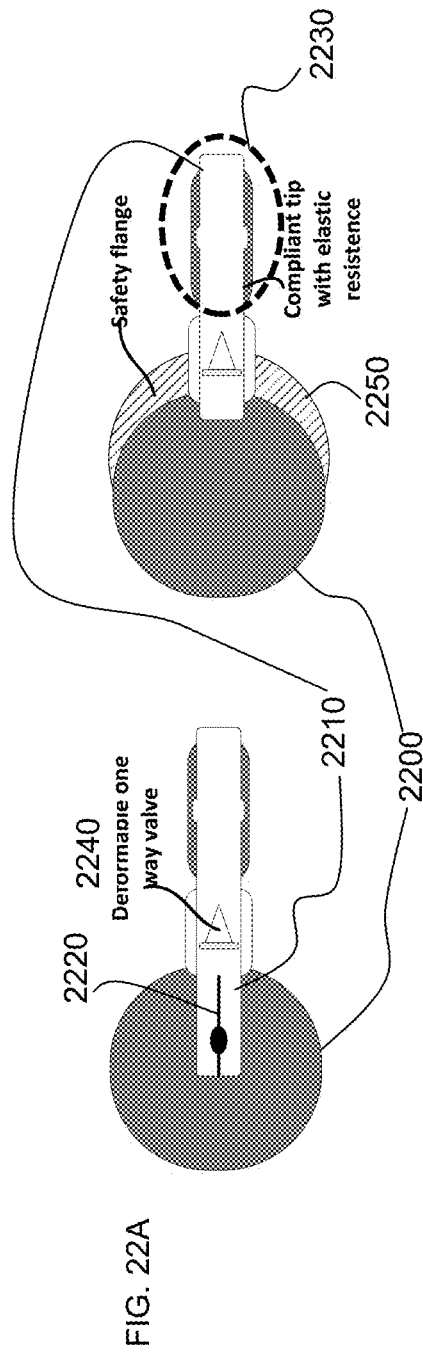
FIG. 22A is a schematic diagram illustrating non-limiting example of earplugs with modifiable attenuation.
Figure 22B:
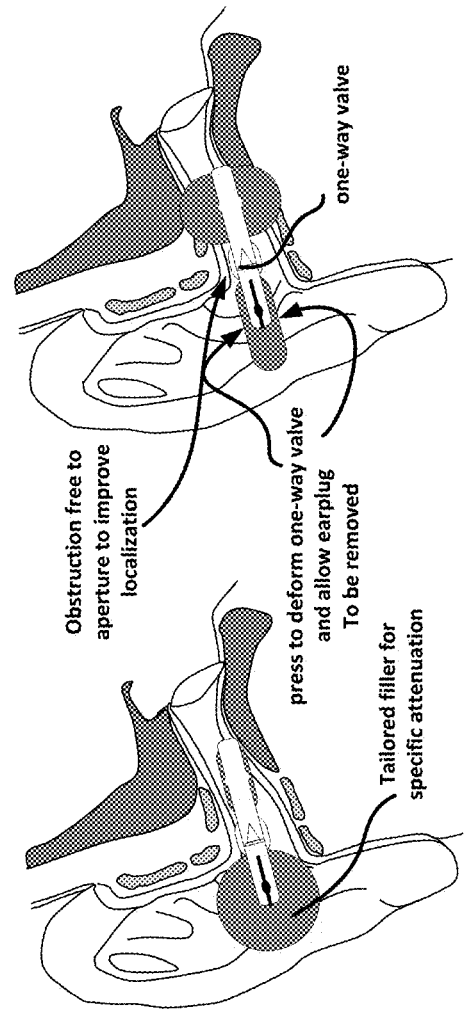
FIG. 22B is a schematic diagram illustrating non-limiting example of earplugs with modifiable attenuation.

FIGS. 22A and 22B illustrate concepts of a membrane based earplug, that should fit the majority of the population (5th percentile-95th percentile), be easy to clean/maintain, be environmentally durable (e.g. durable silicone), maximize ability to detect/identify/pinpoint sounds, be lightweight, easily donned/doffed, and be compatible with currently fielded military equipment, to include helmets. The reservoir 2200 includes a medium specifically chosen, as described herein, to control the reflection and/or the transmitted attenuated acoustical spectrum. A stent 2210 with a cut 2220 (to facilitate bending), channels the medium into a flexible distal end 2230. The valve 2240 allows one way passage of the medium into the distal end expanding the distal end (see operation in FIG. 22B). To release the pressure a user can press on the stent 2210, which bends because of the cut 2220, placing pressure on the valve 2240 opening the valve deflating the distal end. Alternatively, a house for a safety flange 2250 can be designed so that a user can squeeze the safety flange toward the stent to deform and open the valve 2240.

At least one example, FIGS. 23A and 23B, illustrates of an exemplary embodiment, includes an earplug 2300 with no valve, for example employs a manual push dimple/tab 2310 system having a fastener in the reservoir (e.g., Velcro™) that fastens (e.g., portion 2320 interlocking 223 with portion 2330) when pushed holding the fluid (gas, or liquid) in an inflation element until manually released (e.g., tab 2310 pulled to pull apart the Velcro™). The holding force $F_L$ of the reservoir internal fastener must exceed the natural restoring force of the expanded inflation element 2370. To release the expanded distal end a user pulls the tab to overcome the internal holding force of the reservoir. Note that the earplug 2300 can include a body 2350 having various thickness, encompassing a fluid chamber 2340, connected to a channel 2360, terminating at an inflation element 2370. When the tab 2310 is pushed Z the fluid moves from the chamber 2370 into and inflating at least a portion of the inflation element 2370.

Figure 25B:
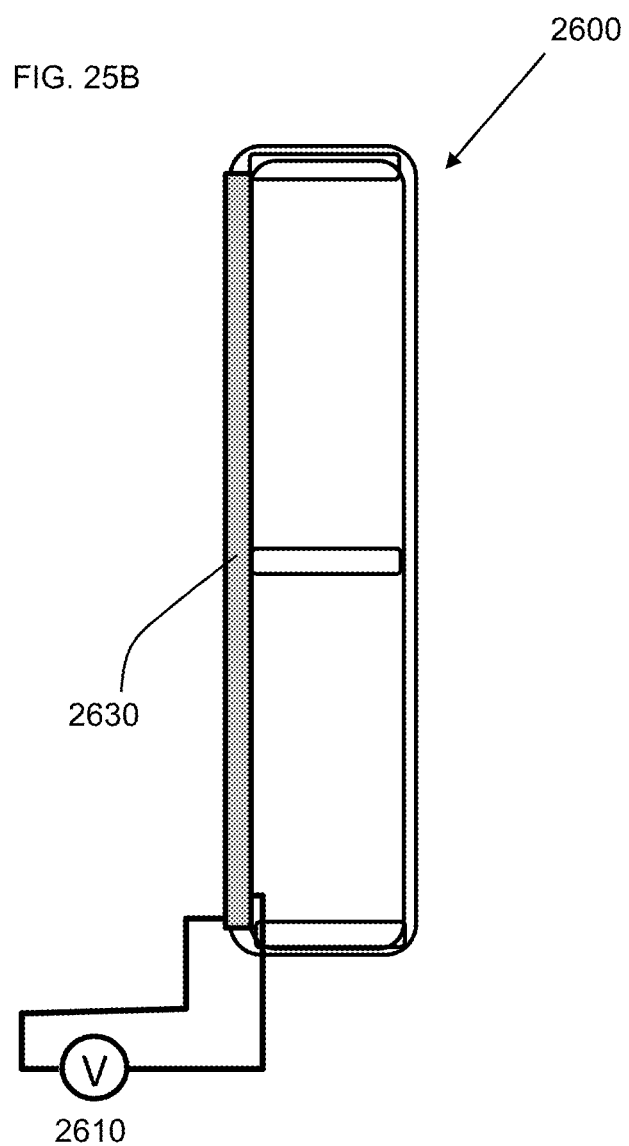

At least one further exemplary embodiment can be used as a sound panel or insert, described in more detail below with respect to FIGS. 27-31D. FIG. 24 illustrates an example of an embodiment 2400 where the membrane and/or medium can be designed to tailor the transmitted attenuated sound profile and/or the reflected sound profile (e.g., for use in concert halls). For example small filaments 2463 can be built into the membrane 2462 to absorb sound frequencies associated with the natural frequency of the filaments. The Panel 2400 can be configured such that incident wave 2411 having a spectrum 2412 incident on the panel 2400 results in a reflected wave 2421 having spectrum 2423, and a transmitted wave 2431 having spectrum 2433, where the panel has modified the initial spectrum passing through the panel 2432 into the resultant transmitted spectrum 2433. The Panel 2400 can include several layers including a combination membrane X1 that includes a membrane 2450 under tension an absorptive layer 2452 and a medium 2453 FIG. 25A illustrates an embodiment 2500 where the membrane 2550 includes cavities 2560 that can be filled with or without (e.g., gas, liquids, suspended solids) mediums to design particular resonant frequencies 2525 associated with the cavities, affecting both the transmitted and reflected acoustical spectrum. FIG. 25B illustrates an embodiment 2600 where the membrane is composed of electroactive polymers, (e.g., Nafion™) where a voltage difference across the membrane can stiffen the membrane affecting the reflected and transmitted acoustical profiles. For example a treated Nafion™ membrane, for example as done for artificial muscle research, can be used as the membrane 2630 for a panel, where the voltage 2610 across the membrane ('across' with respect to exterior and interior) can be low initially (e.g., 0.25 volts). When enhanced reflection is desired the voltage can be increased (e.g., 1.5 Volts). The fabrication of artificial muscles as known by one of ordinary skill in the art is described in EP Patent Application 0924033 A2, filed 14 Dec. 1998 incorporated by reference in its entirety.

Figure 25C:
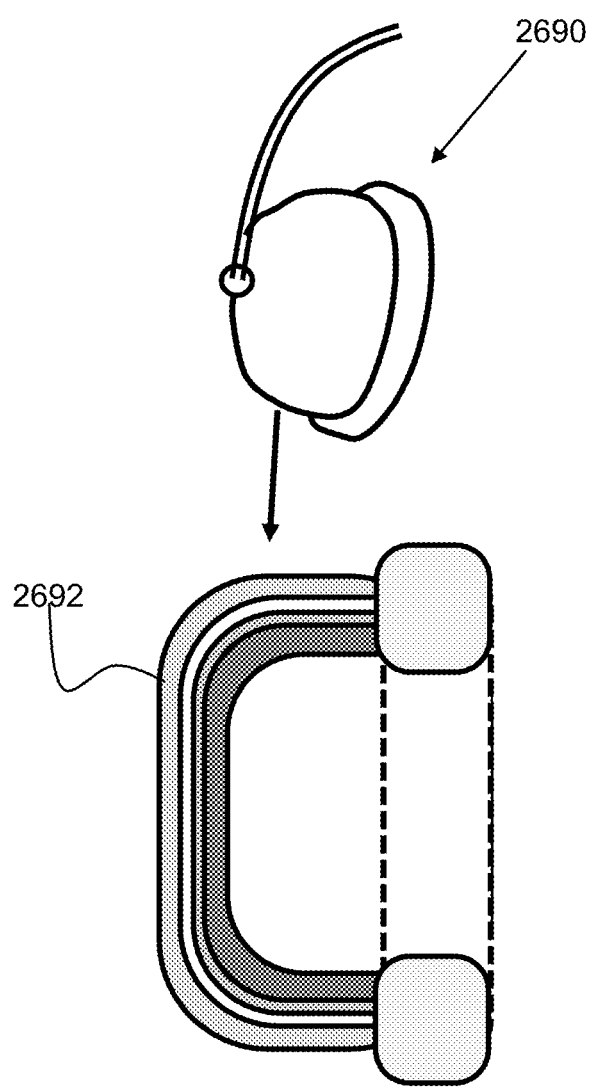
FIG. 25C is a schematic diagram illustrating a hearing protection device embodiment of the invention.

FIG. 25C illustrates an additional embodiment 2690 where a sound panel/insert in accordance with an embodiment has been inserted into an ear muff to tailor the spectrum attenuated. An additional embodiment includes the use of the sound panel/insert as an outer soft shell 2692 of the earmuff, focusing on reflecting a portion of the spectrum before attenuation. A description of the fabrication of an earmuff is described in EP Patent Application No. EP 1811932 B1, filed 16 Nov. 2005 incorporated by reference in its entirety. For example an example of a sound insert in accordance with at least one embodiment of the present invention can be incorporated into the cup shaped cap and/or as part of or inplace of the pressure-equalizing means in application EP 1811932.

Figure 26:
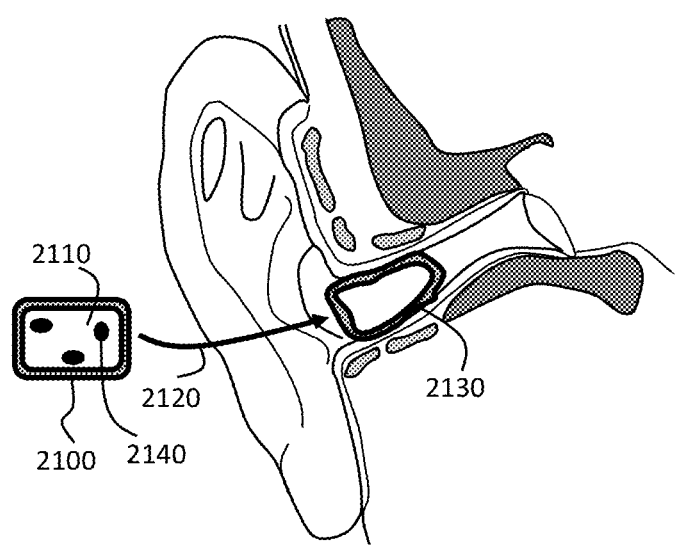
FIG. 26 illustrates an earplug in accordance with at least one exemplary embodiment.

FIG. 26 illustrates at least one exemplary embodiment of an earplug (e.g., foam, polymer flange) with a hollow chamber 2100, which has a filler material (e.g., water, aphrons, water with solid particles suspended, oil with particles suspended 2140), that can be compressed and inserted 2120 into a compacted form 2130 in the ear canal. Note that while compacting the earplug the pressure of the interior can increase. The suspended particles or aphrons 2140 can be tailored with various materials tailored to the specific attenuation properties desired.

FIG. 27 illustrates an acoustic shaping panel 2700 in accordance with at least one exemplary embodiment and FIG. 28 illustrates a cross section of the panel illustrated in FIG. 27. The panel 2700 can include fastening elements 2871, or can have attachment elements on at least one side of the panel 2700 (e.g., Velcro™ attachment). Referring to FIG. 28, an incident 2841 acoustic wave 2840 (only one frequency illustrated for clarity) with amplitude 2842 passes through the panel 2700. Depending upon the desired acoustic shaping, the panel 2700 will modify different frequencies in various methods, for example reducing the amplitude (measured in Decibels or dB). The transmitted 2851 acoustic wave 2850 has a reduced amplitude 2852. The reduction amount of the incident amplitude (2852) is a function of the properties of the case (e.g. front 2810, back 2820, and rim 2830) of the panels and the properties of the medium 2880. The medium 2880 can be contained within a medium retainer container 2870 (e.g., a bladder). The medium 2880 can be inserted under various pressures to obtain various levels of amplitude reduction (e.g., attenuation).

FIG. 29 illustrates attachment of the panels of FIG. 27 on a wall 2900 in accordance with at least one exemplary embodiment. In the non-limiting example illustrated, the acoustic properties of a wall 2900 can be modified by adding multiple panels 2700 which are placed 2910 next to each other.

FIG. 30A illustrates cross section of an acoustic shaping panel in accordance with at least one exemplary embodiment. Referring to FIG. 30A, an incident 3041 acoustic wave 3040 (only one frequency illustrated for clarity) with amplitude 3042 passes through the panel. Depending upon the desired acoustic shaping, the panel will modify different frequencies in various methods, for example reducing the amplitude (measured in Decibels or dB). The transmitted 3051 acoustic wave 3050 has a reduced amplitude 3052. The medium 3080 can be contained within a medium retainer container 3070 (e.g., a bladder). FIG. 30B illustrates a closeup of the medium illustrated in FIG. 30A. In the non-limiting example illustrated in FIG. 30B the medium 3081 includes a suspension 3084, for example an aphron including a sheath 3083 and core 3082. For example the sheath 3083 could be an aqueous solution including a surfactant and a core 3082 including a mixture for example oil, or H2O+NaCl, or other mixtures.

FIGS. 31A, 31B, 31C, and 31D illustrate variations of cross sections of acoustic shaping panels in accordance with various exemplary embodiments. Panels can include various combinations of mediums to shape the acoustic properties of the panels, or a combination of individual panels. For example FIG. 31A illustrates two mediums 3110 and 3120 that can be combined to provide an overall panel property, while FIG. 31B illustrates two panels attached 3113 (e.g. via Velcro™, glue, screws, nails). Additional non-limiting examples are illustrated in FIG. 31C and FIG. 31D, where various combinations of mediums are combined to provide tailored acoustic shaping properties of the panels. For example FIG. 31C includes mediums 3141 and 3143 and fasteners 3171 and FIG. 31D includes multiple mediums 3191, 3192, and 3193.

Figure 32C:
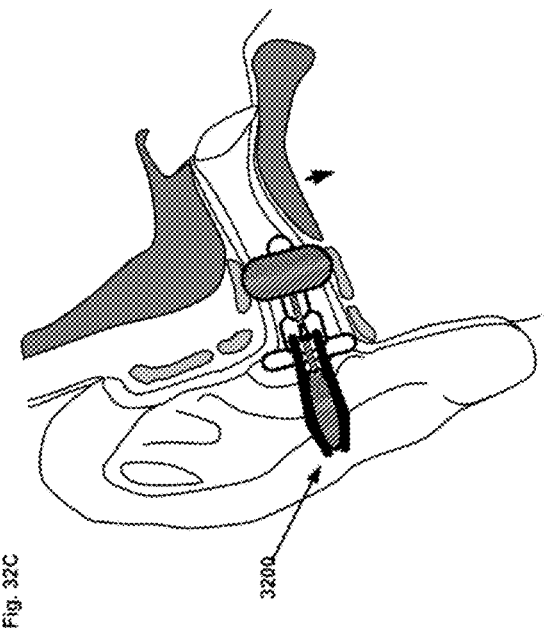
FIGS. 32A, 32B, and 32C illustrate the configuration and operation of at least one exemplary embodiment.
Figure 32A:
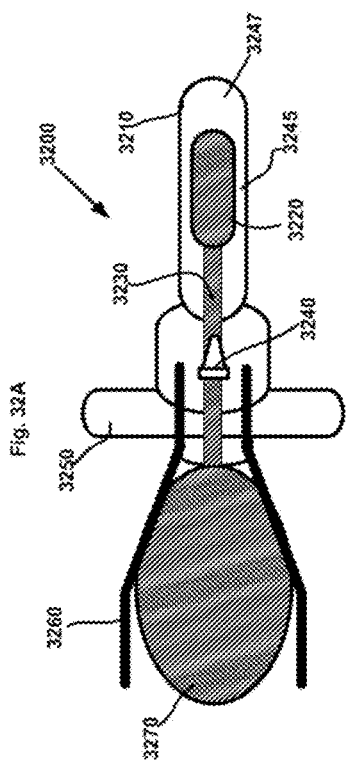
Figure 32B:
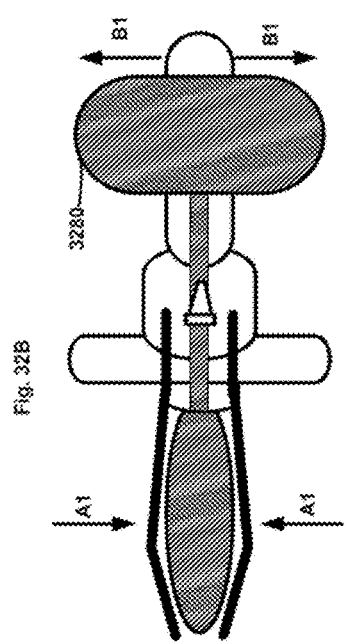

FIGS. 32A, 32B, and 32C illustrate the configuration and operation of at least one exemplary embodiment of an earplug. The earplug 3200 includes a reservoir 3270, a moveable element 3260, a safety flange 3250, a valve 3240, a fluid channel 3230, a distal end reservoir 3220, and a distal end shaft 3210. The shaft 3210 can expand for example including regions of various thicknesses (e.g., a thin region 3245 and a thicker region 3247), or the shaft can have a port from the distal end reservoir to a flexible element around the distal end of the shaft 3210 which expands while the shaft remains generally constant.

FIG. 32C illustrates operation of the earplug Illustrated in FIG. 32A, where the moveable element 3260 is depressed (squeezed) for example by a user's fingers, to constrict the reservoir 3270. The constriction of reservoir 3270 forces the medium in the reservoir through the channel 3230 past the valve into the distal end reservoir 3220. The passing of the medium through the valve 3240 prevents the return of the medium into the reservoir 3270, thus once depressed the fluid remains in or near the distal end reservoir. If the shaft is flexible then the thin wall portion 3245 will expand 3280 in response B1 to the reservoir constriction A1. Note that a flexible element (not shown) can be encased around the shaft where fluid entering the distal reservoir travels via a port to the flexible element expanding the flexible element, which becomes the expandable element 3280. Note that a modification to the non-limiting example illustrated can include a second return valve that opens when a design pressure is reached, for example if one seeks to remove the earplug, when upon pulling the pressure is greater than a designed level (e.g., 400 mbar gauge pressure) then medium will flow from the distal reservoir 3220 to the reservoir 3270. FIG. 32C illustrates use of the earplug 3200 in an ear.

Figure 33:
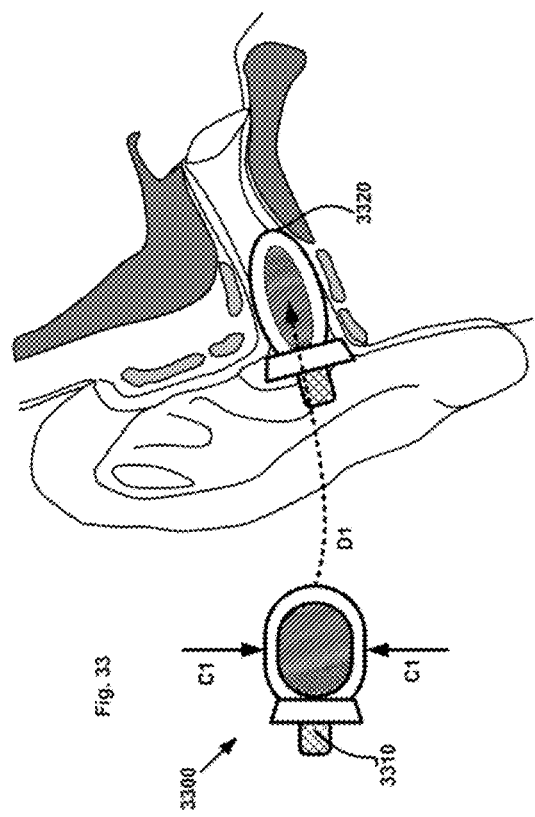
FIG. 33 illustrates an earplug in accordance with one exemplary embodiment.

FIG. 33 illustrates another non-limiting example of an embodiment. The earplug 3300 is a foam plug with a reservoir and a finger tab 3310 to hold. A user squeezes C1 the foam to a smaller insertion form, which is inserted D1 into the ear canal 3320. Note that the reservoir can include a fluid foam medium, which can be compressed (for example where the gas bubbles get smaller upon compression), thus increasing the pressure of the inserted reservoir.

FIGS. 34A, 34B, and 34C illustrate the configuration and operation of at least one exemplary embodiment. The earplug 3400 includes a reservoir 3470, a moveable element 3460 with a distal end 3420, a safety flange 3450, a valve 3440, a fluid channel 3430, a distal end reservoir 3430 and at least one contact 3245. Note the safety flange 3450 can additionally include a flange reservoir. FIG. 34B illustrates the operation the earplug 3400, where the reservoir 3470 is constricted by moving E1 (squeezing) the moveable element 3460 forcing a portion of the medium through the valve 3440 into a distal end reservoir 3431 and optionally a safety flange reservoir. The medium moving into the distal reservoir 3431 allows the reservoir to remain constricted by the valve 3440 prohibiting backward flow. The contacts 3245 move as the moveable element 3460 is moved, where the contact 3245 press lightly against the walls of the ear canal securing the earplug. FIG. 34C illustrates use of the earplug 3400 in an ear.

FIGS. 35A, 35B, 35C, and 36 illustrate the configuration and operation of at least one exemplary embodiment. FIG. 35A illustrates a non-limiting example of an earplug embodiment 3500, including a deformable casing 3510 (e.g. foam), encircling a reservoir 3520, a valve 3540, a flexible distal end 3535, and optionally a flange 3530. FIG. 35B illustrates the operation of the earplug 3500, where depression G1 of the deformable casing 3510 constricts the reservoir 3520 forcing a portion of the medium past the valve into the flexible distal end 3535 (e.g., a balloon on a shaft, a flexible shaft with varying thickness) expanding H1 the flexible distal end 3535. The expansion of the flexible distal end 3535 can expand the flange 3531. In at least one embodiment a release mechanism can be included for a user to squeeze open a flexible valve, allowing passage of the medium from the flexible distal end 3535 back to the reservoir 3520. For example FIG. 35C illustrates an incorporated release mechanism that when pressed M1, effectively presses N1 on the flexible valve opening the valve for backflow. FIG. 36 illustrates use of the earplug 3500 in an ear.

Although considerable discussion has been included with respect to use in earplugs, additional embodiments of the invention can be used in other systems and devices that can benefit from controlling the acoustic spectrum passing through the device. For example, helmets, flexible wrap that is wrapped around devices for acoustic isolation, tool handles (e.g., jackhammers), around the hull of ships to mitigate acoustic loss, and other uses one of ordinary skill in the relevant art would know. For example FIG. 37 and FIG. 38 illustrates an embodiment used in a helmet 3700 (e.g. for use on aircraft carriers or other noisy environments) where several liners 3710 and 3720 (although a single liner can be used), where the liners (3710 and/or 3720) each can include different fluid mediums to shape the acoustic profiles entering the helmet 3700.

FIGS. 39-40 illustrates various flexible distal ends developed by Innovation Labs and Dr. Keady, while FIG. 41 illustrates a novel distal end spiral feed system which enhances uniform expansion about a stent 3910. The tip 4000 can include an acoustic port or be sealed. The expandable membrane 3900 expands and is attached by stent 3910.

Figure 42:
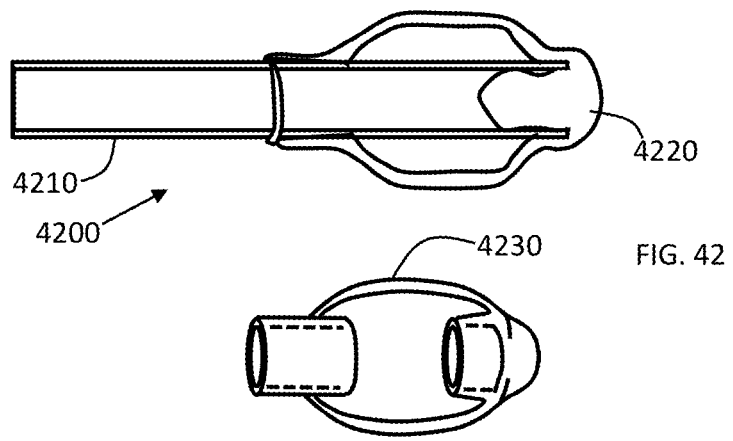
FIG. 42 illustrates a tip in accordance with at least one exemplary embodiment.
Figure 43:
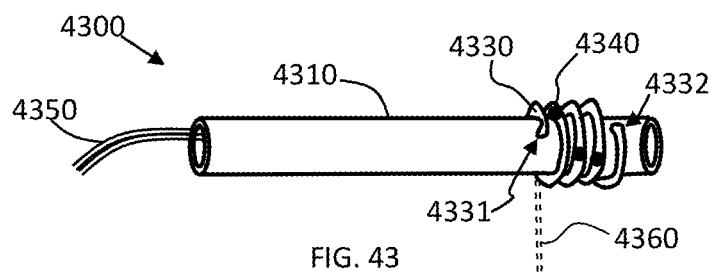
FIG. 43 illustrates a novel distal end spiral feed system which enhances uniform expansion about a stent.
Figure 44A:
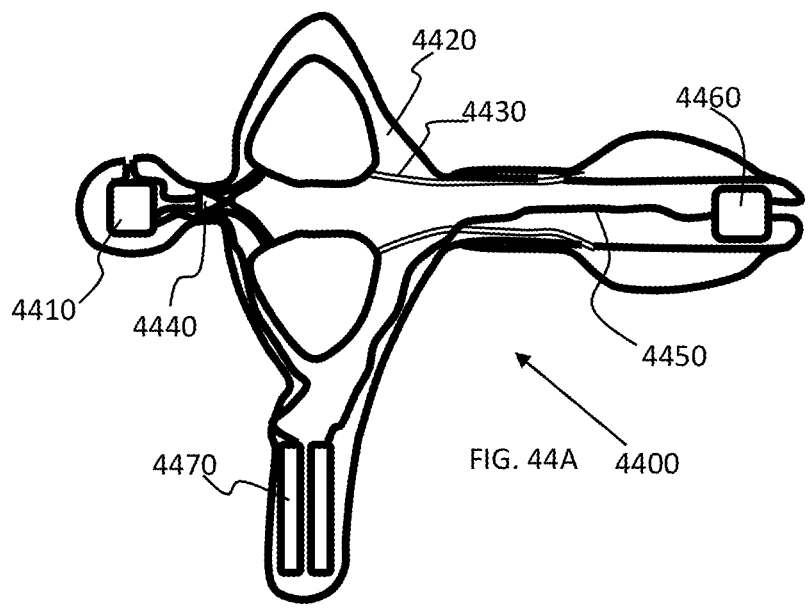
FIGS. 44A, 44B, 44C, 44D, 44E, 44F, 44G, 44H, 44I, 44G, 44J illustrates various eartips, earplugs in accordance with various exemplary embodiments.
Figure 44B:
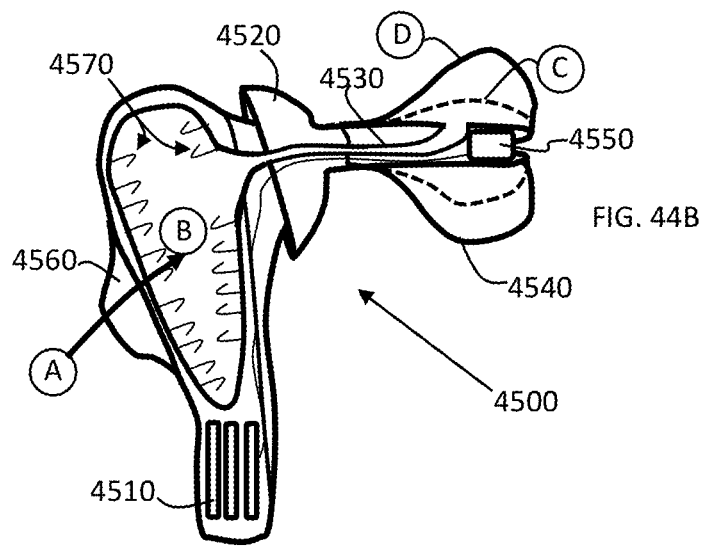
Figure 44C:
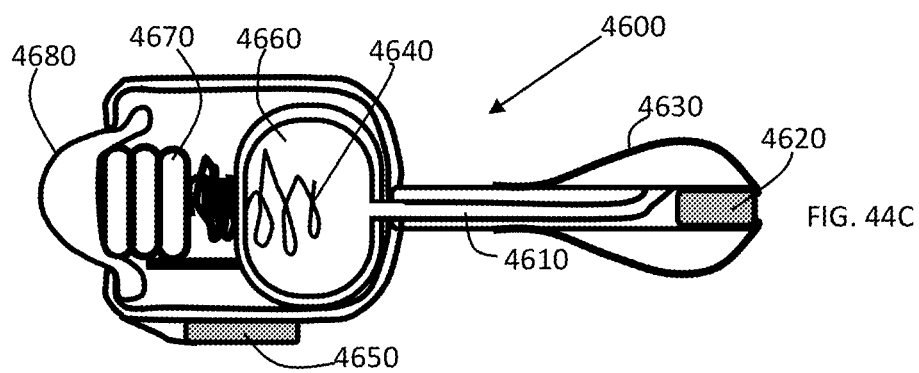
Figure 44D:
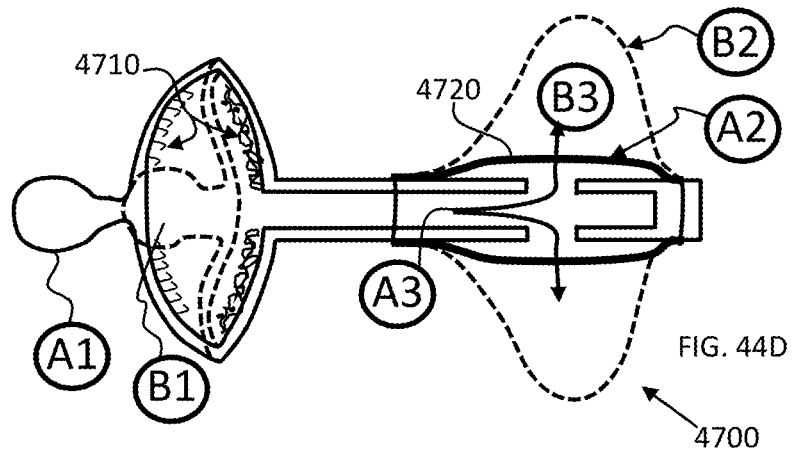
Figure 44E:
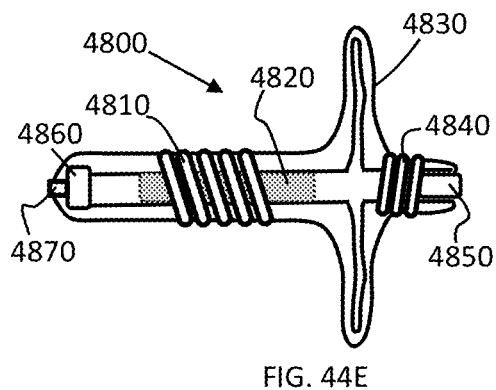
Figure 44H:
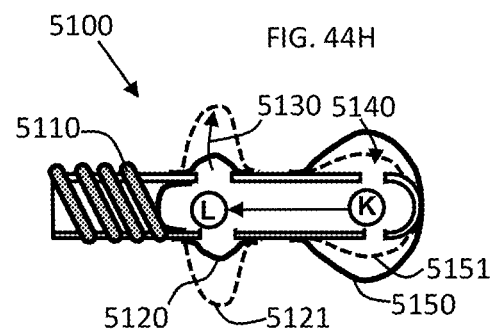
Figure 44F:
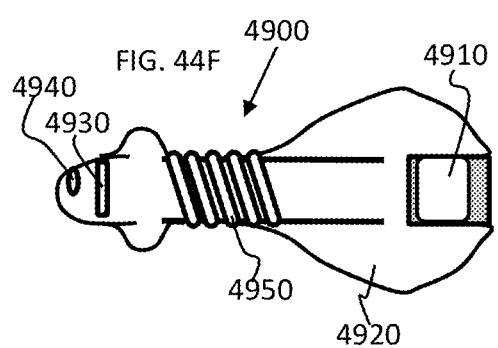
Figure 44I:
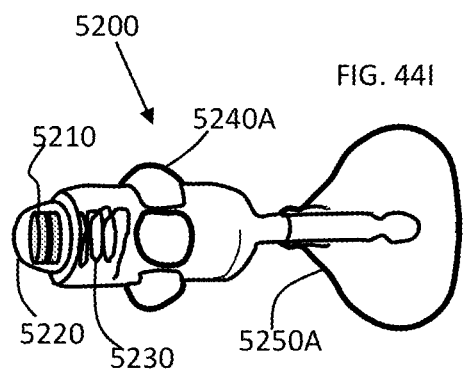
Figure 44G:
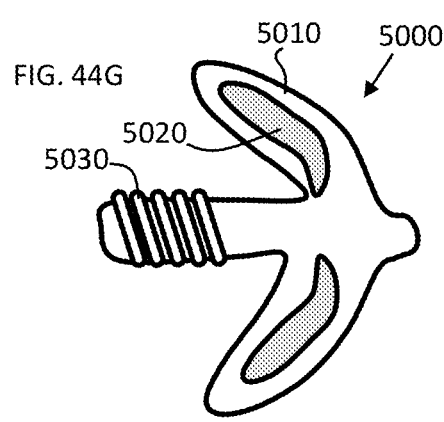
Figure 44J:
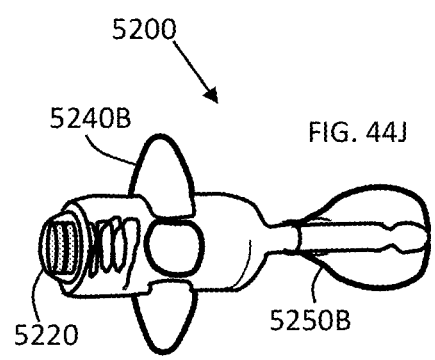

FIGS. 42-44J illustrates multiple examples of embodiments for earplugs, hearing aids, and earpieces. FIG. 42 illustrates an earplug 4200 including a stent 4210 and an inflation element 4220. The inflation element can be formed as a single unit 4230. FIG. 43 illustrates the system of FIG. 40. An inflation tube 4350 can be placed through a hole 4331, then an end 4360 wrapped 4330 around the stent 4310, with holes 4340 in the inflation tube. When the winding in completed the end of the inflation tube 4350 is inserted through a second hole 4332. FIG. 44A illustrates an earplug/hearing aid 4400 having an ambient microphone 4410, a body 4420 that serves also as a depth control flange, inflation tubes 4430 (feed tubes) a one way vent 4440 (e.g. valve), receiver/microphone 4460, and wires 4450. FIG. 44B illustrates an embodiment of an earplug/hearing aid 4500, including inflation tubes 4530, depth control flange 4520, inflation element 4540, tab 4560, interlocking mechanism 4570, batteries 4510, where a user that presses inward, A to B, forces fluid into the inflation element 4540 expanding the inflation element 4540 from C to D. FIG. 44C illustrates an embodiment of an earplug/hearing aid 4600, including an inflation tube 4610, a button 4680 pressing the batteries 4670, where a user can press the button 4680 engaging the battery 4670 to supply voltage to electrodes 4640. Where the electrodes 4640 are embedded in a medium 4660 (e.g., water) to turn the medium into gas (e.g., electrolysis), where the gas and fluid have a increased pressure that expands the inflation element 4630. The earplug/hearing aid 4600 can include an ambient microphone 4650, and an internal receiver/microphone 4620. FIG. 44D illustrates an earplug 4700 including an interlocking mechanism 4710 where when a user moves a tab from position A1 to B1 moves fluid in a reservoir, from A3 to B3, into an inflation element 4720 expanding the inflation element from A2 to B2. FIGS. 44E, 44F, 44G and 44H illustrate ferrofluid and/or electro fluid earplug/hearing aid systems. For example FIGS. 44E and 44F include ambient microphones 4860, 4930, each having a microphone ports 4870 and 4940. FIGS. 44E and 44F additionally include coils 4810, 4950, which can be used to change local magnetic fields, ferrofluid 4820, 4920, and in the case of earplug/hearing aid 4800 an opposing coil 4840. The ferrofluid can react to the magnetic fields moving into and way from the inflation elements 4830, expanding them. FIG. 44G illustrates a ferrofluid system 5000 with ferrofluid 5010 in isolated chambers in a flange 5010 where a coil 5030 changes the local magnetic field collapsing or releasing the flange 5010. The earplug system 5100 illustrated in FIG. 44H includes a restoring membrane 5120 that when expanded 5121 exerts a restoring force attempting to impose the attraction of the ferrofluid responding to an increased magnetic field (e.g., moving from K to L). When the magnetic field is released (current to minimal) the restoring membrane forces the ferrofluid into the inflation element expanding it from 5151 to 5150. FIGS. 44I and 44J illustrate the same system using a push button 5220 to engage the battery 5210 with the magnetic coil 5230 increasing the current and applying a magnetic field which attracts the ferrofluid from the tip to the restoring membrane region expanding the restoring membrane 5240B.

Additional exemplary embodiments use a field responsive fluids (e.g., Electric and Magnetic Fluid Technology: Any device portion that includes ferrofluids, magnetorheological fluids, and Electro-rheological fluids/electric field responsive fluids. For example one exemplary embodiment uses a magnetic generator (e.g., coil) to control FerroFluid in an earpiece to move from one point of the earpiece to another, and/or to change the attenuation characteristics of the earpiece. At least one exemplary embodiment uses an ER fluid to change the attenuation properties via the application of an electric field. For example for an earpiece if the insertion depth control flange contains an ER fluid the viscosity of the fluid can be changed by applying an electric field across the flange changing the characteristics of the flange.

At least one exemplary embodiment also use a combination ER and FF fluid by mixing them so that a magnetic field can be used to move the fluid while an electric field can be used to gellify the fluid.

Figure 45:
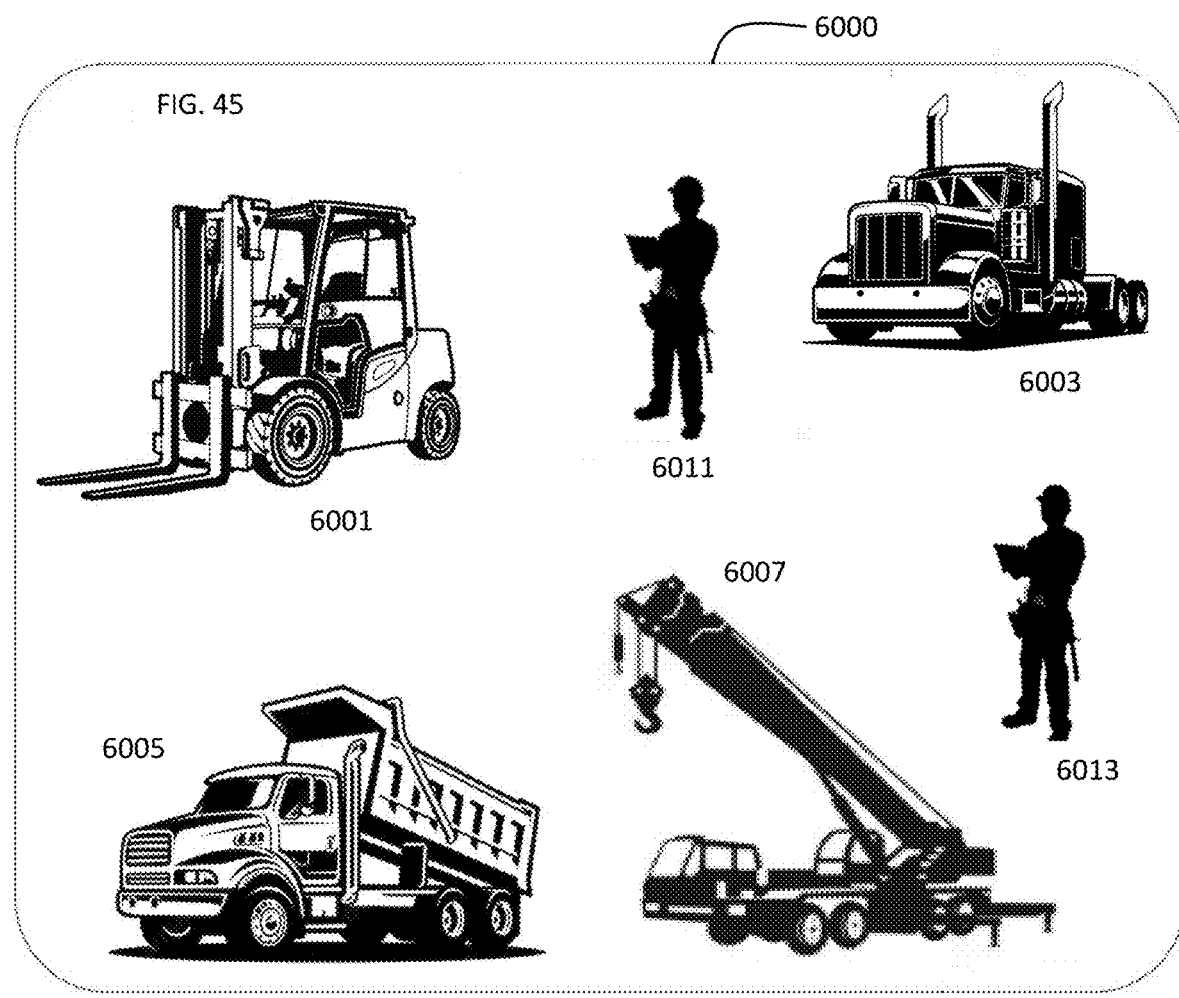
FIG. 45 illustrates a work environment.
Figure 46:
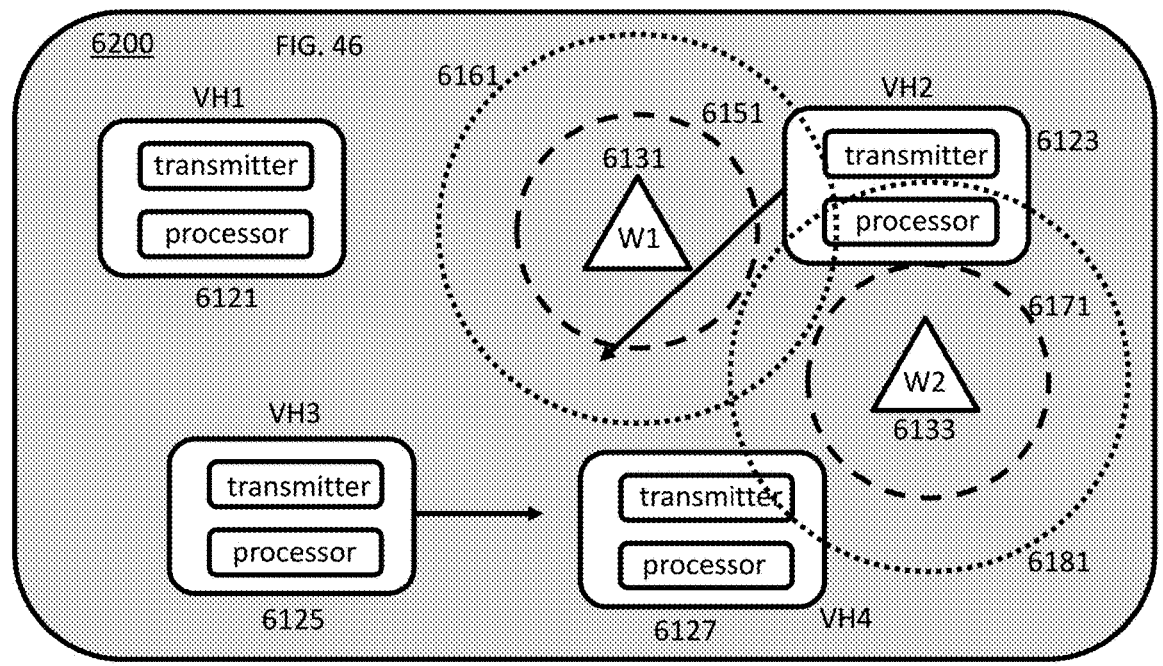
FIG. 46 illustrates the computer display that represents the work environment of FIG. 45.

At least one embodiment is directed to using acoustic (e.g., earphone), haptic, and visual indicators to notify persons of a harmful environment, and is even control vehicles so as to decrease danger to items and persons. FIG. 45 illustrates a sample work environment, while FIG. 46 illustrates a sample of the computer display equivalent of the work environment of FIG. 45.

Notification can take the form of various devices and methods (acoustic, haptic, visual, thermal, and combinations of such). Exemplary embodiments are directed to or can be operatively used on various devices, helmets, safety glasses, watches, belt buckles, passive earplugs for hearing protection or electronic wired or wireless devices (e.g., hearing aids, ear monitors, earbuds, headphones, ear terminal, behind the ear devices or other acoustic devices as known by one of ordinary skill, and equivalents) or any other device attached to the body. For example, an ambient microphone can measure the ambient sound pressure levels a user is exposed to and when the exposure level reaches a threshold level (e.g., 90% of daily recommended exposure) a tactile notification device can be activated to notify the user, alone or in combination with another notification device (e.g., visual LEDs). In all of the examples illustrated and discussed herein, any specific values should be interpreted to be illustrative only and non-limiting. Thus, other examples of the exemplary embodiments could have different values.

The non limiting embodiment discussed below is directed to a personal noise exposure monitoring system, however any notification system where a tactile/acoustic/visual notification can be used is within the scope of the invention. The system will not only log noise exposures but also provide immediate warning to the worker about then-current, potentially hazardous noise exposures, as well as secondary relevant information so that the worker will know more details about his exposure level and dose, and can make informed decisions to protect themselves. This is important because noises in workplaces are often not constant nor are the noise sources stationary, so workers need to be aware of changing environments and concomitant exposure levels due to either their moving around or variations in equipment/process emissions or movements. The head-mounted system, can both warning and informational displays for the worker, the worker who works in an environment where noise exposure levels vary will be able to determine when and where he/she needs to wear hearing protection devices or take other preventative action.

Most current dosimeters are not designed to provide instantaneous noise information to a user; rather they are designed to prevent tampering of the settings and the data; this feature thus obviates a worker from gaining real-time information about surrounding noise. Even those dosimeters that are designed to display data to the workers directly are designed with on-unit visual displays that require the worker to turn their head and intentionally look for information, which is not always in a readily-understandable form, and is certainly not designed to warn the worker of imminent hazard potential. The current dosimeter designs are acceptable to measure noise exposure of a worker in a work-shift and record them for later analysis and comparison to some action or criterion levels, such as those promulgated by OSHA or the military. In addition to the traditional functionalities of dosimeters, the proposed personal noise exposure monitoring system will be able to provide real-time noise hazard information to the workers via multi-modal displays that will draw the worker's immediate attention by redundant sensory modalities (visual and tactile senses) to provide the proper levels of information to first warn, and next to inform about the hazard in more detail and offer preventative advice. People tend to respond faster and quickly to multi-modal displays than to a uni-modal display. Furthermore, the redundancy of multi-modal displays also provides more resistance to masking or interference effects that may cause one of the modalities to be missed, and provides a backup warning path in the event of one modality's failure. Once the worker is aware that he/she is under a present or imminent noise hazard, he/she can then look at the secondary visual display on the device to gain more detailed information about the noise's level and dose, and receive advisory guidance on possible actions to take to avoid noise-induced hearing loss.

Various thresholds can be set. For example, the OSHA regulation (1983) for noise exposure allows a time-weighted average (TWA) exposure of 90 dBA (100% dose) for an 8-hour work shift as the criterion level, but hearing conservation programs are required when the TWA is at 85 dBA (50% dose) and above, which is the action level. On the other hand, NIOSH (2012) recommends 85 dBA TWA for an 8-hour work shift as the criterion level or 100% dose. Also, different agencies and branches of the U.S. military recommend different exchange rates for dosage calculation as well. Various displays can be tailored for different work conditions and can the type and form of tactile notificator. For example possible examples of display formats for the head-up visual display could be colored LED lights with varying colors, using standards of green, yellow, and red, and/or blinking patterns, alphanumeric displays with different languages, or visual icons. The tactile displays can be parameterized with varying intensity, pulse rates, and/or vibration patterns. Characteristics of cultural subgroups can aid in designing multi-modal displays rendering them cross-cultural in effectiveness. Identification of such characteristics can be used in notification systems aiding in enhanced user acceptance.

In view that a noise environment is dynamic in many workplaces, at least one embodiment includes a quickly-responding scheme for alerting workers of their immediate noise exposure. The scheme takes into account workplace noise exposure characteristics so that the alert timing can be beneficial or early enough so that workers can take preventive actions.

At least one embodiment can use multi-modal displays, where multiple methods of notification can be used, for example a visual display and/or tactile display.

Visual display can be subdivided into two levels: $1^{st}$ level visual display can be colored LED lights that can be used to alert the worker to capture immediate attention to noise hazard; $2^{nd}$ level visual display can be an alphanumeric display that can display detailed information such as current sound level, cumulative exposure dosage, and expected time to maximum dose at current sound level or cumulative sound exposure.

The tactile display, transducing small vibrations to the user's body (e.g., head) via tiny vibrotactors (e.g., mounted on eyeglass temples or in a hardhat headband), can be a complimentary or redundant warning avenue to the $1^{st}$ level visual display to command attention. However, it is also possible to design the tactile display to convey more information than a simple warning via variations in the vibration pattern, such as increasing the vibratory frequency and/or amplitude as noise level rises, or providing a constant pulsating, compressive vibration as maximum dose is imminent. Another possibility of tactile display is conveying directionality of noise if the noise requires the worker to localize the sound and react to it in certain way. Localization of a backup alarm could be such an example, because hearing and heeding a backup alarm in noise is a significant safety problem in industry (Alali & Casali, 2011).

At least one embodiment can consist of multi-modal displays and a selected, modified dosimeter. Additional embodiments can be coupled with safety glasses and other devices such as a safety helmet (hardhat). As most noise hazard information is available from currently available dosimeters, existing, off-the-shelf dosimeter can interact with our multimodal displays of at least one embodiment.

A first embodiment add multimodal or tactile displays to safety glasses. Safety glasses will provide a convenient mounting opportunity on the rim of the eyeglass lense plane, or at the hinge of the temple piece, to display colored LED lights that will alert the workers with varying noise hazard information. A small vibration transducer (i.e., vibrotactile device) will be mounted on, or embedded within the temple piece of the safety glasses, and will complement the visual LED signal to draw immediate attention of the worker when needed to convey a conspicuous warning. Thus, the worker will be alerted when there are significant changes to his/her noise environment, or present or imminent hazards, via both colored lights and vibration. Example of such changes can include a sudden increase of noise level that exceeds the allowable limits of either continuous noise (115 dBA rms) or impulse noise (140 dB peak). Cumulative noise dosage at a preset limit for warning activation can be another reason for alerting the worker. A separate alphanumeric display ("head-down" style) can be attached to the dosimeter itself, to display detailed noise hazard information when necessary. Simple pushbuttons can allow the workers to navigate the system and retrieve the necessary information, which can include dBA level and dose data, as well as corresponding preventative measure information which will guide the worker.

A second can be integrated with safety hardhats instead of safety glasses. Hardhats will allow several positions to mount both the visual LED display, such as on the underside of the brim, as well as the vibration transducers, which can be headband-mounted. As mentioned prior, one can add additional vibration motors to convey the direction of a noise source, such as a backup alarm for a vehicle, increasing safety in dynamic workplaces where those alarms may be masked by the noise.

The safety glasses, goggle, face shield, can include several multi modal notification systems, for example visual (e.g., LED, color lights, varying light frequency and/or intensity in time), haptic (e.g., surface pressure variations, vibration motors, varying vibration frequency and/or intensity in time), audio (e.g., alarms, audio frequency and/or intensity variations in time), and temperature (e.g., variations in temperature amplitude in time).

A haptic indicator can also be used in accordance with at least one embodiment. For example a vibrator motor (e.g., adafruit's vibrating mini motor disc product ID 1201, 1.5V 20 mA Micro Pager Motor) can be mounted in user safety equipment. The haptic indicator can be mounted where a user will most notice. For example on the bridge of safety glasses or throughout a helmet, where the haptic intensity can be varied to provide information on location of danger. For example a helmet with various haptic indicators can vary which haptic indicator is activated depending upon the location of the hazard.

A non-limiting example of a dosimeter, for example 3M™ NoisePro Kit NP-DLX, which can be fitted onto a belt.

FIGS. 45-46 illustrate a vehicle and a worker in a dangerous work environment and a notification system of at least one embodiment. Sensors (e.g., dosimeter, transducers) on vehicles and workers can be fed (e.g., via Electromagnetic Waves) into a monitoring system (e.g., a computer). The monitoring system keeps track of the location and movement of hazards in the work environment, predicts future potential hazards (e.g., using Kalman Filters to predict location) and sends notification signals to both vehicle operators and workers. The notification signals can activate alarms and can even deactivate vehicles if needed. The notification signals can take various forms, for example they can be audio (tones, vocal, acoustic icons such as sounds similar to the hazard or recognized as having a particular meaning) haptic, visual, and/or a combination of these.

FIG. 46 illustrates a computer monitoring system coupled with personal notification systems in accordance with at least one embodiment. The monitoring system, for example including a processor, can model the work environment 6200 (e.g., using simulation agents (e.g., 6131-W1, and 6133-W2) to model the workers, C, C++, MatLab™). The montoring system can then send signals wirelessly or wired to any object in the work environment that has a receiver. The received signal can be used by a processor to activate an alarm on any object. Optionally the processor can control the object to minimize the hazard. For example the monitoring system can control vehicles in the work environment, for example slowing them down upon calculation of imminent harm (e.g., a few seconds prior to impact) to a worker. For example if a worker is too close to a vehicle backing up the processor can send a signal to slow the vehicle down.

FIG. 45 illustrates a work environment and an equivalent model. For example the work environment 6000 can include vehicles (6001, 6003, 6005, 6007) and workers (6011, 6013). A computer can model 6200 the environment 6000, where vehicles are illustrated as symbols (6121, 6123, 6125, 6127) and workers are also illustrated as symbols (6131, 6133), such as flow chart shapes, letters abstract forms. Regions around workers can be set (6151, 6161, 6171, 6181) so that when vehicles enter certain regions signals can be sent, for example signals can be sent to the workers so that audio, visual, and/or haptic warnings are played. Regions (e.g., 6151) can vary in size depending upon possible threats, for example if there is a fast moving vehicle (e.g., speed Vs) and the average notification and response time has been determined to be t-response, then the radius from the worker, for example from 6131, to determine 6151 can be at radius-6151=Vs*t-response*SF, where SF is a safety factor (e.g., 1.01-10.0), while the radius to determine 6161 could be Vs*t-response*SF*SCF, where SCF is scale factor (e.g., 1.1-100.0). The radii can vary as the movement various of the various vehicles and movement of the workers. Each vehicle and/or worker can contain a transmitter, receiver and a processor (e.g., for a worker their cell phone) attached to a notification device or with the ability to interface with a worker's headgear (e.g., hearing protector, earphones) or the vehicle itself (e.g., via the vehicles display and/or speakers). For example, a message could be send to the display of a vehicle presenting a warning that a worker is close.

Figure 47:
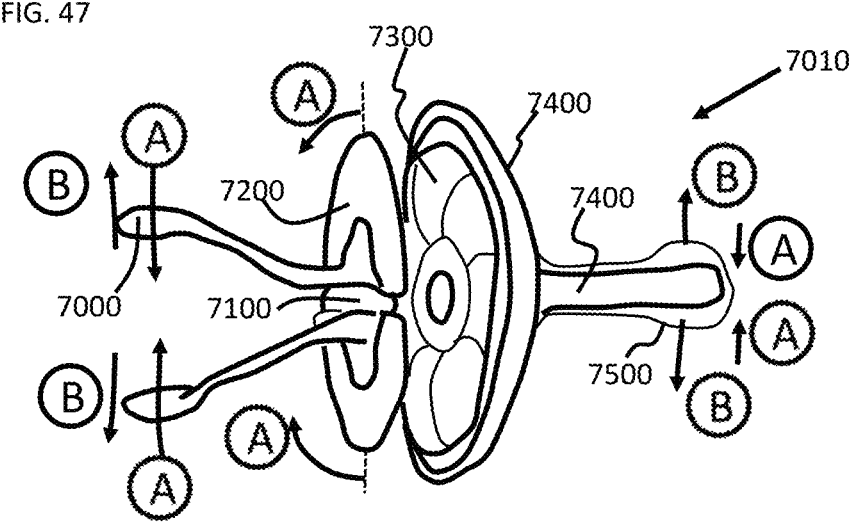
FIG. 47 illustrates an embodiment of an earphone/earplug.

FIG. 47 illustrates an embodiment of an earphone/earplug 7010. The earplug/earphone can include and acoustic channel if sound is to be played through the stent 7400. The membrane 7500 at the distal end can be expanded when tabs 7000 are released (e.g. unpinched). The tabs 7000 can be connected by a resilient connector 7100, which tend to restore the tabs to a position B when released. When tabs 7000 are pinched, position A, the membrane 7500 collapses to the stent 7400. When the tabs 7000 are released then the firmer portion 7200 pushes against a reservoir 7300 which pushed a fluid (air, liquid, low viscous gel, fluid with suspensions, ER MR fluid) through the stent 7400 expanding the membrane 7500. The membrane can be a flexible material, such as a silicon base, or fixed volume such as a urethane, although any material that can be used for inflatables both medical and lower grade can be used.

Figure 48A:
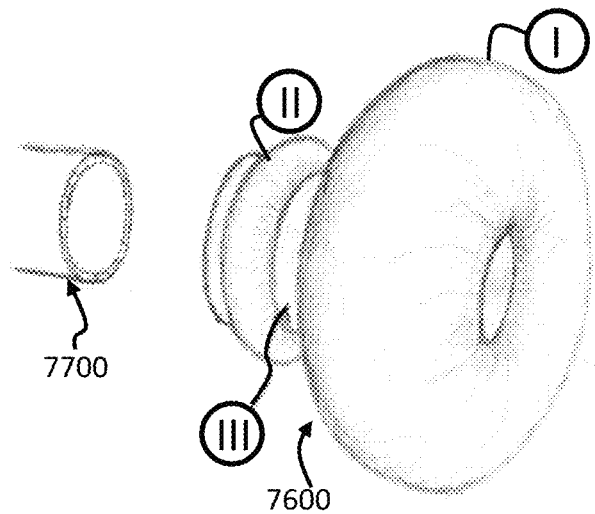
FIG. 48A illustrates a membrane tip in accordance with an embodiment.
Figure 48B:
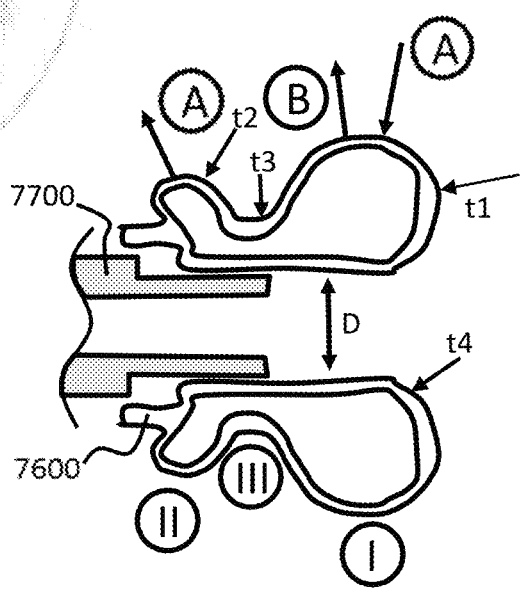
FIG. 48B illustrates a cross section of the tip of FIG. 48A.

FIGS. 48A and 48B illustrate a membrane eartip. The eartips can be sealed after formation, for example via injection molding with a gap, then sealed afterwards, or 3-D printed as sealed. The medium encompassed by the eartip can be injected prior to sealing or after sealing (e.g., hypodermic needle, and subsequent sealing epoxy). The eartips can be fabricated with various material varying from 10-120 durometer. Silicone, urethane, rubber, or other flexible polymers and materials can be used in addition to materials currently used in eartips as known by one of ordinary skill in the art. In at least one embodiment of the eartip has various portions with different thicknesses. For example region I, the portion of the eartip that enters the ear canal first can be of a different thickness (t1) than region III (t3), for example region III can be thicker, Region II can also be of different thickness (t2). For example the thickness of region I can be thicker than region II, so that when region I is compressed, region II can expand in response (A), while region III can expand less. The expansion of region II creates a restoring force creating pressure in region I pressing against the ear canal wall facilitating sealing. The thickness can vary between a fraction of a mm to several mms. The medium in the eartips and the materials forming the structure (7600, 7700) can be the same type of material as in the earphone/earplug of FIG. 47. The various thicknesses can be chosen so that region II expands (Region II-A), providing an opposite restoring force, when region I is compressed (Region I-A).

The eartip can be fabricated by various means, for example injection molding, then sealed with various filler mediums (e.g. gas, liquid, gel), and inserted upon a stent 7700, for example the eartip 7600 can have an extension portion that slides over the stent 7700.

Pneumatic (Closed-Circuit Enclosed Air/Liquid) Designs

These designs are mostly closed, entrapped fluid designs, air or liquid, although the valve versions can accommodate open system designs as well. Although they may be open until compressed, for example upon insertion into an ear canal or other opening, then an enclosed chamber, cavity can be created.

Below, as depicted in FIGS. 49-53, are three sample versions. That operate on a principle of a first member pressing against a reservoir (states Y, K, L), where the fluid in the reservoir has been pressed into an expandable tip. In the initial state, the first member presses against the reservoir, filling a small expandable tip. When a user wishes to insert the earphone, a second member is engaged, moving the first member away from the reservoir (states X, J), or a method of releasing any pressure, for example pressing on a flexible valve (M). The reservoir can be attached to the member so that as the first member (e.g., 8040, 8130, 8250) is moved (e.g., X, M, J), the reservoir (e.g., 8011, 8140, 8311) re-expands, serving to empty the expandable tip (e.g., 8010, 8110, 8210). Another version uses the restoring elastic force from the bladder in the expandable tip (e.g., 8010, 8110, 8210) to refill the reservoir when the first member is released. For example second member 8040, attached to a first member 8050, is pinched with respect to rigid member 8030, moving first member 8050 away from tip 8010. 8050 is attached to reservoir 8011, so that as it moves away from the tip 8010, fluid moves from tip 8010 into reservoir 8011. Once the earphone 8000 is inserted, the second member 8040 is released (pivots away from 8030), and an elastic force, for example from resilient member 8020, moves the first member 8050 against the reservoir, again refilling the expandable tip 8010 inside the ear canal. When a user wishes to remove the earphone, the second member 8040 is engaged again, pivoting it toward 8030, and the expandable tip 8010 is deflated and the earphone 8000 is removed. FIG. 49 shows a fingertip-operated pinching mechanism to engage the second member, while FIGS. 52-53 show a finger pressing mechanism to engage a third member 8240. FIGS. 50-51 utilizes a lanyard control system, wherein the lanyard bladder 8140 is pressed to inflate the expandable tip, while pressing 8130 opens a valve, thereby releasing the fluid and collapsing the expandable tip 8110. Each of these versions is constructed to minimize complicated valving; for example, versions I (8000) and II (8200, 8300) do not contain valves, while version III (8100) includes a collapsible flexible valve, which inventors have used in many prototypes, the valves of which are readily available. The reservoir is attached to the expandable tip via very small channels similar to Microphone-in-Real-Ear (MIRE) probe test tubes. The versions can be fabricated so that the tip is removable, requiring a flexible valve which is opened when a small pen tip-sized tube coupler is pressed into the opening at the base of the removable tip, but closed otherwise so that tip removal is possible. Note that members such as 8030, 8040, 8050, 8250, 8240 can be made of semi rigid plastic or any other type of semi-rigid material that has been used in earphones. The resilient members such as 8020, 8230 providing a restoring force can be made of flexible polymers, rubbers, silicones and similar elastic property materials. The expandable tips 8010, 8110, 8210, can be made of high elastic materials, for example where the material can be stretched to over 100% of its resting length.

Semi-Pneumatic (Shape-Memory Elastomeric) Designs

These designs, while air-filled within the confines of the membrane, have pathways for air that connect with the ambient atmosphere, thus the internal pressure is the same as atmospheric pressure. There is no air or liquid reservoir, and no need for valves or other airtight sealing mechanisms to seal-off the membrane bladder. An example of a relatively simple semi-pneumatic eartip is shown in FIGS. 54A-55. The material for this semi-pneumatic design will be an elastomer, which will be parameter-specified as to Young's modulus of elasticity, nonlinear stress-strain curve, and other relevant metrics. The notes on FIGS. 54A-55 generally depict the operation, but a brief explanation may be helpful.

Basically, the earphone nozzle is pushed gently forward to act as a "plunger" to "stretch" the elastic membrane longitudinally, rendering it just slightly larger in diameter than the nozzle for ease of insertion into the ear canal. Once in the canal, the "plunger" is retracted by the elastic spring's restoring force inherent in the membrane material (essentially, this occurs coincident with the user's fingers releasing of the earphone housing). Thus, the membrane material returns to its at-rest bulged state, thus expanding into a bulge or donut-shape around the earphone's nozzle, providing a seal against the ear canal walls. To actuate in this simple manner, the design will be comprised of a "shape-memory" elastic polymer (elastomer), and in view of the small longitudinal dimensional change necessary between its at-rest and stretched states, the dimensional operating range can easily be maintained well-within the elastomer's elastic limit. Material with fairly low hardness, on the order of 30-60 Shore A durometer, will likely be used to enable the "bulge" to conform to irregularities of the individual ear canals it may encounter in practice. It is important to note that the air inside the membrane is not sealed within it, but shared with the outside air through the nozzle and the earphone ports. This ensures that when the membrane retracts slightly backward, i.e., away from the eardrum, into its at-rest bulged state, that no suction pressure is pulled against the eardrum which could be painful. This design has many options, including variants of the profile of the at-rest shape of the membrane, which could be pre-formed into two sealing donut shapes rather than the one shown, or even other shapes. Also, in lieu of using the earphone nozzle as the plunger to elongate the membrane for easy insertion, a separate thin stem could be provided to effect the same function.

FIG. 54A illustrates the elongation state of a pull ring configuration. Housing 5400 (FIG. 54B, e.g. QC-20) A pre-shaped elastic membrane 5440, can fit around the stent of housing 5400 and elongated (X) during insertion. An open ended cup 5430 can be inserted to retain the membrane 5440. Elongation can occur by pulling ring 5410. Upon release of the ring 5410 the elasticity of the membrane 5440 returns the membrane back to the resting state (e.g., FIG. 55) and the original shape (Y) prior to elongation. The tab stop 5420 prevents the membrane 5440 from moving beyond a certain position.

Figure 56:
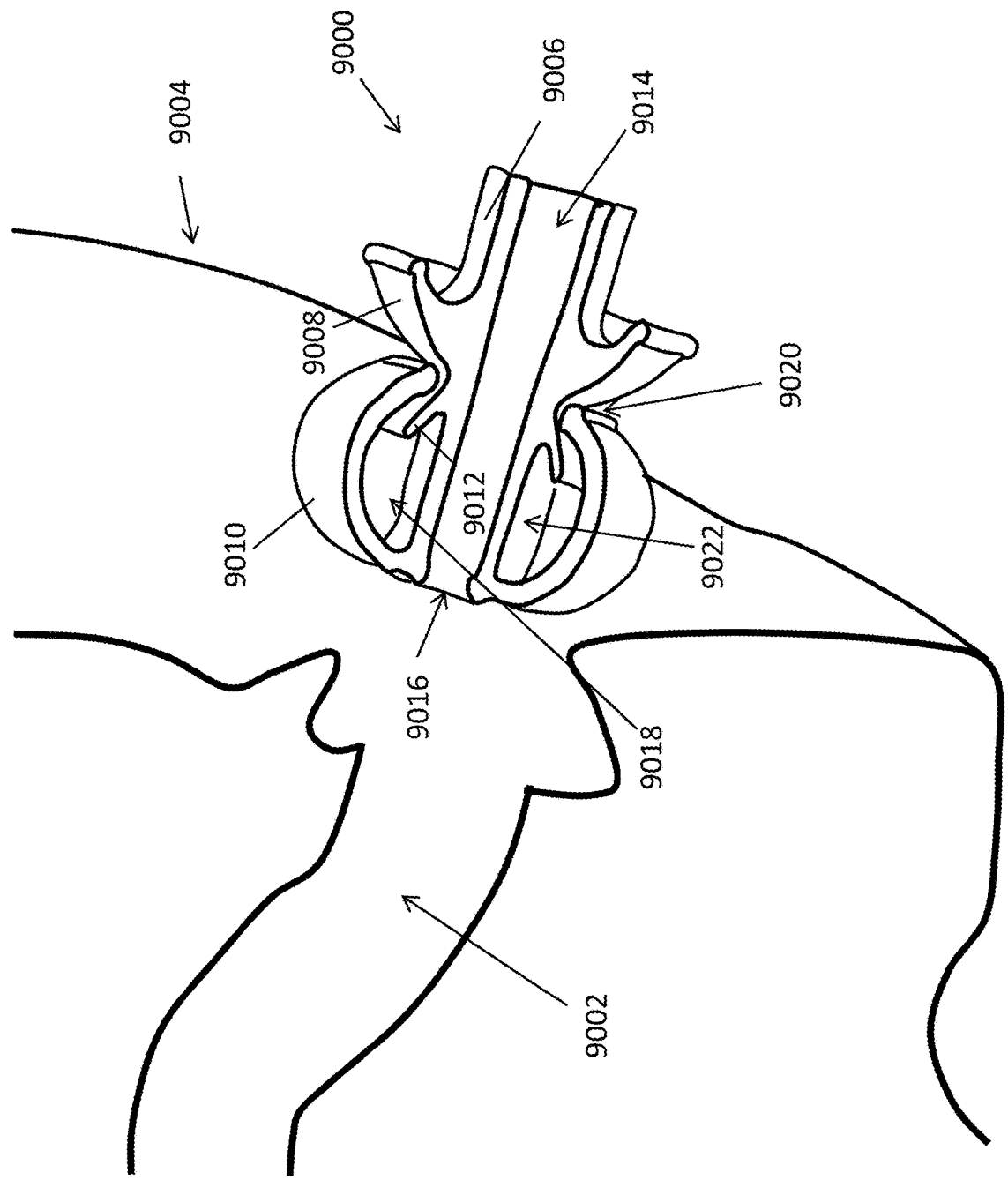
FIG. 56 is an illustration of an ear device prior to insertion into an ear canal of an ear in accordance with an example embodiment.

FIG. 56 is an illustration of an ear device 9000 prior to insertion into an ear canal 9002 of an ear in accordance with an example embodiment. A section of ear device 9000 is cutaway to provide detail of internal features. In one embodiment, the section of ear device 9000 that is cutaway is substantially equal to what is shown and disclosed herein. Ear device 9000 can comprise the same materials disclosed herein above for the ear tips, inflatable ear sealing structures, ear plugs, and other orifice devices to seal ear canal 9002. Ear device 9000 is illustrated outside an auricle 9004 of the ear. In general, ear device 9000 is configured to occlude or partially occlude ear canal 9002. Ear device 9000 comprises a stent 9006, a first folding member 9010, a second folding member 9012, and a stop flange 9008. In the example, stent 9006 is a tube or conduit having a proximal opening 9014 and a distal opening 9016. Stent 9006 is not limited to a single tube but can comprise a structure having one or more tubes or pathways. Stent 9006 can also made solid or having one or both openings plugged such that no pathway through stent 9006 exists. In one embodiment, stent 9006 is cylindrical in shape and flexible to conform to a torturous shape of ear canal 9002. Distal opening 9016 is exposed to ear canal 9002 when ear device 9000 is inserted in ear canal 9002. In one embodiment, stent 9006 is configured to bend after insertion to maintain an un-impeded path from proximal opening 9014 to distal opening 9016. Proximal opening 9014 as shown is exposed to an external environment outside the ear. In an example, where ear device 9000 is an ear plug for isolating the ear canal from the external environment, distal opening 9016, proximal opening 9014, or both may be closed off. Alternatively, ear device 9000 can provide the controlled delivery of acoustic information to ear canal 9002. The ear would be occluded by ear device 9000 and acoustic information can be provided by a transducer coupled to proximal opening 9014 of stent 9006. In one embodiment, a transducer can be coupled to deliver acoustic information through stent 9006 to ear canal 9002. In one embodiment, a microphone can be coupled to proximal opening 9014 of stent 9006 to retrieve acoustic information that is within ear canal 9002 for processing or delivery to an electronic device.

Optional stop flange 9008 limits a distance that ear device 9000 can be inserted into ear canal 9002. In one embodiment, stop flange 9008 is formed circumferentially around stent 9006. Stop flange 9008 has a diameter greater than ear canal 9002. The size of stop flange 9008 prevents insertion in ear canal 9002. The size and shape of stop flange 9008 can stabilize and hold ear device 9000 to the ear to prevent ear device 9000 from working itself out of ear canal 9002 due to normal activity. Stop flange 9008 blocks sound from the external environment from entering ear canal 9002. Sound will reflect off stop flange 9008 and return to the external environment. In one embodiment, stent 9006 extends proximally beyond stop flange 9008. It should be noted that stent 9006 can couple to or be formed integrally with a housing. The housing can include electronic circuitry and one or more sensors to support ear device 9000. For example, the electronic circuitry can be used to process acoustic signals, reduce noise, cancel noise, amplify a signal, moderate the amount of acoustical information the ear canal receives, or perform other functions related to the ear or the user.

In general, ear canal 9002 is occluded or partially occluded by a chamber 9018. Chamber 9018 is sealed to support attenuation of noise in the external environment from reaching ear canal 9002. Ear device 9000 comprises a first folding member 9010 and a second folding member 9012. First folding member 9010 couples to stent 9006. Second folding member 9012 also couples to stent 9006. In one embodiment, first folding member 9010 couples to stent 9006 distal to a location where second folding member 9010 couples to stent 9006. First folding member 9010 and second folding member 9012 form chamber 9018 that isolates stent 9006 from walls of ear canal 9002. In one embodiment, chamber 9018 is formed circumferentially around a portion of stent 9006 that is configured to be within ear canal 9002. Chamber 9018 is open to the external environment prior to ear device 9000 being inserted into ear canal 9002. Chamber 9018 has a diameter larger than ear canal 9002. A ring valve 9020 when open couples chamber 9018 to the external environment. In one embodiment, ring valve 9020 has an opening that extends 360 degrees around stent 9006. Ring valve 9020 is open when ear device 9000 is outside the ear canal. Ring valve 9020 can also open and close during insertion of ear device 9000 in ear canal 9002. This will be discussed in more detail herein below. Thus, when ring valve 9020 opens, a pressure within chamber 9018 will equalize to be the same as the pressure in the external environment.

In one embodiment, stent 9006 is cylindrical in shape. First folding member 9010 couples 360 degrees around stent 9006 and is located in proximity to distal opening 9016. Alternatively, first folding member 9010 can couple to stent 9006 between a distal end of stent 9006 and distal to a location where second folding member 9012 couples to stent 9006. First folding member 9010 extends proximally and overlies a portion of a surface 9022 of stent 9006. In one embodiment, first folding member 9010 has a maximum diameter or cross-sectional width that is greater than ear canal 9002. Second folding member 9012 couples to stent 9006 distal to stop flange 9008. Second folding member 9012 extends distally and overlies a portion of surface 9022 of stent 9006. In one embodiment, second folding member 9012 can have a maximum diameter or cross-sectional width greater than ear canal 9002. In one embodiment, the maximum diameter or the cross-sectional width of second folding member 9012 can have a width less than ear canal 9002. Alternatively, second folding member 9012 can extend proximally and overlie a portion of surface 9022 of stent 9006. This will be disclosed in further detail herein below. First folding member 9010 overlies at least a portion of second folding member 9012 whether second folding member 9012 extends distally or proximally.

Figure 57:
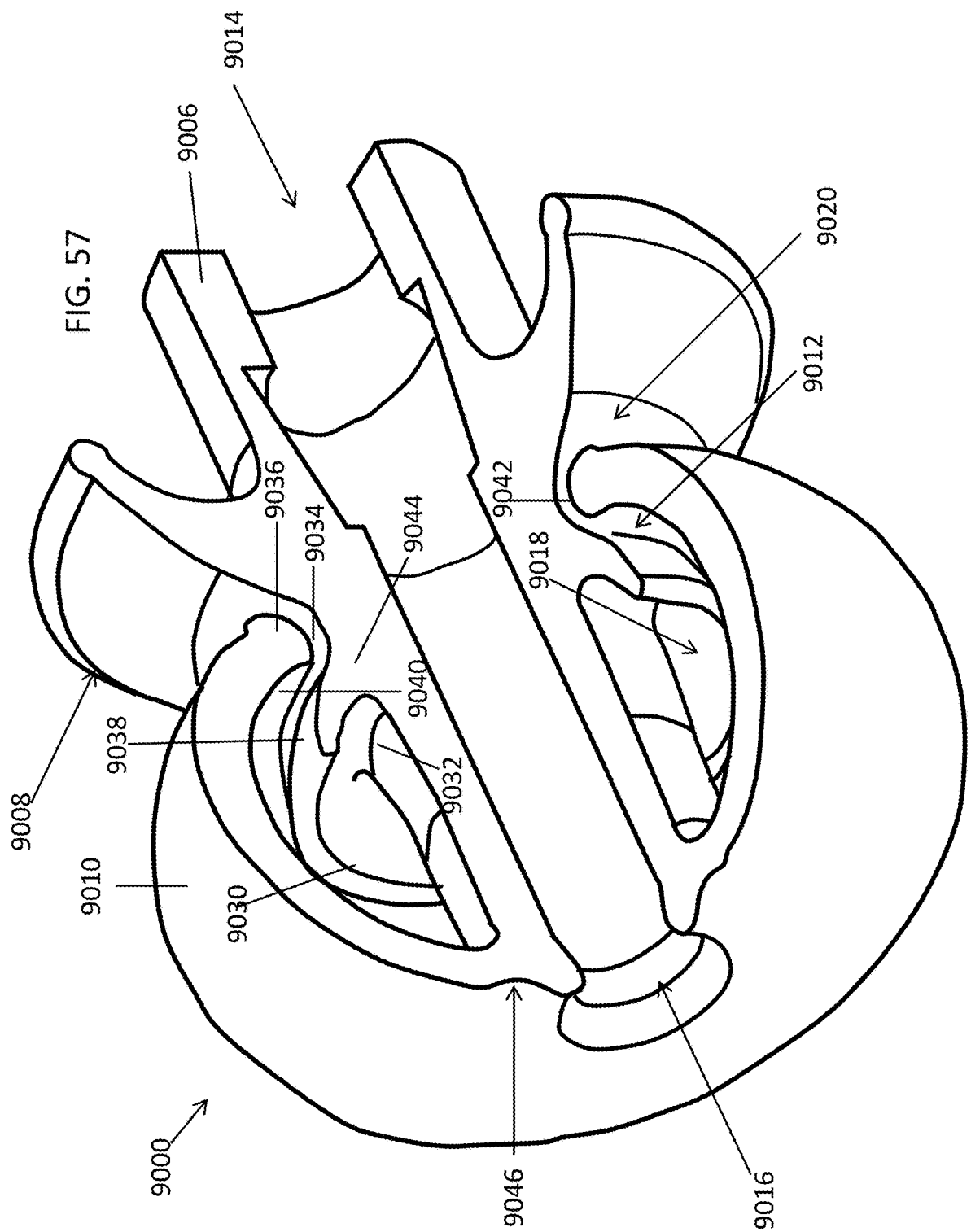
FIG. 57 is a cutaway view of the ear device in accordance with an example embodiment.

FIG. 57 is a cutaway view of ear device 9000 in accordance with an example embodiment. The cutaway view provides detail of features within ear device 9000 that cannot be seen from an external view. The structure that is cutaway in ear device 9000 is substantially equal to what is shown. Ear device 9000 comprises stent 9006, chamber 9018, and stop flange 9008. Ear device 9000 includes stent 9006 having a proximal opening 9014 and a distal opening 9016. Distal opening 9016 couples to an ear canal when ear device 9000 is inserted into the ear canal. Conversely, proximal opening 9014 couples to an external environment outside the ear as shown. In one embodiment, ear device 9000 can be used as an ear plug to isolate the ear canal from noise in the external environment. Chamber 9018 is configured to occlude or partially occlude the ear canal. Maximum attenuation occurs when chamber 9018 is a sealed volume within the ear canal. In one embodiment chamber 9018 is formed around stent 9006 such that stent 9006 is centered within the ear canal when ear device 9006 is inserted in the ear canal. Proximal opening 9014, distal opening 9016 or both can be plugged to prevent a path to the ear canal via stent 9006 thereby occluding the ear canal. Sealing of stent 9006 can comprise a cover on proximal opening 9014, distal opening 9016, or both. In a second embodiment, stent 9006 can include a valve to equalize pressure between the external environment and the ear canal to support comfort of ear device 9000. In a third embodiment, one or more lumens can be coupled through stent 9006. Proximal opening 9014 can be sealed around the one or more lumens or couple to a sealed structure. Stent 9006 acts a conduit for the one or more lumens. The one or more lumens can be used to couple one or more devices to the ear canal. In one embodiment, stent 9006 and the one or more lumens couple to a structure that is outside the ear. The structure can house electronic circuitry (e.g., processor, microphones, speakers, infrared sensors, oxygen sensors, bio sensors, pressure sensors, humidity sensors) other sensing devices. In one embodiment, the structure is sealed and insulated from the external environment such that stent 9006, chamber 9018, and the structure prevent or reduce noise from the external environment from entering the ear canal. Sealing the ear canal from the external environment reduces noise levels within the ear canal and allows information to be provided to the ear canal in a controlled manner that can be heard even if the noise level in the external environment is high. For example, a first end of a first lumen can be coupled to a transducer. A second end of the lumen can couple to the ear canal through distal opening 9016 of ear device 9000. The transducer can deliver acoustic information to the lumen which is then delivered to the ear canal. Examples of the acoustic information could be voice, music, or ambient sounds from the external environment. The delivery of the acoustic information can be provided in conjunction with the noise attenuation provided by ear device 9000.

Similarly, a first end of a second lumen can be coupled to a microphone. The second lumen then couples through stent 9006 such that the second end of the second lumen is exposed to the ear canal at the distal opening 9016 of ear device 9000. The second lumen couples sound within the ear canal to the microphone where it is converted to an electronic signal. This is useful for delivering a user's voice for transmission to a device such as a cell phone. For example, if the user of ear device 9000 is speaking, the sound of his or her voice can be picked in the ear canal. The second lumen couples to the ear canal through distal opening 9016 and delivers acoustic information within the ear canal to the microphone. The voice received from the ear canal can be more intelligible than a voice picked up with an ambient microphone in a noisy external environment. The ambient microphone would pick up the user's voice but also the noise in the external environment. Noise from the external environment is attenuated in the ear canal by chamber 9018 of ear device 9000. Thus, the user's voice can be transmitted with less background noise thereby increasing the clarity and intelligibility of the voice transmission. Alternatively, stent 9006 can be used to deliver acoustic information instead of using lumens. Moreover, more than one stent could be formed where stent 9006 is located thereby providing a plurality of channels from the ear canal to the external environment. In the example above, a first stent would couple to the transducer and a second stent would couple to the microphone.

Ear device 9000 can be molded, machined, formed, or printed. In general, ear device 9000 comprises a flexible material that will conform to the torturous shape of an ear canal. In one embodiment, ear device 9000 comprises a bio-compatible material configured for insertion in the ear canal. In the example, ear device 9000 is formed from silicone. Stop flange 9008 limits the depth of insertion of ear device 9000 into the ear canal. Note that stent 9006 extends proximally beyond stop flange 9008. Thus, a first portion of stent 9006 is placed within the ear canal and a second portion of stent 9006 is outside the ear canal. A chamber 9018 is formed around stent 9006. Chamber 9018 comprises a first folding member 9010 and a second folding member 9012. Chamber 9018 is configured to occlude or partially occlude the ear canal when ear device 9000 is inserted. In one embodiment, chamber 9018 centers stent 9006 within the ear canal. As previously mentioned, ear device 9000 is made flexible to allow stent 9006 and chamber 9018 to bend with and around curves of the ear canal.

Chamber 9018 of ear device 9000 comprises a first folding member 9010 and a second folding member 9012. At least a portion of first folding member 9010 overlies a portion of second folding member 9012. A ring valve 9020 is formed by first folding member 9010 and second folding member 9012. More specifically, ring valve 9020 is a ring-shaped opening formed by a portion of first folding member 9010 that overlies a portion of second folding member 9012. In one embodiment, ring valve 9020 couples the external environment to chamber 9018. In one embodiment, ring valve 9020 has an opening formed between first folding member 9010 and second folding member 9012. More specifically, the opening of ring valve 9020 is in a region where first folding member 9010 overlies second folding member 9012. In one embodiment, ring valve 9020 is formed 360 degrees around stent 9006. Chamber 9018 couples to the external environment since ring valve 9020 is normally open when ear device 9000 is outside the ear canal. Chamber 9018 cannot be sealed unless first folding member 9010 couples to second folding member 9012 around the entirety of stent 9006. Sealing of chamber 9018 can also occur by first folding member 9010 coupling to a combination of second folding member 9012 and a surface of stent 9006. In one embodiment, chamber 9018 is filled with gases from an external environment. In one embodiment, chamber 9018 will be at the same pressure as the external environment due to ring valve 9020 being open prior to insertion to the ear canal. A sealed chamber 9018 provides improved noise isolation between the external environment and the ear canal. Chamber 9018 can be filled with a material to further improve noise isolation or attenuation. For example, chamber 9018 can be filled with a foam, a gel, or a liquid. In one embodiment, the material within chamber 9018 can be compressible to support a wide range of volumes that can occur due to different ear canal diameters.

In one embodiment, stent 9006 is cylindrical in shape. First folding member 9010 has an anchor point 9046 that is distal to an anchor point 9044 of second folding member 9012. In the example, anchor point 9046 is located near distal opening 9016 of stent 9006. Anchor point 9046 is anchored 360 degrees around stent 9006. In one embodiment, anchor point 9046 is a pivot point. A force applied to first folding member 9010 by a wall of the ear canal will move first folding member 9010 towards stent 9006 pivoting at anchor point 9046. The force will move first folding member 9010 to couple to the second folding member 9012 thereby sealing chamber 9018. First folding member 9010 comprises a vertical component and a horizontal component. The vertical component of first folding member 9010 suspends first folding member 9010 above second folding member 9012 and stent 9006. The horizontal component of first folding member 9010 extends first folding member 9010 to the first predetermined proximal location. First folding member 9010 terminates having a proximal end 9036 that overlies second folding member 9012 or stent 9006. The horizontal and vertical components of first folding member 9010 can be combined such that first folding member 9010 is changing horizontally and vertically towards the first predetermined proximal location. In one embodiment, first folding member 9010 can have a curved shape. The curved shape supports insertion in the ear canal and minimizes long-term discomfort. In one embodiment, the curved shape of first folding member 9010 can minimize the surface area of first folding member 9010 coupling to the wall of the ear canal. In one embodiment, an external surface of first folding member 9010 is configured to conform to the shape of the ear canal as ear device 9000 is inserted in the ear canal. The walls of the ear canal applies a pressure 360 degrees around first folding member 9010 during insertion. The curved shape of first folding member 9010 also supports coupling to second folding member 9012 to seal chamber 9018. In one embodiment, second folding member 9012 will have a curved shape that corresponds to or is similar to the curved shape of first folding member 9010 to support coupling and sealing of chamber 9018. In one embodiment, first folding member 9010 is more than a hemisphere in shape but less than a full sphere. In one embodiment, first folding member 9010 will have a diameter maximum or a distance maximum from stent 9006 that is between anchor point 9046 and the proximal end of first folding member 9010. In one embodiment, an angle 9030 is formed between stent 9006 and first folding member 9010. Angle 9030 supports insertion into the ear canal. Angle 9030 is typically less than 90 degrees when ear device 9000 is outside the ear. In one embodiment, angle 9030 is 60 degrees or less when ear device 9000 is outside the ear.

In the example embodiment, stent 9006 is cylindrical in shape. Second folding member 9012 has an anchor point 9044 that is proximal to an anchor point 9046 of first folding member 9010. In the example, anchor point 9044 is located near stop flange 9008 of ear device 9000. Anchor point 9044 is anchored 360 degrees around stent 9006. In one embodiment, anchor point 9044 is a pivot point. As shown, second folding member 9012 extends from anchor point 9044 distally such that second folding member 9012 overlies a portion of stent 9006 between anchor point 9044 of second folding member 9012 and anchor point 9046 of first folding member 9010. Alternatively, second folding member 9012 can extend from anchor point 9044 proximally such that second folding member 9012 overlies a portion of stent 9006 between anchor point 9044 of second folding member 9012 and stop flange 9008. First folding member 9010 overlies a portion of second folding member 9012 whether extending distally or proximally over stent 9006.

Second folding member 9012 comprises a vertical component and a horizontal component. The vertical component of second folding member 9012 suspends second folding member 9012 above stent 9006. The horizontal component of second folding member 9012 extends second folding member 9012 to a predetermined location distally or alternatively a predetermined location proximally overlying stent 9006. The horizontal and vertical components of second folding member 9012 can be combined such that second folding member 9012 is changing horizontally and vertically towards the predetermined location. In one embodiment, second folding member 9012 forms an angle 9032 with stent 9006 to suspend second folding member 9012 over stent 9006. In one embodiment, angle 9032 can be 30 degrees to 150 degrees. In the example, angle 9032 is less than 90 degrees. In one embodiment, second folding member 9012 can have a curved shape. In one embodiment, second folding member 9012 can have a curved shape corresponding to the curved shape of first folding member 9010 that overlies second folding member 9012.

A force applied to a surface 9038 of second folding member 9012 will produce movement of second folding member 9012 towards stent 9006. In one embodiment, second folding member is configured to flex and conform. In general, an interior surface 9040 of first folding member 9010 is configured to couple to surface 9038 of second folding member 9012 during insertion of ear device 9000 into the ear canal. In one embodiment, surface to surface coupling between first folding member 9010 and second folding member 9012 seals chamber 9018. Second folding member 9012 is configured to move towards stent 9006 as a force is applied by first folding member 9010. Second folding member 9012 pivots at anchor point 9044 as second folding member 9012 folds towards stent 9006.

Figure 58:
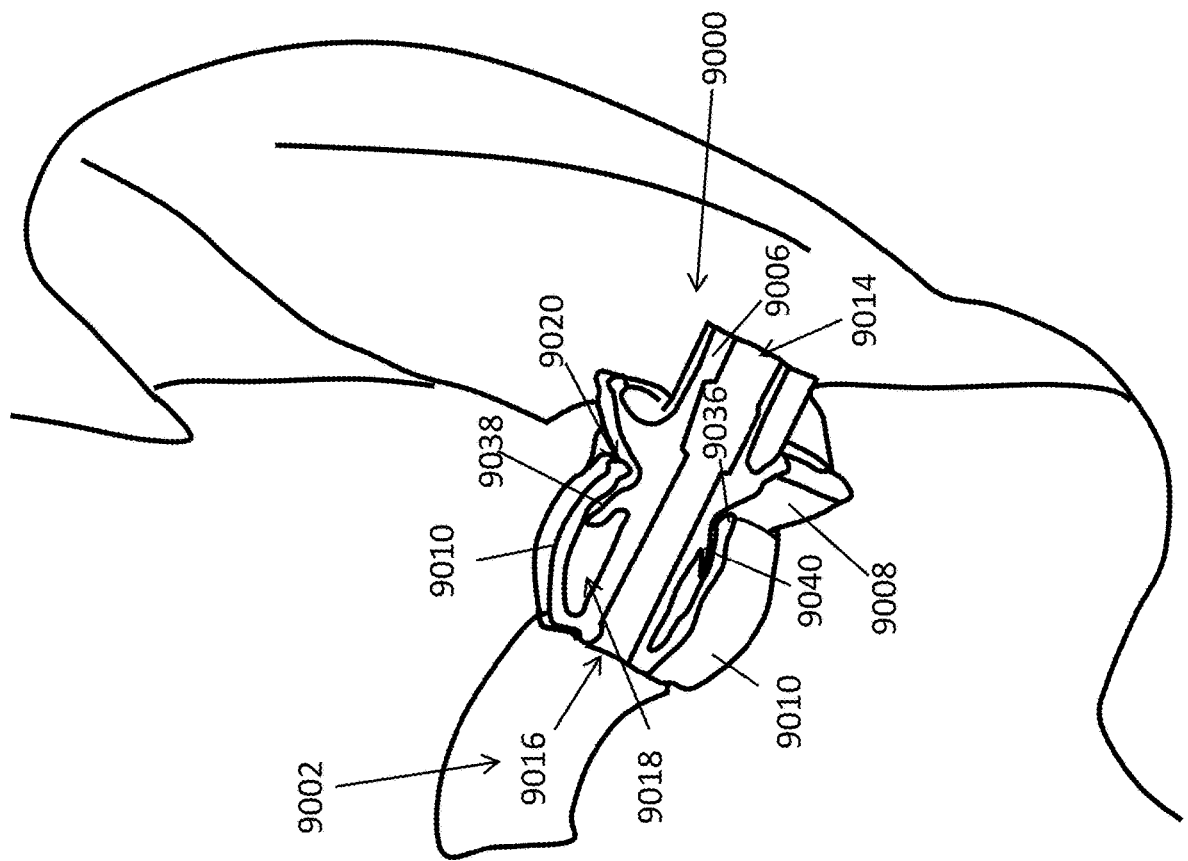
FIG. 58 is an illustration of the ear device inserted in the ear canal in accordance with an example embodiment.

FIG. 58 is an illustration of ear device 9000 inserted in ear canal 9002 in accordance with an example embodiment. FIG. 58 is a cutaway view of ear device 9000 to illustrate internal structure of ear device 9000. More specifically the view shows chamber 9018 being sealed and occluding or partially occluding the ear canal. The section of ear device 9000 that is cutaway is substantially equal to the structure shown in the figure. First folding member 9010 has a diameter larger than ear canal 9002. Inserting ear device 9000 into ear canal 9002 applies a force to first folding member 9010 that motivates first folding member to move towards second folding member 9012. Referring briefly to FIG. 57, angle 9030 of first folding member 9010 is reduced upon insertion into ear canal 9002. First folding member 9010 also conforms to a shape of ear canal 9002. In one embodiment, first folding member 9010 couples to the walls of the ear canal around it's entirety such that there is no gap between first folding member 9010 and the walls of the ear canal coupling the external environment to the ear canal. First folding member 9010 couples to second folding member 9012 to seal chamber 9018. Ear canal 9002 applies a pressure or force 360 degrees around first folding member 9010. In the example, surface 9038 of second folding member 9012 couples to surface 9040 of first folding member 9010. More specifically, surface 9038 of second folding member 9012 couples to surface 9040 of first folding member 9010, 360 degrees around stent 9006 such that chamber 9018 is sealed when ear device 9000 is inserted in the ear canal. This corresponds to ring valve 9020 being closed. Chamber 9018 is not sealed if any portion of surface 9038 of second folding member 9012 does not couple to a corresponding surface 9040 of first folding member 9010. This corresponds to ring valve 9020 being open. Sealing chamber 9018 provides maximum noise attenuation or ear canal isolation from an external environment. In the example, noise from the external environment is attenuated by stop flange 9008 and chamber 9018. The only other path for noise to couple to ear canal 9002 is through stent 9006 or between first folding member 9010 and the walls of the ear canal. As mentioned previously, any acoustic information coupling through stent 9006 is controlled. In one embodiment, stent 9006 can be plugged at distal port 9016, proximal port 9014, or both. In one embodiment, stent 9006 can be made solid or filled to prevent the transfer of acoustic information to ear canal 9002. An alternate embodiment for sealing ring valve 9020 has proximal end 9036 of first folding member 9010 coupling to stent 9006 or surface 9038 of second folding member 9012. Ring valve 9020 would also seal if proximal end 9036 coupled a complete 360 degrees around stent 9006.

Figure 59:
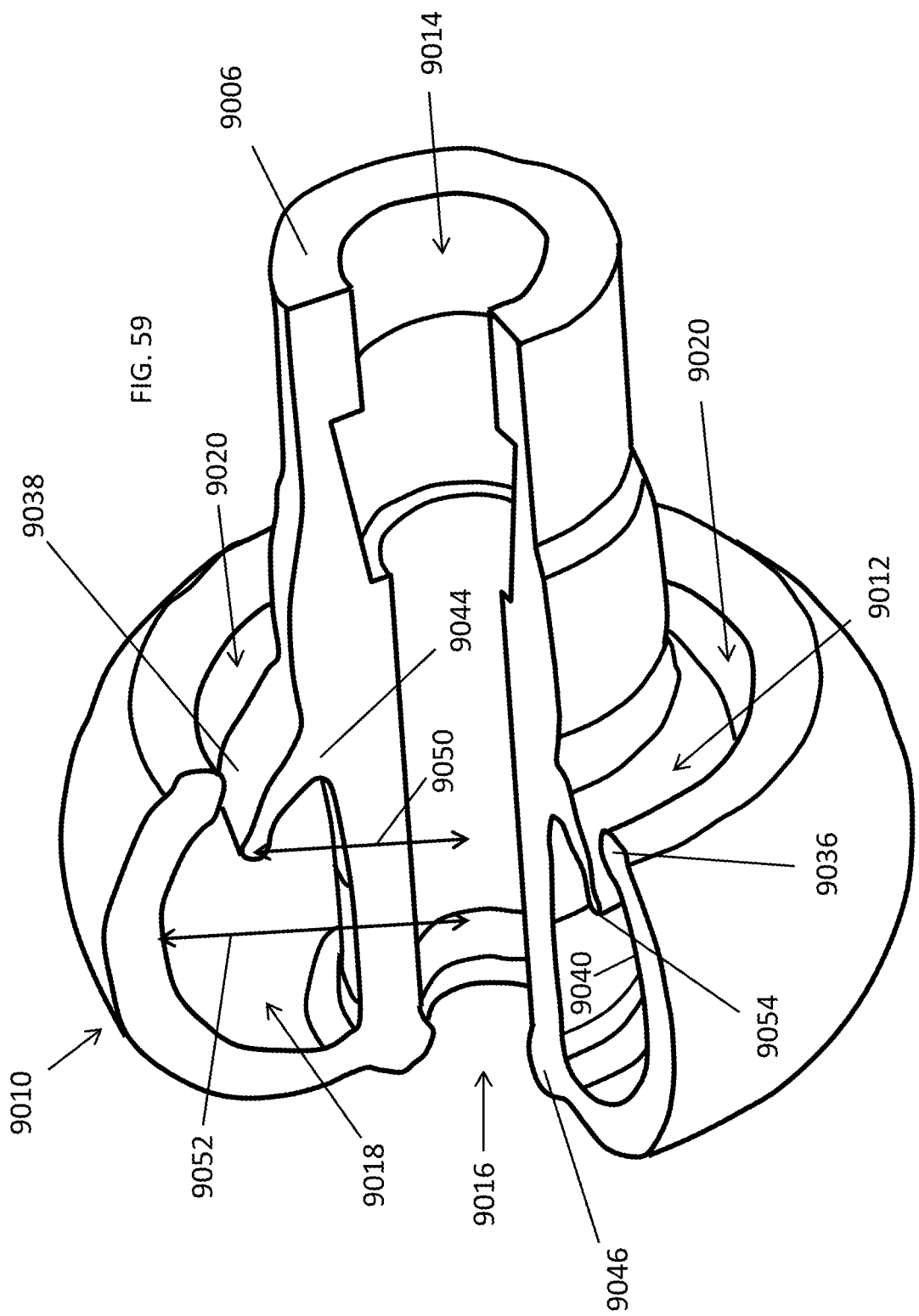
FIG. 59 is a cutaway view of the ear device without a stop flange in accordance with an example embodiment.

FIG. 59 is a cutaway view of ear device 9000 without a stop flange in accordance with an example embodiment. In the example, ear device 9000 is cutaway to illustrate chamber 9018 and ring valve 9020. The structure that is cutaway is substantially equal to the structure of ear device 9000 that is shown in the figure. Stop flange is removed to better view ring valve 9020. Ring valve 9020 has an opening that couples into chamber 9018. In one embodiment, the opening in ring valve 9020 is a 360-degree slot around stent 9006. Thus, the 360 degree slot around stent 9006 appears as a ring shaped opening. Chamber 9018 is a volume that is formed around stent 9006 that is defined by first folding member 9010 and second folding member 9012. As shown, ring valve 9020 is in an open state such that the external environment is coupled to chamber 9018. Ring valve 9020 is in the open state when a gap occurs anywhere in the 360-degree slot around stent 9006. The gap couples the external environment to chamber 9018. Conversely, ring valve 9020 is closed when first folding member 9010 couples to second folding member 9012 whereby chamber 9018 is isolated from the external environment. In one embodiment, first folding member 9010 forms a 360-degree seal to second folding member 9012 that decouples the ear canal from the external environment by chamber 9018.

A double-sided arrow 9050 illustrates a distance from a center of stent 9006 to second folding member 9012. A double-sided arrow 9052 illustrates a distance from a center of stent 9006 to first folding member 9010. As mentioned previously, a portion of first folding member 9010 overlies a portion of second folding member 9012. First folding member 9010 will couple to second folding member 9012 when the portion of first folding member 9010 overlying the portion of second folding member 9012 is moved from the distance 9052 to the distance 9050 or less. In one embodiment, stent 9006 is cylindrical in shape. In one embodiment, second folding member 9012 has a curved shape extending from anchor point 9044 to a distal end 9054 of second folding member 9012. In one embodiment, distal end 9054 is circular in shape having a radius equal to the distance of double-sided arrow 9050. In one embodiment, first folding member 9010 has a curved shape extending from anchor point 9046 to proximal end 9036 of first folding member 9010. In one embodiment, the portion of first folding member 9010 overlying the portion of second folding member 9012 can have a similar rate of curvature to prevent coupling of the first folding member 9010 to second folding member 9012 when ear device 9000 is in a quiescent state (e.g. outside the ear canal). In one embodiment, the gap between the portion of first folding member 9010 overlying the portion of the second folding member 9012 is approximately constant around stent 9006.

Figure 60:
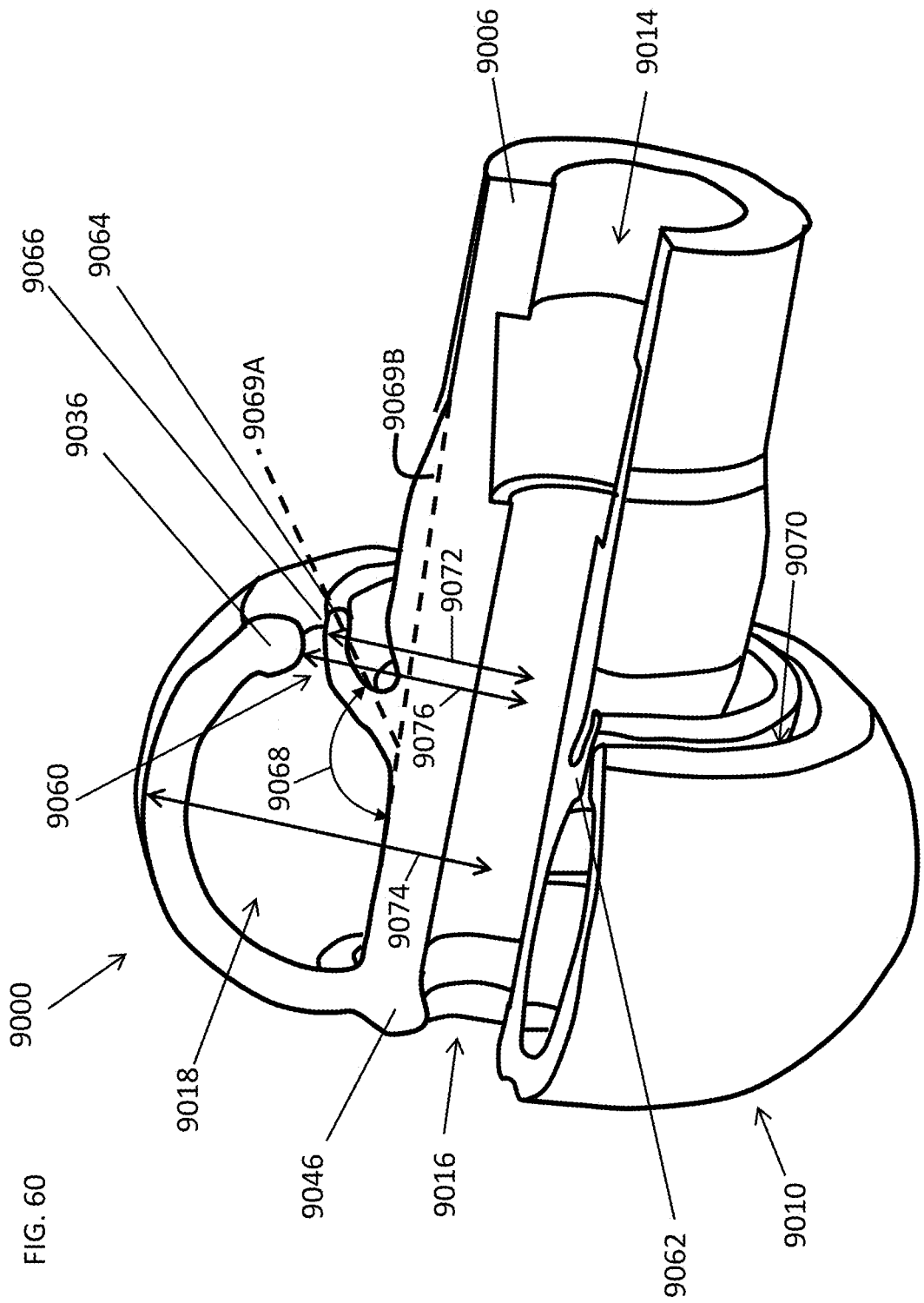
FIG. 60 is a cutaway view of an ear device without a stop flange in accordance with an example embodiment.

FIG. 60 is a cutaway view of an ear device 9000 without a stop flange in accordance with an example embodiment. The cutaway view removes a portion of ear device 9000 to illustrate structure that cannot be seen with an external view. The portion that is removed is substantially equal to the structure that is shown in the figure. The optional stop flange is removed to view ring valve 9020. In general, ear device 9000 can have a stop flange as shown in FIGS. 56-58 to limit insertion in an ear canal. Ear device 9000 is configured to occlude or partially occlude an ear canal of an ear. Chamber 9018 of ear device 9000 is configured to be inserted in the ear canal. As shown, stent 9006 is a passageway that can be used to deliver acoustic information or receive acoustic information from the ear canal. Stent 9006 can also be used to equalize pressure between the external environment and the ear canal. Typically, a proximal end of stent 9006 couples to an enclosure that is outside the ear. Proximal opening 9014 of stent 9006 is a pathway of stent 9006 to an interior of the enclosure. The enclosure can house electronic circuitry, transducers, sensors, valves, a power supply, and other devices (e.g., earphones, hearing aids). In one embodiment, the enclosure is sealed and insulated such that the external environment is not coupled to the ear canal through stent 9006.

Acoustic information can be transferred through stent 9006 itself or stent 9006 can be a conduit to channel one or more lumens or electronics to the ear canal. For example, a first and a second lumen can be placed within stent 9006. The distal end of the first lumen is exposed to the ear canal. Similarly, the second lumen is exposed to the ear canal. Typically, the distal ends of the first and second lumens would be placed at or near distal opening 9016 of ear device 9000. A microphone can be coupled to a proximal end of the first lumen for receiving acoustic information in the ear canal. A transducer can be coupled to the proximal end of a second lumen for delivering acoustic information to the ear canal. The microphone and transducer would be coupled to electronic circuitry in the housing (coupled to stent 9006) or located somewhere outside the ear.

Chamber 9018 comprises first folding member 9010 and second folding member 9060. First folding member 9010 and second folding member 9060 form ring valve 9070. As mentioned previously chamber 9018 is configured to occlude or partially occlude the ear canal of the ear. The orientation of second folding member 9060 differs from second folding member 9012 as disclosed in FIG. 59. Second folding member 9060 performs the same function as second folding member 9012. In fact, any feature stated herein for second folding member 9012 also applies to second folding member 9060 and vice versa. An anchor point 9062 of second folding member 9060 is between anchor point 9046 of first folding member 9010 and the stop flange (not shown). Second folding member 9060 extends from anchor point 9062 proximally such that second folding member 9060 overlies stent 9006. A portion of first folding member 9010 overlies a portion of second folding member 9010. In one embodiment, second folding member 9060 can be formed having a portion that extends vertically from anchor point 9062 and horizontally above stent 9006 in a proximal direction. In one embodiment, second folding member 9060 can be formed as a curved structure that changes vertically and horizontally. Second folding member 9060 has a proximal end 9064 that terminates before the stop flange (not shown). In one embodiment, second folding member 9060 is curved to suspend second folding member 9060 above stent 9006. In one embodiment, second folding member 9060 forms an angle 9068 with stent 9006 (e.g., line 9069B). Angle 9068 (e.g., between line 9069A and line 9069B) is typically greater than 90 degrees. In one embodiment, angle 9068 is 120 degrees or greater. If angle 9068 is less than 90 degrees it will be an implementation of second folding member 9012 as disclosed in FIG. 59.

An opening of ring valve 9070 comprises a distance between proximal end 9036 of first folding member 9010 and proximal end 9064 of second folding member 9012. In one embodiment, stent 9006 is a cylinder that can be an open channel or a filled structure that has no path from the external environment to the ear canal. As mentioned previously, second folding member 9060 has an anchor point 9062 that couples to stent 2006 or is formed part of stent 2006. In the example, second folding member 9060 extends proximally forming a curved structure suspended above stent 9006. The curved structure of second folding member 9060 is formed 360 degrees around stent 9006. In the example, proximal end 9064 of second folding member 9060 can be seen as circular in shape around stent 9006. Proximal end 9064 forms the circle having a radius indicated by double sided arrow 9072 from the center of stent 9006.

First folding member 9010 is a curved structure extending from anchor point 9046 to proximal end 9036 suspended above stent 9006. The curved structure is formed 360 degrees around stent 9006. A portion of first folding member 9010 overlies a portion of second folding member 9060. In the example, proximal end 9036 of first folding member 9010 can be seen as circular in shape around stent 9006. Proximal end 9036 forms the circle having a radius indicated by double sided arrow 9076 from the center of stent 9006. In one embodiment, a width of an opening of ring valve 9070 is approximately the distance of double-sided arrow 9076 less the distance of double-sided arrow 9072 when ear device 9000 is not inserted in the ear canal. In one embodiment, first folding member 9010 has a maximum radius as indicated by double sided arrow 9074. In one embodiment, the maximum radius is located distally from proximal end 9036. The maximum radius of first folding member 9010 is greater than a radius of the era canal. As shown, ear device 9000 is outside the ear canal in a quiescent state where ring valve 9070 is open and chamber 9018 is coupled to the external environment. Chamber 9018 can be filled with a compressible material to further attenuate noise from the external environment. In one embodiment, filling chamber 9018 would also improve noise attenuation when chamber 9018 is open to the external environment.

Figure 61:
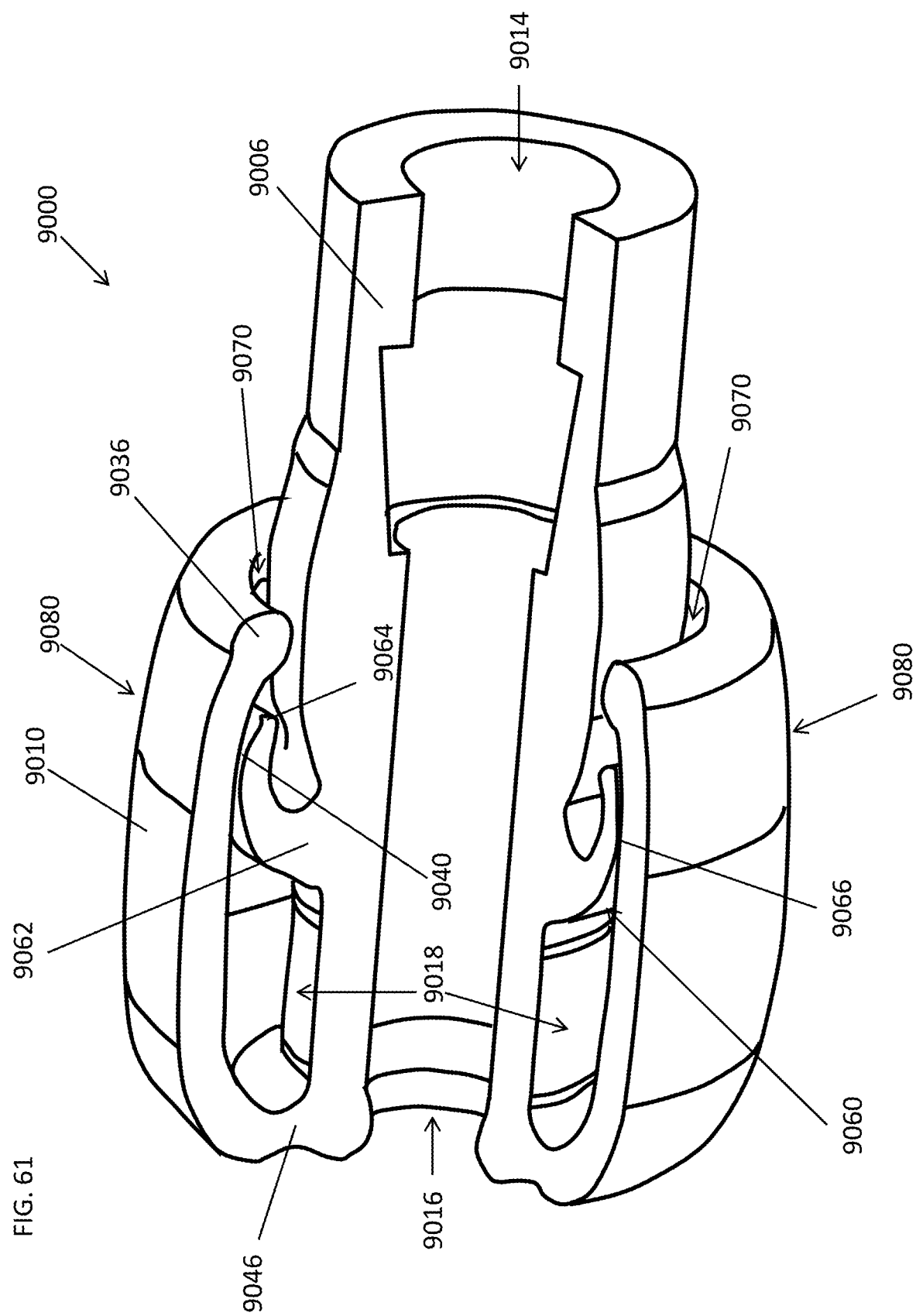
FIG. 61 is a cutaway view of the ear device with a chamber sealed in accordance with an example embodiment.

FIG. 61 is a cutaway view of ear device 9000 with chamber 9018 sealed in accordance with an example embodiment. The cutaway view illustrates structure within ear device 9000 that could not be seen with an external view. The section of ear device 9000 that is cutaway is substantially equal to what is shown in the illustration. Ear device 9000 has an optional stop flange removed to illustrate chamber 9018 being sealed. Ring valve 9070 is shown sealed thereby sealing chamber 9018 for occluding or partially occluding the ear canal with ear device 9000. In general, a force will be applied to ear device 9000 when inserted in an ear canal of an ear. More specifically, the wall of the ear canal applies a force to first folding member 9010. Referring briefly to FIG. 60, the ear canal radius will be smaller than the maximum radius indicated by double sided arrow 9074. Twice the distance of double-sided arrow 9074 is a maximum diameter of ear device 9000. The ear canal having a radius less than double-sided arrow 9074 of FIG. 60 will apply a force 360 degrees around first folding member 9010 that folds first folding member 9010 towards stent 9006. First folding member 9010 is flexible and supports folding when inserted into the ear canal such that little or no discomfort occurs. First folding member 9010 conforms and couples to the wall of the ear canal. No gap will exist between a surface of first folding member 9010 and the wall of the ear canal that couples the external environment to the ear canal. Chamber 9018 is sealed when first folding member 9010 couples to second folding member 9060. In one embodiment, chamber 9018 is sealed when first folding member 9010 couples to second folding member 9060 a full 360 degrees around stent 9006 such that no gap exists between first folding member 9010 and second folding member 9060. Sealing chamber 9018 isolates the ear canal from the external environment thereby attenuating noise from the external environment from reaching the ear canal. Ear device 9000 occludes or partially occludes the ear canal when chamber 9018 is sealed in the ear canal and stent 9006 does not couple to the external environment. In one embodiment, noise or sound is reflected by the stop flange (not shown) away from the ear canal and back into the external environment. Noise that reaches an entrance to the ear canal is blocked by sealed chamber 9018. Note that any noise would have to couple through one of first folding member 9010, second folding member 9060, and chamber 9018 to reach the ear canal. Attenuation properties of ear device 9000 can be improved by filling chamber 9018 with a gas, liquid, or foam that supports sound suppression. In one embodiment, chamber 9018 can be filled with a compressible material that supports noise attenuation. Thus, ear device 9000 provides excellent noise attenuation from the external environment. As disclosed herein above, stent 9006 can be used to deliver acoustic information to the ear canal or receive acoustic information from the ear canal. This can be useful for an application such as two-way communication in a noisy environment or listening to music in a noisy environment.

In one embodiment, a pressure within chamber 9018 is approximately equal to a pressure in the external atmosphere when chamber 9018 is sealed. Referring briefly to FIG. 60, chamber 9018 of ear device 9000 is exposed to the external environment when chamber 9018 is not sealed. The pressure within chamber 9018 would be the same as the pressure within the external environment. Upon inserting ear device 9000 into an ear canal a force is applied around first folding member 9010 that moves first folding member towards second folding member 9012. The wall of the ear canal provides a force 360 degrees around first folding member 9010. First folding member 9010 is flexible and provides little resistance in folding to fit the diameter of the ear canal. Chamber 9018 is then sealed when first folding member 9010 couples to second folding member 9060 whereby no gap exists to the external environment through ring valve 9070.

Chamber 9018 maintains approximately equal pressure with the external atmosphere by opening ring valve 9070 during an adjustment that changes the ear canal diameter whether the diameter of the ear canal increases or decreases thereby respectively increasing or decreasing the volume of chamber 9018. In one embodiment, first folding member 9018 and second folding member 9060 are configured to decouple when a change in volume occurs. For example, chamber 9018 being inserted into a region of the ear canal that has a reduced diameter will reduce volume within chamber 9018 and expel an amount of gas corresponding to a difference in volume from the prior larger volume of chamber 9018 to the smaller volume of chamber 9018 due to the reduced diameter of the ear canal. Thus, although the volume is reduced in chamber 9018, the pressure within chamber 9018 stays approximately equal to the external environment due to the expelled gas volume. Ring valve 9070 seals after adjustment to the change in volume within the ear canal thereby maintaining the noise attenuation properties of ear device 9000. Comfort is maintained as the pressure applied to the walls of the ear canal stays the same. In one embodiment, the flexibility of first folding member 9010 and second folding member 9060 is such that second folding member 9060 can fold to couple to stent 9006. Similarly, first folding member 9010 can fold to couple to second folding member 9060 (while second folding member 9060 couples to stent 9006) such that the volume within 9018 is reduced to a minimum and thereby accommodate small diameter ear canals. Alternatively, if the ring valve 9070 does not open and expel gas during a decrease in volume of chamber 9018 the pressure within chamber 9018 will increase. This may have an effect on comfort due to increase pressure on the walls of the ear canal and also noise attenuation.

Chamber 9018 also maintains approximately equal pressure with the external atmosphere by opening ring valve 9070 during an adjustment that changes the ear canal diameter from a smaller diameter to a larger diameter thereby increasing the volume of chamber 9018. In one embodiment, first folding member 9018 and second folding member 9060 are configured to decouple when the increase in volume occurs. For example, chamber 9018 being inserted into a region of the ear canal that increases in diameter will increase the volume within chamber 9018 and allow an amount of gas into chamber 9018 from the external environment that corresponds to a difference in volume from the prior smaller volume of chamber 9018 and the larger volume of chamber 9018 due to the increased diameter of the ear canal. First folding member 9010 and second folding member 9012 fold outward toward the larger diameter wall of the ear canal, decouples, and then seals. Thus, although the volume is increased in chamber 9018, the pressure within chamber 9018 stays approximately equal to the external environment due ring valve 9070 opening to the external environment. Ring valve 9070 seals after adjustment to the change in volume within the ear canal thereby maintaining the noise attenuation properties of ear device 9000. Comfort is maintained as the pressure applied to the walls of the ear canal stays the same. In one embodiment, the resilience of first folding member 9010 and second folding member 9060 is such that first folding member 9010 will change shape towards the shape disclosed in FIG. 60 when ear device 9000 is not inserted in the ear canal thereby expanding to the increased diameter of the ear canal. Similarly, second folding member 9060 will also change shape towards the shape disclosed in FIG. 60 when ear piece 9000 is not inserted in the ear canal thereby expanding to the increased diameter of the ear canal. Ring valve 9070 will open during the transition to an increased ear canal diameter thereby exposing chamber 9018 to the external environment. Ring valve 9070 closes after the adjustment to the increased diameter and the pressure within chamber 9018 is approximately equal to the pressure in the external environment. Comfort is maintained as the pressure applied to the walls of the ear canal by ear device 9000 independent of the diameter of the ear canal. The attenuation properties are also maintained as ring valve 9070 is sealed after insertion and adjustment within the ear canal.

FIG. 62 is a block diagram 9080 of a method for occluding or partially occluding an ear canal with an ear device in accordance with an example embodiment. Block diagram 9080 comprises one or more steps. A step order is not implied, can be practiced in any sequence, and one or more steps can be removed from the sequence to practice the invention. In a step 9082, an ear device is inserted into an ear canal of an ear. The ear device has a chamber configured to occlude or partially occlude the ear canal. The ear device comprises at least one stent and the chamber. The chamber is formed around the at least one stent. A ring valve couples to the chamber for coupling to an external environment. The ring valve has an opening 360 degrees around the at least one stent.

In a step 9084, closing the ring valve seals the chamber thereby isolating the ear canal from the external environment. The ring valve is configured to close when inserted in the ear canal. Thus, occluding or partially occluding the ear canal. A force is applied to the ring valve or the chamber to seal the ring valve. The force applied closes the opening of the ring valve thereby sealing the chamber. In one embodiment, the opening of the ring valve is 360 degrees around the at least one stent. Thus, to seal the chamber the ring valve seals the opening 360 degrees around the at least one stent.

In at step 9086, the ring valve comprises a first folding member overlying a second folding member. The ring valve is open prior to being inserted in the ear canal. Thus, the ring valve couples the external environment to the chamber. The ear canal is configured to apply a force that closes the opening of the ring valve 360 degrees around the at least one stent to seal the chamber thereby closing the ring valve.

In a step 9088, the ring valve opens when the ear device is removed from the ear. In a step 9090, the ring valve opens as the ear device is being inserted in the ear canal to support adjustment of the chamber volume to a change in diameter of the ear canal. In a step 9092, the pressure is adjusted within the chamber. The chamber is configured to maintain a pressure approximately equal to the external environment as the chamber volume changes. In a step 9094, the ring valve opens as the volume of the chamber changes thereby coupling the chamber to the external environment through the ring valve. The pressure in the chamber then equalizes to a pressure in the in the external environment. The ring valve opens in response to a change in the diameter of the ear canal which results in an adjustment of the chamber volume.

Figure 63:
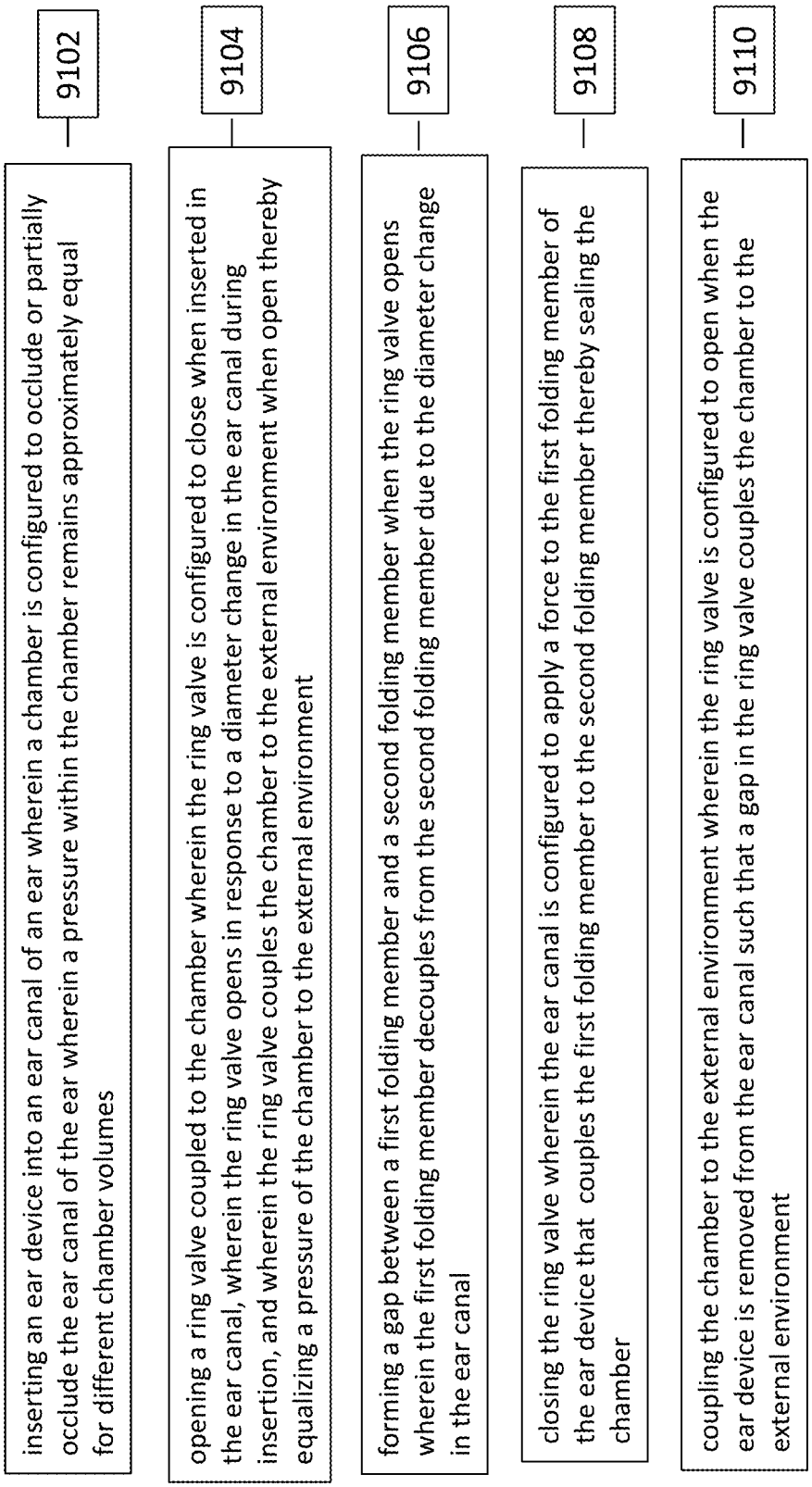
FIG. 63 is a block diagram of a method for occluding or partially occluding an ear canal with a chamber of an ear device in accordance with an example embodiment.

FIG. 63 is a block diagram 9100 of a method for occluding or partially occluding an ear canal with a chamber of an ear device in accordance with an example embodiment. The block diagram 9100 comprises one or more steps. A step order is not implied, can be practiced in any sequence, and one or more steps can be removed from the sequence to practice the invention. In a step 9102, an ear device is inserted into an ear canal of an ear. A chamber of the ear device is configured to occlude or partially occlude the ear canal of the ear. In one embodiment, a pressure within the chamber remains approximately equal for different chamber volumes.

In a step 9104, a ring valve of the ear device is open prior to inserting the ear device into the ear canal. The ring valve couples the external environment to the chamber. The ring valve is configured to close when inserted in the ear canal. The ring valve is configured to open in response to a diameter change in the ear canal during insertion that causes the chamber to increase in size or be reduced in size to occlude or partially occlude the ear canal. Opening the ring valve during insertion couples the chamber to the external environment thereby equalizing a pressure within the chamber to the external environment. Thus, the pressure within the chamber is approximately equal to the pressure in the external environment for any chamber size in the ear device.

In a step 9106, a gap is formed between a first folding member and a second folding member when the ring valve opens. In one embodiment, the ring valve comprises a portion of the first folding member overlying a portion of the second folding member. The first folding member can be formed around a stent. Similarly, the second folding member can be formed around a stent. Under quiescent conditions such as when the ear device is outside the ear a gap will exist between the first and second folding members such that the ring valve is open. In one embodiment, the first folding member decouples from the second folding member due to a diameter change in the ear canal forming an opening in the ring valve.

In a step 9108, the ear canal is configured to apply a force to the first folding member of the ear device that couples the first folding member to the second folding member. The ring valve closes when the first folding member couples to the second folding member such that no gaps exist coupling the chamber to the external environment. Thus, the chamber is sealed. In a step 9110, the chamber is coupled to the external environment. The ring valve is configured to open when the ear device is removed from the ear canal. The ring valve opens such that a gap in the ring valve couples the chamber to the external environment.

FIG. 64 is a block diagram 9120 of a method for occluding or partially occluding an ear canal with a chamber of an ear device in accordance with an example embodiment. The block diagram 9120 comprises one or more steps. A step order is not implied, can be practiced in any sequence, and one or more steps can be removed from the sequence to practice the invention. In a step 9122, an ear canal of an ear is occluded or partially occluded with an ear device. The ear canal is occluded or partially occluded by a chamber that is sealed. In one embodiment, the chamber is normally open to the external environment. In the normally open configuration, the chamber of the ear device is coupled to the external environment. The process of inserting the ear device into the ear canal of the ear seals the chamber thereby isolating the ear canal from the external environment.

In a step 9124, the chamber is coupled to the external environment or decoupled from the external environment by a ring valve. Walls of the ear canal are configured to apply a force to the ring valve. The force applied by the walls of the ear canal to the ring valve closes the ring valve thereby sealing the chamber that occludes or partially occludes the ear canal. In a step 9126, pressure within the chamber is equalized to the external environment. In one embodiment, the ring valve opens in a response to a change in a diameter of the ear canal during insertion of the ear device. The ring valve couple the chamber of the ear device to the external environment thereby equalizing a pressure within the chamber to the external environment as the chamber adapts to the diameter of the ear canal. The change in the diameter of the ear canal during insertion of the ear device into the ear canal corresponds to a change in the volume of the chamber to occlude or partially occlude the ear canal.

In a step 9128, a force is applied 360 degrees around the ring valve to close the ring valve and thereby seal the chamber. In one embodiment, the walls of the ear canal of the ear apply a force 360 degrees around the ring valve. The force applied 360 degrees on the ring valve by the ear canal closes the ring valve thereby isolating the ear canal from the external environment.

Referring briefly to FIG. 56 and FIG. 60, an ear device is shown comprising a stent 9006, a first folding member 9010, and a second folding member 9012. Alternatively, a second folding member can be oriented as disclosed in FIG. 60 as second folding member 9060. First folding member 9010 forms a chamber with either second folding member 9012 or second folding member 9060. First folding member 9010 couples to stent 9006 and extends proximally. A major portion of first folding member 9010 overlies a portion of stent 9006.

Second folding member 9012 or second folding member 9060 couples to stent 9006. First folding member 9010 overlies second folding member 9012 or second folding member 9060. In one embodiment, a portion of first folding member 9010 overlies a portion of second folding member 9012 or second folding member 9060. The first folding member 9010 couples to the second folding member 9012 or second folding member 9060 when inserted in the ear canal of an ear as indicated in FIGS. 58 and 61. First folding member 9010 and second folding member 9012 form a chamber 9018 as disclosed in FIG. 58 when inserted in the ear canal to occlude or partially occlude the ear canal. Similarly, first folding member and second folding member 9060 form a chamber 9018 as disclosed in FIG. 61 when inserted in the ear canal to occlude or partially occlude the ear canal. Chamber 9018 couples to and is formed around stent 9006.

Referring to FIG. 57, first folding member 9010 is shown coupling circumferentially to stent 9006. Similarly, second folding member 9012 couples circumferentially to stent 9006. Note that first folding member 9010 couples to stent 9006 distal to where second folding member 9012 couples to stent 9006. Referring briefly to FIG. 60, second folding member 9060 couples circumferentially to stent 9006. In one embodiment, a stop flange 9008 couples to stent 9006. Stop flange 9008 limits how far ear device 9000 can be inserted into the ear canal. In one embodiment, stop flange 9008 is larger than the diameter of the ear canal. Stop flange 9008 is located proximally in relation to first folding member 9010 and second folding member 9012 or second folding member 9060. In one embodiment, first folding member 9010 and second folding member 9012 or second folding member 9060 form a valve. In one embodiment, they form a ring valve. The valve couples chamber 9018 to the external environment.

Referring briefly to FIG. 59, a ring valve 9020 is illustrated. Ring valve 9020 is normally open. In one embodiment ring valve 9020 has a gap that is circular or ring shaped around stent 9006. Ring valve 9020 comprises a portion of first folding member 9010 overlying a portion of second folding member 9012. The gap is the distance between the overlying portions of first folding member 9010 and second folding member 9012. Similarly, ring valve 9020 can comprise a portion of first folding member 9010 overlying a portion of second folding member 9060. The gap is the distance between the overlying portions of first folding member 9010 and second folding member 9060.

Referring briefly to FIG. 57, first folding member 9010 is configured to fold towards stent 9006 during insertion of the ear device into the ear canal. First folding member 9010 is configured to be flexible to bend, fold, conform. First folding member 9010 is low friction for easily being inserted into the ear canal. First folding member 9010 has a diameter that is greater than a diameter of the ear canal. First folding member 9010 has an anchor point 9046 that is a pivot point to support folding, bending, or conforming to a shape of the ear canal. In one embodiment, at least a portion of the outer surface of first folding member 9010 is configured to couple to and conform to a surface of the ear canal. Note that a force applied by walls of the ear canal to an exterior surface of first folding member 9010 will move first folding member 9010 towards stent 9006 and thereby second folding member 9012 or second folding member 9060.

Referring briefly to FIG. 61, the second folding member 9060 or second folding member 9012 is configured to flex or fold. As shown in FIG. 61, a force 9080 is applied to first folding member 9010 folding first folding member 9010 to couple to second folding member 9060. The force 9080 corresponds to the walls of an ear canal when ear device 9000 is inserted into the ear canal. Second folding member 9060 or second folding member 9012 is configured to flex or fold. More specifically, second folding member 9060 or 9012 is configured to flex, fold, and conform when first folding member couples to second folding member 9060 or second folding member 9012. Second folding member 9060 or second folding member 9012 conforms to the shape and contour of the ear canal when inserted in the ear canal. As disclosed at least a portion of the outer surface of the second folding member 9060 or second folding member 9012 is configured to couple to at least a portion of an interior surface of first folding member 9010 to seal chamber 9018.

Referring briefly to FIG. 56, chamber 9018 is normally open when ear device 9000 is outside the ear canal. Normally open corresponds to ring valve 9020 being open. Thus, chamber 9018 is coupled to the external environment prior to ear device 9000 being inserted into the ear canal.

Referring briefly to FIG. 58, ear device 9000 is inserted in an ear canal 9002. First folding member 9010 couples to second folding member 9012 such that chamber 9018 is sealed. Ring valve 9020 is closed when chamber 9018 is sealed. A gap in ring valve 9020 prior to ring valve 9020 sealing couples chamber 9018 to the external environment. Thus, when chamber 9018 is sealed the pressure within chamber 9018 is approximately equal to a pressure in the external environment. In one embodiment, first folding member 9010 decouples from second folding member 9012 or second folding member 9060 as chamber 9018 adjusts to a change in diameter of the ear canal to conform to occlude or partially occlude the ear canal. This corresponds to a gap opening in ring valve 9020 that couples chamber 9018 to the external environment thereby equalizing the pressure within chamber 9018 to approximately the pressure of the external environment. Ring valve 9020 closes once the chamber conforms to the diameter of the ear canal sealing chamber 9018. Ear canal 9002 is then isolated from the external environment by chamber 9018 that is sealed. Noise in the external environment is attenuated by stop flange 9008 and chamber 9018 before reaching ear canal 9002.

Referring briefly to FIG. 58, chamber 9018 is configured to seal as ear device 9000 is inserted into ear canal 9002. Chamber 9018 is configured to occlude or partially occlude the ear canal when sealed. Chamber 9018 comprises first folding member 9010 and second folding member 9012 or second folding member 9060. First folding member 9010 couples around stent 9006. An outer surface of first folding member 9010 is configured to couple to a surface of ear canal 9002. Second folding member 9012 or second folding member 9060 couples around stent 9006. At least a portion of first folding member 9010 overlies at least a portion of second folding member 9012 or second folding member 9060. First folding member 9010 is configured to couple to the second folding member 9012 or second folding member 9060 when inserted into ear canal 9002. In one embodiment, a gap exists between first folding member 9010 and second folding member 9012 or second folding member 9060 when ear device 9000 is outside ear canal 9002. The gap couples the external environment to chamber 9018 when ear device 9000 is outside ear canal 9002. First folding member 9010 couples to second folding member 9012 or second folding member 9060 to close the gap when ear device 9000 is inserted in ear canal 9002 thereby sealing chamber 9018. The gap opens between first folding member 9010 and second folding member 9012 or second folding member 9060 during insertion into ear canal 9002 to equalize pressure between chamber 9018 and the external environment.

Referring briefly to FIG. 58, a pressure within chamber 9018 is approximately constant as a volume of chamber 9018 increases or decreases. In one embodiment, a volume decrease in chamber 9018 corresponds to a reduction in diameter of ear canal 9002. The reduction in diameter of ear canal 9002 expels gas within chamber 9018 thereby opening ring valve 9020. Displacing the gas to accommodate the smaller volume maintains the pressure within chamber 9018 approximately equal to the external environment. In one embodiment, a volume increase in chamber 9018 corresponds to an increase in diameter of ear canal 9002. The increase in diameter of ear canal 9002 supports opening of ring valve 9020. Opening ring valve 9020 couples chamber 9018 to the external environment thereby equalizing the pressure within chamber 9018 to the approximately equal to the external environment when ring valve 9020 closes. In one embodiment, a volume in chamber 9018 can be filled in part by a gas, foam, or liquid.

FIGS. 65A and 65B illustrate an earplug where a first sealed chamber 30 is inflated by moving fluid 40 from a second sealed chamber 10 my pressing Y1 on the second sealed chamber, where a valve 20 prevents backflow. A rotatable element 6500 attached to a flexible stent to which the valve 20 is attached, can be rotated 6600, to open the valve releasing the fluid 40 from the first sealed chamber 30 toward the second sealed chamber 10.

FIG. 66 is a cutaway view of a molded ear device 6000 without a stop flange in accordance with an example embodiment. The front tip portion 6620 is molded as shown, then folded toward ridge 6610 to form a tip. This way a nearly enclosed tip can be molded.

Processes, techniques, apparatus, and materials as known by one of ordinary skill in the art may not be discussed in detail but are intended to be part of the enabling description where appropriate. For example, specific materials may not be listed for achieving each of the targeted properties discussed, however one of ordinary skill would be able, without undo experimentation, to determine the materials needed given the enabling disclosure herein.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used, the intended meaning is "substantially orthogonal" and "substantially perpendicular" respectively. Additionally, although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. An ear device comprising:
   a stent;
   a first folding member coupled to the stent; and
   a second folding member coupled to the stent wherein the first folding overlies the second folding member, wherein the first folding member couples to the second folding member when inserted to the ear canal, and wherein the first and second folding member are configured to form a chamber around the stent to occlude or partially occlude the ear canal after insertion in the ear canal, wherein the chamber is configured to be open to an external environment prior to insertion into the ear canal, and wherein a pressure within the chamber when sealed is approximately equal to a pressure in the external environment.

2. The ear device of claim 1 wherein the first folding member couples circumferentially to the stent, wherein the second folding member couples circumferentially to the stent, and wherein a stop flange couples to the stent.

3. The ear device of claim 1 wherein the first folding member couples proximally to the stent in relation to the second folding member and wherein the first folding member and the second folding member form a valve.

4. The ear device of claim 3 wherein the first folding member overlying the second folding member forms a ring valve such that a gap between the first folding member and the second folding member is in a shape of a ring around the stent.

5. The ear device of claim 3 wherein the first folding member is configured to fold or flex towards the stent during insertion of the ear device into the ear canal and couple to the second folding member.

6. The ear device of claim 3 wherein at least a portion of the outer surface of the first folding member is configured to couple to and conform to a surface of the ear canal.

7. The ear device of claim 5 wherein the second folding member is configured to flex or fold and wherein at least a portion of the outer surface of the second folding member is configured to couple to at least a portion of an interior surface of the first folding member to seal the chamber.

8. The ear device of claim 1 wherein the chamber is configured to couple to the external environment due to a change in a diameter of the ear canal during insertion and wherein the chamber can include a gas, foam, or liquid.

* * * * *